US012397067B2

(12) United States Patent
Kohle et al.

(10) Patent No.: US 12,397,067 B2
(45) Date of Patent: Aug. 26, 2025

(54) SULFUR- OR HEAVY ATOM-CONTAINING NANOPARTICLES, METHODS OF MAKING SAME, AND USES THEREOF

(71) Applicant: Cornell University, Ithaca, NY (US)

(72) Inventors: Ferdinand F.E. Kohle, Tubingen (DE); Joshua A. Hinckley, Ithaca, NY (US); Nikhil Dhawan, Poughkeepsie, NY (US); Ulrich B. Wiesner, Ithaca, NY (US)

(73) Assignee: Cornell University, Ithaca, NY (US)

( * ) Notice: Subject to any disclaimer, the term of this patent is extended or adjusted under 35 U.S.C. 154(b) by 613 days.

(21) Appl. No.: 16/604,531

(22) PCT Filed: Apr. 10, 2018

(86) PCT No.: PCT/US2018/026980
§ 371 (c)(1),
(2) Date: Oct. 10, 2019

(87) PCT Pub. No.: WO2018/191316
PCT Pub. Date: Oct. 18, 2018

(65) Prior Publication Data
US 2020/0155710 A1 May 21, 2020

Related U.S. Application Data

(60) Provisional application No. 62/483,687, filed on Apr. 10, 2017.

(51) Int. Cl.
| | |
|---|---|
| *A61K 9/00* | (2006.01) |
| *A61K 47/60* | (2017.01) |
| *A61K 47/69* | (2017.01) |
| *A61K 49/00* | (2006.01) |
| *G01N 21/64* | (2006.01) |
| *A61K 45/06* | (2006.01) |
| *B82Y 5/00* | (2011.01) |
| *B82Y 30/00* | (2011.01) |
| *B82Y 40/00* | (2011.01) |

(52) U.S. Cl.
CPC .......... *A61K 49/0093* (2013.01); *A61K 47/60* (2017.08); *A61K 47/6923* (2017.08); *A61K 47/6929* (2017.08); *A61K 49/0032* (2013.01); *G01N 21/6458* (2013.01); *A61K 45/06* (2013.01); *B82Y 5/00* (2013.01); *B82Y 30/00* (2013.01); *B82Y 40/00* (2013.01)

(58) Field of Classification Search
CPC ................ A61K 9/0009; A61K 9/5115; A61K 41/0042; A61K 41/0057; A61K 2800/43
See application file for complete search history.

(56) References Cited

U.S. PATENT DOCUMENTS

| | | | |
|---|---|---|---|
| 8,298,677 B2 | 10/2012 | Wiesner et al. | |
| 9,625,456 B2 | 4/2017 | Bradbury et al. | |
| 11,291,737 B2 | 4/2022 | Wiesner et al. | |
| 2008/0063868 A1 | 3/2008 | Chung et al. | |
| 2009/0101838 A1* | 4/2009 | Boyden ................ | A61K 41/17 252/301.16 |
| 2010/0330366 A1 | 12/2010 | Keiser et al. | |
| 2012/0223273 A1 | 9/2012 | Wiesner et al. | |
| 2012/0283379 A1 | 11/2012 | Auger et al. | |
| 2013/0039848 A1 | 2/2013 | Bradbury | |
| 2013/0064776 A1* | 3/2013 | El Harrak ............ | G01N 33/582 435/7.1 |
| 2014/0248210 A1* | 9/2014 | Bradbury ........... | A61K 51/1244 424/9.4 |
| 2015/0366995 A1 | 12/2015 | Wiesner | |
| 2016/0018404 A1 | 1/2016 | Iyer | |
| 2016/0287717 A1 | 10/2016 | Brinker et al. | |
| 2018/0050115 A1 | 2/2018 | Mou et al. | |
| 2018/0099050 A1 | 4/2018 | Trogler et al. | |
| 2018/0133346 A1 | 5/2018 | Wiesner et al. | |
| 2020/0101180 A1 | 4/2020 | Bradbury et al. | |
| 2020/0179538 A1 | 6/2020 | Ma et al. | |

FOREIGN PATENT DOCUMENTS

| | | |
|---|---|---|
| CN | 102459062 A | 5/2012 |
| CN | 107456927 A | 12/2017 |
| CN | 105056233 B | 3/2018 |
| EP | 2449379 B1 | 5/2017 |
| JP | 2009220026 A | 10/2009 |

(Continued)

OTHER PUBLICATIONS

Benezra et al., Multimodal silica nanoparticles are effective cancer-target probes in a model of human melanoma, Journal of Clinical Investigation, vol. 121, No. 7, pp. 2768-2780 Jul. 1, 2011.
Chen et al., Cancer-Targeting Ultrasmall Silica Nanoparticles for Clinical Translation: Physicochemical Structure and Biological Property Correlations, Sep. 15, 2017, vol. 29, pp. 8766-8779.
Chen et al., Melanocortin-1 Receptor-Targeting Ultrasmall Silica Nanoparticles for Dual-Modality Human Melanoma maging, Feb. 7, 2018, vol. 5, No. 10, pp. 4379-4393.
International Search Report and Written Opinion of corresponding International Application No. PCT/US2018/026980 filed Apr. 10, 2018, all enclosed pages cited.
Lillo et al., Organic-coating of 1-2 nm size silicon nanoparticles: effect on particle properties, Nano Research, vol. 8, No. 6, pp. 2047-2062 Jan. 8, 2015.

(Continued)

*Primary Examiner* — Micah Paul Young
(74) *Attorney, Agent, or Firm* — Young Basile Hanlon & MacFarlane, P.C.

(57) ABSTRACT

Provided are sulfur- or heavy atom-containing silica or aluminosilica nanoparticles. A nanoparticle can have at least one dye molecule covalently bonded to the silica or aluminosilica matrix of the silica or aluminosilica nanoparticle, respectively. The nanoparticle may have a size, such as, for example, a longest dimension, of less than 10 nm. The silica or aluminosilica nanoparticle can be used in methods such as, for example, imaging methods and photodynamic therapy methods. The imaging methods can provide sub-diffraction limit resolution.

26 Claims, 25 Drawing Sheets

(56) References Cited

FOREIGN PATENT DOCUMENTS

| | | | |
|---|---|---|---|
| JP | 2012-594014 A | 10/2012 | |
| JP | 2017-031014 A | 2/2017 | |
| KR | 101622239 B1 | 5/2016 | |
| WO | 2009/029870 A2 | 3/2009 | |
| WO | 2010/121064 A2 | 10/2010 | |
| WO | 2011/003109 A1 | 1/2011 | |
| WO | WO-2011133925 A2 * | 10/2011 | ......... A61K 41/0038 |
| WO | 2013/192609 A1 | 12/2013 | |
| WO | 2014/130643 A1 | 8/2014 | |
| WO | 2016/149378 A1 | 9/2016 | |
| WO | 2016/179260 A1 | 11/2016 | |
| WO | 2017/136641 A1 | 8/2017 | |
| WO | 2018/213851 A1 | 11/2018 | |
| WO | 2018/217528 A1 | 11/2018 | |

OTHER PUBLICATIONS

Ma et al., Ultrasmall Sub-10 nm Near-Infrared Fluorescent Mesoporous Silica Manoparticles, Journal of the American Chemical Society, Jul. 25, 2012, vol. 134, pp. 13180-13183.

Ma. K., et al., Controlling Growth of Ultrasmall Sub-10 nm Fluorescent Mesoporous Silica Nanoparticles, Chemistry of Materials, Feb. 11, 2013, vol. 25, pp. 677-691.

Ma, K., et al., Control of Ultrasmall Sub-10 nm Ligand-Functionalized Fluorescent Core-Shell Silica Nanoparticle Growth in Water, Chem. Mater., May 13, 2015, vol. 27, May 13, 2015, pp. 4119-4133.

Ma et al., Elucidating the Mechanism of Silica Nanoparticle PEGylation Processes Using Flourescence Correlation Spectroscopies, vol. 28, No. 5, pp. 1537-1545 Feb. 8, 2016.

Ma et al., Modular and Orthogonal Post-PEGylation Surface Modifications by Insertion Enabling Penta-functional Ultrasmall Organic-Silica Hybrid Nanoparticles, Chemistry of Materials, Jul. 23, 2017, vol. 29, No. 16, pp. 6840-6855.

Mendoza, Cornell Prime Dots (C' dots): Ultrasmall PEDylated Flourescent Core-Shell Silica Nanoparticles for Cancer Theranostics, pp. 1-28 May 1, 2016.

Poduval, D.G., On the Role of Acidity in Amorphous Silica-Alumina Based Catalysts, Eindhoven University of lrechnology Library, Thesis, Apr. 5, 2011, 51 pages.

Rio-Echevarria et al., Highly PEGylated silica nanoparticles: "ready to use" stealth functional nanocarriers, Journal of Materials Chemistry, vol. 20, No. 14, pp. 2780 Jan. 1, 2010.

Santra, et al., "Conjugation of biomolecules with luminophore-doped silica nanoparticles for photostable biomarkers," Analytical Chemistry, vol. 73, Issue 20 (Sep. 13, 2001), all enclosed pages cited.

Schladt, T. D. et al., Multifunctional superparamagnetic MnO@SiO2 core/shell nanoparticles and their application or optical and magnetic resonance imaging, Journal of Materials Chemistry, 2012, vol. 22, pp. 9253-9262.

Stöber, et al. "Controlled Growth of Monodisperse Silica Spheres in the Micron Size Range," Journal of Colloid and Interface Science, 26, (1968), all enclosed pages cited.

Sun et al., Water-Based Synthesis of Ultrasmall PEGylated Gold-Silica Core-Shell Nanoparticles with Long-Term Stability, Chemistry of Materials, Sep. 5, 2014, vol. 26, pp. 5201-5207.

Yeoh et al., "Preparation and Characterization of Sulpho-functionalized Ordered Mesoporous Silica," Adsorption Science & Technology, Sep. 1, 2008, pp. 479-489, vol. 26, No. 7.

Gobel et al., "Modular Thiol-Ene Chemistry Approach towards Mesoporous Silica Monoliths with Organically Modified Pore Walls," Chemistry European Journal, Dec. 22, 2014, pp. 17579-17589, vol. 20, Issue 52.

Thorat et al., "Synthesis and Stability of IR-820 and FITC Doped Silica Nanoparticles," Journal of Colloid and Interface Science, Mar. 15, 2017, pp. 294-302, vol. 490.

Chang et al., "A Hydrophobic Dye-Encapsulated Nano-Hybrid as an Efficient Fluorescent Probe for Living Cell Imaging," Advanced Healthcare Materials, Jun. 5, 2012, pp. 475-479 vol. 1, Issue 4.

* cited by examiner a b c

Cy3-biotin

Cy5-biotin

DY782-NHS

| Sample | QE [%] | $d$ [nm] | $n$ [#] |
|---|---|---|---|
| Cy3-NHS | 1.0 | 1.41 | 1.0 |
| Cy3-biotin | 1.4 | 1.46 | 1.0 |
| Cy3 C' dots | 3.5 | 5.13 | 1.5 |
| Cy3 srC' dots | 3.7 | 7.6 | 1.1 |
| Cy5-NHS | 1.0 | 1.29 | 1.1 |
| Cy5-biotin | 2.1 | 1.56 | 1.0 |
| Cy5 C' dots | 2.3 | 5.36 | 1.6 |
| Cy5 srC' dots | 2.3 | 7.43 | 1.1 |
| DY782-NHS | 1.0 | 1.57 | 1.0 |
| DY782 srC' dots | 9.3 | 10.60 | 1.1 |

SULFUR- OR HEAVY ATOM-CONTAINING NANOPARTICLES, METHODS OF MAKING SAME, AND USES THEREOF

CROSS REFERENCE TO RELATED APPLICATIONS

This application claims priority to U.S. Provisional Application No. 62/483,687, filed on Apr. 10, 2017, the disclosure of which is hereby incorporated by reference.

STATEMENT REGARDING FEDERALLY SPONSORED RESEARCH

This invention was made with government support under contract nos. DE-SC0010560 awarded by the Department of Energy, U54CA199081 awarded by the National Institutes of Health, and DMR-1719875 and DBI-1428922 awarded by the National Science Foundation. The government has certain rights in the invention.

FIELD OF THE DISCLOSURE

The disclosure generally relates to sulfur- or heavy atom-containing silica or aluminosilicate nanoparticles and uses thereof.

BACKGROUND OF THE DISCLOSURE

Overcoming Abbe's diffraction limit with far-field fluorescence microscopy has led to a cascade of new microscopy concepts and a renewed interest in the photochemistry and photophysics of fluorescent markers. The general principle of super-resolution (SR) microscopy is the activation of only a single point-like emitting source within a diffraction-limited area at any time, while other emitters are in a dark state. The origin of the emitting source can then be precisely localized. Repeated photoswitching and localizing of different fluorophores eventually resolves spatial features below the diffraction limit. Different microscopy concepts impose different requirements onto fluorescent markers. Stimulated emission depletion (STED) microscopy demands photostable fluorophores to withstand high laser intensities. In ground state depletion (GSD) microscopy, photoswitching is achieved by shelving fluorophores in long-lived triplet states accessed at lower irradiances as compared to STED, thereby reducing phototoxicity but requiring high triplet yields. Stochastic SR methods, e.g. stochastic optical reconstruction microscopy (STORM), rely on bright and photoswitchable fluorescent probes to localize single molecules. While the chemical structure of a fluorophore determines many of its optical properties, the chemical and physical environment can significantly modulate its behavior. Such effects have been prominently studied for the cyanine dye, Cy5. Exposed to primary thiols, such as β-mercaptoethanol (βME), Cy5 undergoes photo-conversion between bright and long-lived dark states by forming a Cy5-thiol adduct, suggesting the use of 'imaging cocktails.' Different cocktails for single molecule localization have been described. However, while supporting favorable emissive behavior, they may compromise cell integrity or may not be compatible with the experimental conditions, particularly relevant for sensitive live cell imaging.

Fluorescent proteins (FPs) and photoswitchable nanoparticles (NPs) as fluorescent markers, including quantum dots (QDs) or photochromic dye-containing NPs, present an alternative for cocktail-free SR microscopy. While FPs ~3-5 nm in size can be genetically encoded, they often lack brightness and photostability. QDs have broad absorption bands, high photon yields and are photostable, while SR exploits intrinsic QD-blinking. However, emissive properties are size dependent, and use in biological samples requires passivation layers, complicating syntheses and limiting size tunability. Photochromic dyes, i.e. spiropyrans or diarylethenes, encapsulated into polymeric NPs or silica nanoparticles (SNPs) provide alternatives to QDs. The host NPs overcome drawbacks of these dyes, such as low solubility in aqueous media, pH dependent emission, or cytotoxicity. However, encapsulation retards dye photo-isomerization kinetics, leading to elongated acquisition times. Furthermore, for dyad systems (photochrome-fluorophore), three excitation wavelengths are needed (i.e. switch-on, switch-off, and probe), facing an excitation/erasing problem caused by triggering the switching-mechanism while probing the sample. A general problem to date of photoswitchable NPs systems, in particular for stochastic SR microscopy, is their large size (>10 nm), which may interfere with biological function, alter the object morphology, bias labeling sites, or broaden the location of the point emitter, thereby limiting localization accuracy.

Photodynamic therapy (PDT) renders a non-invasive, and alternative therapeutic modality for the treatment of cancer, acne, and other diseases. PDT utilizes the cytotoxicity of singlet oxygen which is locally generated at the diseased tissue. This is achieved by an energy transfer reaction between molecularly dissolved triplet oxygen and a photosensitizer (PS). For minimizing side-effects, such as damage of healthy tissue by cytotoxic singlet oxygen, specific drug targeting, rapid post-treatment clearance, high local drug concentrations at the site of interest and solubility in physiological media are important. High singlet oxygen quantum yields are desired for the efficient generation of singlet oxygen.

Different NP-based systems have been described in the literature, e.g. PEGylated liposomes, polymeric NPs, iron oxide NPs, and gold NPs. However, these systems suffer from various limitations.

Based on the foregoing there exists and ongoing and unmet need for optical nanoprobes for super-resolution microscopy and photodynamic therapy.

SUMMARY OF THE DISCLOSURE

The present disclosure provides silica or aluminosilica nanoparticles comprising one or more dye molecules and one or more sulfur atoms or one or more heavy atoms. The present disclosure also provides methods of making and using the nanoparticles.

In an aspect, the present disclosure provides silica nanoparticles and aluminosilicate nanoparticles. The nanoparticles comprise sulfur atoms or heavy atoms. The nanoparticles may have one or more dye covalently bonded to the nanoparticle. The nanoparticles are microporous.

In an aspect, the present disclosure provides compositions. The compositions comprise a plurality of nanoparticles of the present disclosure. A composition may comprise a mixture of two or more different nanoparticles. In various examples, a composition comprises one or more types (e.g., having different average size and/or one or more different compositional feature).

In various aspects, the present disclosure provides methods of making nanoparticles and/or compositions of the present disclosure. The methods can use sulfur-containing precursors or heavy atom-containing precursors.

In various aspects, the present disclosure provides uses of nanoparticles and/or compositions of the present disclosure. Non-limiting examples of uses of the nanoparticles and/or compositions of the present disclosure include imaging methods and photodynamic therapy (PDT) methods, and the like.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
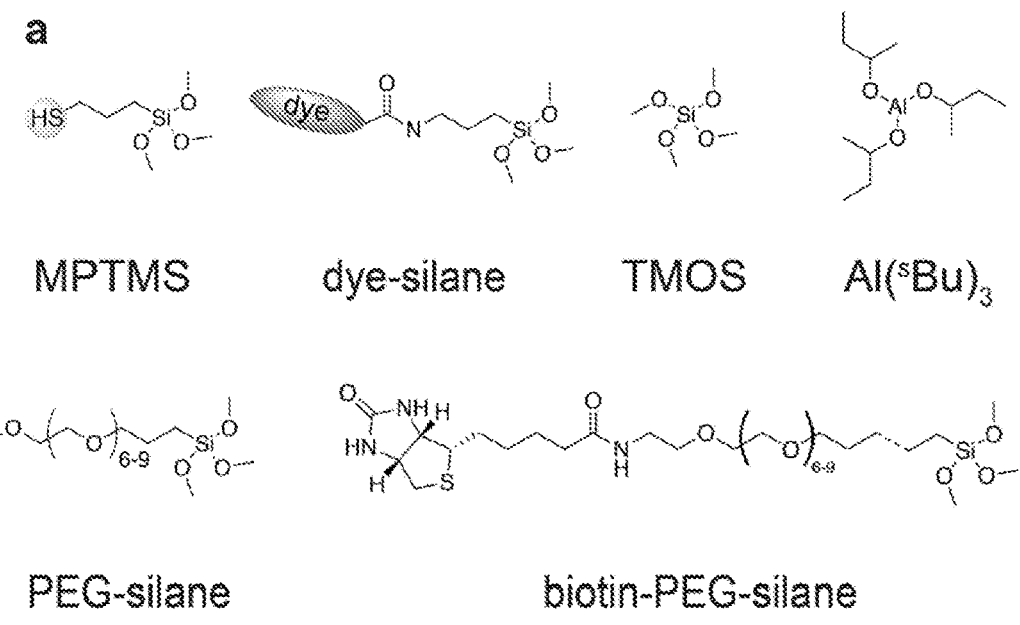
FIG. 1 shows an introduction to particle synthesis and the principle of STORM. (a) Chemical structures of the precursor molecules used for the synthesis of biotin-functionalized srC' dots. From left to right: (3-mercaptopropyl)trimethoxysilane (MPTMS), dye-silane, tetramethylorthosilicate (TMOS), aluminum-tri-sec-butoxide (Al(sBu)3), polyethylene glycol-silane (PEG-silane), and biotin-polyethylene glycol-silane (biotin-PEG-silane) (dotted line represents a thioether linker). (b) Cy5 reversible photoswitching mechanism in the presence of thiol components from fluorescent state (left) to dark state (right) with corresponding particle rendering and local molecular structure models. R and R' represent functional groups attached by a carbon atom. (c) Principle of stochastical optical reconstruction microscopy (STORM) imaging of a hypothetical triangular and switchable red fluorophore arrangement with side lengths below the diffraction limit ($\lambda/2$). Fluorophores are stochastically switched on (i), localized, and switched off (ii). Repeated photoswitching and localization (iii) resolves spatial features below the diffraction limit. (d) Visualization of localization algorithm used in STORM. Pixelated point-spread function of a single fluorophore, imaged by total internal reflection fluorescence microscopy (TIRFM) (i) is modeled by a three-dimensional Gaussian point-spread function (PSF) (ii). Fitting multiple fluorescent states from the same fluorophore leads to a super-resolution image with a localization distribution (iii). When the point-spread functions of two different fluorophores overlap in TIRFM, each fluorophore can be individually localized using STORM (iv).
Figure 1:
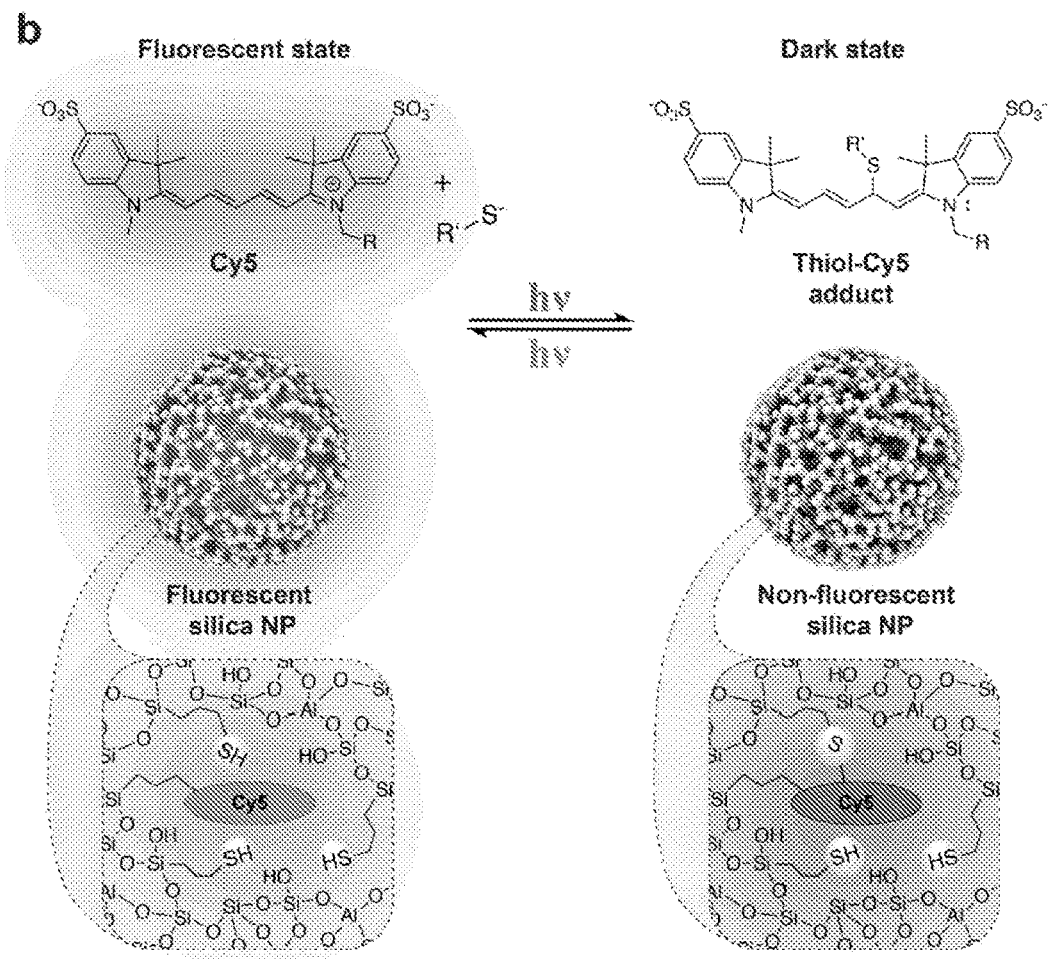
Figure 1:
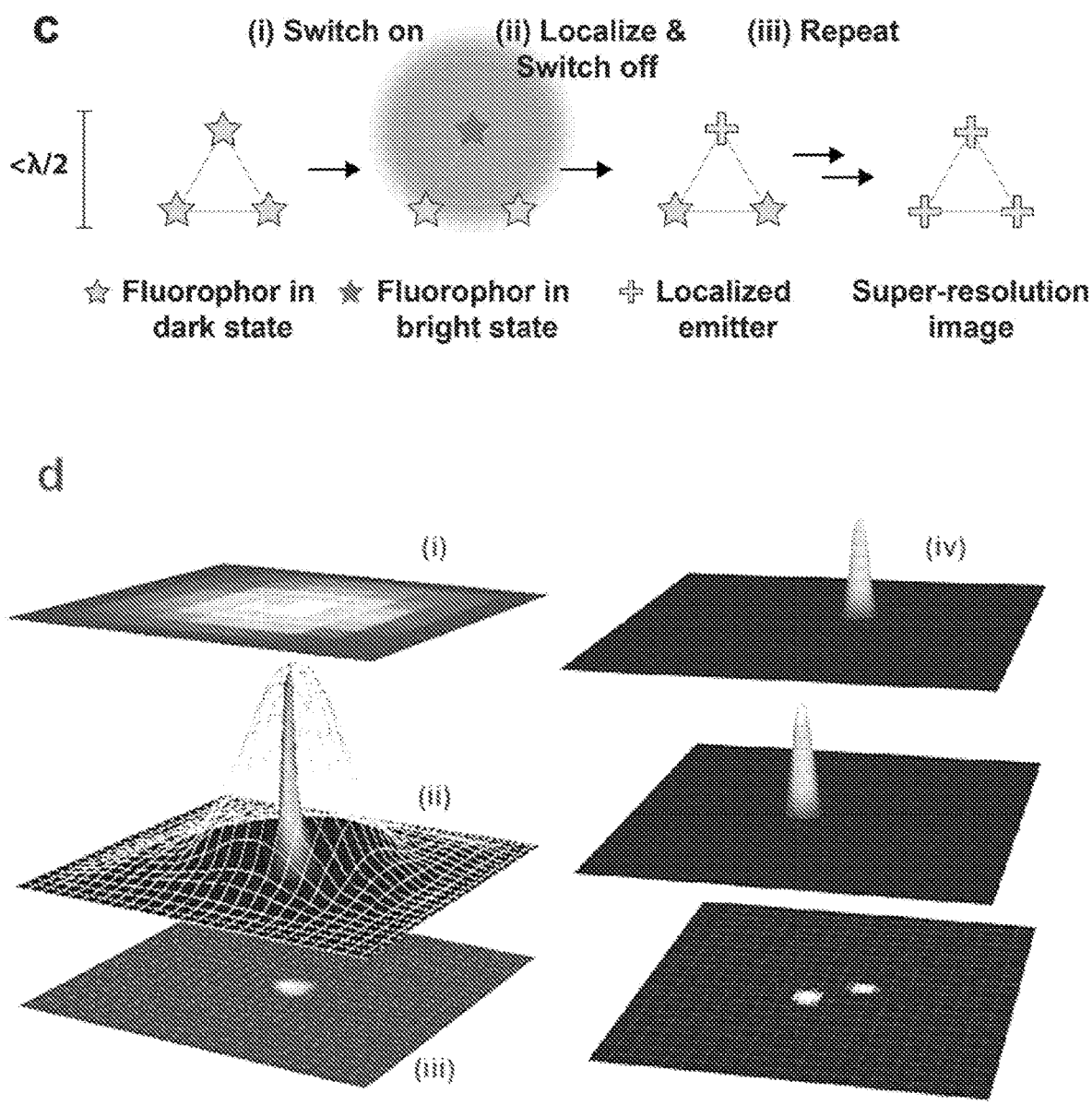

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range. As an illustrative example, any range provided herein includes all values that fall within the ranges to the tenth decimal place, unless indicated otherwise.

The present disclosure provides silica or aluminosilica nanoparticles comprising one or more dye molecules and one or more sulfur atoms or one or more heavy atoms. The present disclosure also provides methods of making and using the nanoparticles.

The present disclosure provides silica-based nanoprobes with sizes below the critical size for renal clearance in the body (e.g., sizes below 10 nm diameter), which enable optical super-resolution microscopy (i.e., optical microscopy with resolution below Abbe's diffraction limit) as well as photodynamic therapy (PDT). The ability to further surface functionalize such new compositions of matter silica nanoprobes with specific surface functional groups, including, for example, chelators for radio-isotopes enabling positron emission tomography (PET) as well as radiotherapy, targeting moieties including specific peptides or antibody fragments for specific targeting of, for example, tumor cells, as well as chemotherapy drugs, provides new nanoparticle platforms for advanced optical imaging as well as therapeutic applications. The nanoparticles further provide access to ultrabright super-resolution probes with substantially enhanced brightness (e.g., up to almost an order of magnitude higher compared to the parent free dye), as well as efficient PDT probes (e.g., with up to order of magnitude improvements in singlet oxygen quantum yields).

As used herein, unless otherwise stated, the term "group," when used in the context of a chemical structure, refers to a chemical entity that has one terminus that can be covalently bonded to other chemical species. Non-limiting, illustrative examples of groups include:

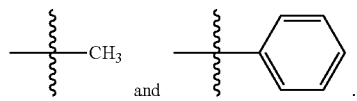

As used herein, unless otherwise stated, the term "moiety" refers to a chemical entity that has two or more termini that can be covalently bonded to other chemical species. Non-limiting, illustrative examples of groups include:

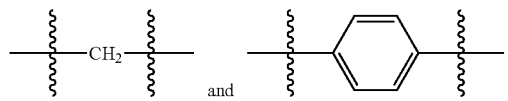

In an aspect, the present disclosure provides silica nanoparticles and aluminosilicate nanoparticles. The nanoparticles comprise sulfur atoms or heavy atoms. The nanoparticles may have one or more dye covalently bonded to the nanoparticle. The nanoparticles are microporous.

The nanoparticles can be made by methods of the present disclosure. In various examples, a nanoparticles is made by a method of the present disclosure.

An aluminosilicate nanoparticle can comprise various amounts of silicon atoms and aluminum atoms. In various examples, an aluminosilicate nanoparticle comprises 0-30 at. % (at. %=atomic percent) (relative to Si) aluminum atoms, including all 0.1 at. % values and ranges therebetween. In an example, an aluminosilicate nanoparticle comprises 1-20 at. % (relative to Si) aluminum atoms. In another example, an aluminosilicate nanoparticle comprises 5-15 at. % (relative to Si) aluminum atoms.

A silica nanoparticle or aluminosilicate nanoparticle may comprise one or more sulfur atoms. Such nanparticles are also referred to herein as srC' dots. The sulfur atoms are covalently bonded to the silica network or aluminosilicate network. Sulfur atoms can be incorporated into a silica or aluminosilicate nanoparticle using a sulfur-containing precursor in the synthesis of the nanoparticle.

A nanoparticle can comprise various amounts of sulfur atoms. For example, a silica or aluminosilicate nanoparticle comprises 0-90 at. % (relative to Si) sulfur atoms, including all 0.1 at. % values and ranges therebetween. In various examples, a silica or aluminosilicate nanoparticle comprises 5-90 at. % (relative to Si), 5-60 at. % (relative to Si), 5-80 at. % (relative to Si), 10-80 at. % (relative to Si), or 30-60 at. % (relative to Si) sulfur atoms.

In various examples, a silica or aluminosilicate nanoparticle comprises 0-90 at. % (relative to Si) (e.g., 10-80 and 30-60 at. % (relative to Si)). The sulfur atom(s) are covalently bonded to the silica network of the silica nanoparticle or covalently bonded to the aluminosilicate network of the aluminosilicate nanoparticle, at least one dye molecule (e.g., 1, 2, 3, 4, or 5 dye molecules) covalently bonded thereto, and a longest dimension of less than 10 nm (e.g., 0.01-9.99 nm, including all 0.01 nm values and ranges therebetween).

A silica nanoparticle or aluminosilicate nanoparticle may comprise one or more heavy atoms. In the case where the heavy atom is iodine, such nanoparticles are also referred to herein as iC' dots. The heavy atoms may either be covalently bonded to the silica network of the silica nanoparticle or the aluminosilicate network of the aluminosilicate nanoparticle or covalently bound to a surface of the nanoparticle or non-covalently bound (e.g, chelated) to a surface of the nanoparticle. A nanoparticle may comprise a mixture of two or more different heavy atoms. The heavy atoms may be either covalently bonded the silica network of the silica nanoparticle or the aluminosilicate network of the aluminosilicate nanoparticle or covalently bound to a surface of the nanoparticle or non-covalently bound (e.g., chelated) to the silica or aluminosilica network. A nanoparticle may comprise a mixture of two or more different heavy atoms.

Heavy atoms may be incorporated into a silica or aluminosilicate nanoparticle by using a heavy atom-containing precursor in the synthesis of the nanoparticle or non-covalently bound (e.g., chelated) to pre-formed nanoparticle. A heavy atom may be a neutral atom or a metal ion.

Non-limiting examples of neutral heavy atoms include iodine atom, bromine atom, and the like covalently bonded to the silica network of the silica nanoparticle or the aluminosilicate network of the aluminosilicate nanoparticle or covalently bound to a surface of the nanoparticle. Non-limiting examples of metal ions include Au ions, Ag ions, Pb ions, Ti ions, Bi ions, Pt ions, In ions, Sn ions, Sb ions or Pd ions, and the like non-covalently bound (e.g., chelated) to a portion of a surface of the nanoparticle and/or non-covalently bound (e.g., chelated) to the silica network of a silicananoparticle or aluninosilica network of an aluminosilicate nanoparticle.

A nanoparticle can comprise various amounts of heavy atom(s). For example, a silica or aluminosilicate nanoparticle comprises 0-20 at. % (relative to Si) heavy atoms, including all 0.1 at % values and ranges therebetween. In various examples, a silica or aluminosilicate nanoparticle comprises (e.g., 1-20 at. % (relative to Si) and 1-10 at. % (relative to Si)) heavy atoms.

In various examples, a silica or aluminosilicate nanoparticle comprises 0-80 at. % (relative to Si) heavy atoms (e.g., 0-70, 0-60, 1-30, or 1-10 at. % (relative to Si)), at least one fluorescent dye molecule (e.g., 1 or 2, dye molecules) covalently bonded thereto, and a longest dimension of less than 10 nm (e.g., 1-9.99 nm, including all 0.01 nm values and ranges therebetween).

The amount of sulfur atoms or other heavy atoms can be determined by methods known in the art. For example, the amount of sulfur atoms or heavy atoms per nanoparticle is determined by EDS spectroscopy. Examples of determination of sulfur atoms or heavy atoms are described in the Example.

A nanoparticle can comprise various dyes. The dyes are organic dyes. In an example, a dye does not comprise a metal atom. A nanoparticle may comprise a mixture of dyes. Non-limiting examples of dyes include fluorescent dyes, non-fluorescent dyes (e.g., non-fluorescent dyes exhibiting less than 1% fluorescence quantum yield), fluorescent proteins (e.g., EBFP2 (variant of blue fluorescent protein), mCFP (Cyan fluorescent protein), GFP (green fluorescent protein), mCherry (variant of red fluorescent protein), iRFP720 (Near Infra-Red fluorescent protein)), and the like. In various examples, a dye absorbs in the UV-visible portion of the electromagnetic spectrum. In various examples, a dye has an excitation and/or emission in the near-infrared portion of the electromagnetic spectrum (e.g., 650-900 nm).

Non-limiting examples of organic dyes include cyanine dyes (e.g., Cy5®, Cy3®, Cy5.5®, Cy7®, and the like), carborhodamine dyes (e.g., ATTO 647N (available from ATTO-TEC and Sigma Aldrich®), BODIPY dyes (e.g., BODIPY 650/665 and the like), xanthene dyes (e.g., fluorescein dyes such as, for example, FITC, Rose Bengal, and the like), eosins (e.g. Eosin Y and the like), and rhodamines (e.g. TAMRA, TMR, TRITC, DyLight® 633, Alexa 633, HiLyte 594), methylene blue, and the like, or a group derived therefrom.

A nanoparticle may comprise a group derived from a dye molecule. For example, a dye molecule or a derivative of a dye molecule is covalently bonded to the network of a nanoparticle (e.g., via a linker moiety, which may be a moiety of a dye precursor). The resulting covalently bonded dye group is derived from an original dye molecule. Illustrative, non-limiting examples of groups derived from a dye molecule are described herein. In an example, a dye is incorporated into the silica or aluminosilicate network using a dye precursor that comprises a dye conjugated to a sol-gel silica precursor (e.g., a —Si(OR)$_3$ group, where R is an alkyl group).

The dyes can be conjugated to a nanoparticle via various moieties. The moiety conjugating a dye to a nanoparticle may be part of (e.g., a moiety of) a dye precursor used in the synthesis of the nanoparticle. In various examples, the dyes are conjugates via amino-silanes and active ester groups on the dye. In various examples, the dyes are not conjugates via mercapto-silanes and maleimido groups on the dye.

A nanoparticle can have various amounts of dye. Without intending to be bound by any particular theory, it is considered that the number of dyes present in a nanoparticle correlates to the amount of dye precursor used in the synthesis of the nanoparticle. As an illustrative example, for particles having a size below 10 nm, such particles typically have, on average, 1-5 dyes per nanoparticle. In various examples, a nanoparticle comprises 1 or 2 dyes.

The number of dyes per nanoparticle can be determined by methods known in the art. For example, the number of dyes per nanoparticle is determined using a combination of fluorescence correlation spectroscopy (FCS), which provides the number of particle in solution (i.e. the particle concentration), and absorption spectroscopy on the particles, which provides the number of dyes in the solution. Dividing the second number by the first gives you the number of dyes per particle.

A nanoparticle can have various sizes. The size of a nanoparticle may be a longest dimension of the nanoparticle. For example, a nanoparticle has a size of 1-9.99 nm, including all 0.01 nm values and ranges therebetween. A size may be a hydrodynamic radius or hydrodynamic diameter. The size of a nanoparticle can be determined by methods known in the art. In various examples, nanoparticle size (or the size (e.g., size distribution) of nanoparticles in a composition) is determined by are determined by FCS and/or dynamic light scattering (DLS).

A nanoparticle or plurality of nanoparticles can exhibit desirable properties. For example, a nanoparticle or plurality of nanoparticles exhibit an increase of the singlet oxygen quantum yield, relative to the free dye(s) used in the nanoparticles in solution (e.g., aqueous solution), of 10% to 1000%, including all integer % values and ranges therebetween. In various examples, a nanoparticle or plurality of nanoparticles exhibit an increase of the singlet oxygen quantum yield, relative to the free dye(s) used in the nanoparticles in solution (e.g., aqueous solution), of 10% or more, 20% or more 30% or more, 40% or more, 50% or more, 75% or more, 100% or more, 250% or more, 500% or more, or 1000% or more. In an example, a nanoparticle exhibits an on/off-duty cycle of 0.0001 to 0.001, including all 0.0001 values and ranges therebetween. In another example, a nanoparticle exhibits an on/off-duty cycle of 0.0001 to 0.001 without the need of any additional 2-mercaptoethanol added to the imaging solution. On/off duty cycle is fluorescent on time/fluorescent off time (e.g., over 10 minutes).

A nanoparticle can have polyethylene glycol (PEG) group(s) and/or moiet(ies) disposed on (e.g. covalently bonded to) a surface of the nanoparticle. The chain length of the PEG group(s)/moiet(ies) (i.e., the molecular weight of the PEG group(s)/moiet(ies)) can be tuned from 3 to 24 ethylene glycol monomers (e.g., 3 to 6, 3 to 9, 6 to 9, 8 to 12, or 8 to 24 ethylene glycol monomers)). The PEG group(s)/moiet(ies) chain length(s) can be selected to tune the thickness of the PEG layer surrounding the particle and the pharmaceutical kinetics profiles of the PEGylated particles. The PEG group/moiety chain length of ligand-functionalized PEG group/moiety be used to tune the accessibility of the ligand groups on the surface of the PEG layer of the particles resulting in varying binding and targeting performance.

In an example, at least a portion of the exterior surface (e.g., at least 20%, 30%, 40% or 50% of the exterior surface) of a silica or aluminosilicate nanoparticle is functionalized with polyethylene glycol groups/moieties. In various examples, the number of PEG group(s)/moiet(ies) disposed on the surface of a nanoparticle is 3 to 600, including all integer number of PEG group(s)/moiet(ies) and ranges therebetween.

A silica nanoparticle or aluminosilicate nanoparticle may comprise a ligand or ligands disposed on (e.g. covalently bonded to) a surface of the nanoparticle. A nanoparticle may have two or more different ligands disposed on a surface. A ligand can be conjugated to (e.g., covalently bonded to) a surface of a nanoparticle. Suitable ligand conjugation methods are known in the art.

At least a portion of an exterior surface of a nanoparticle may be functionalized with at least one ligand. A nanoparticle can have various amounts of ligands. For example, a nanoparticle has 1-50 ligands disposed on (e.g., covalently bonded to) an exterior surface of the nanoparticle. In various examples, a nanoparticle has 1-3 ligands, 1-10 ligands, 1-20 ligands, or 1-40 ligands disposed on (e.g., covalently bonded to) an exterior surface of the nanoparticle.

The ligands carried by the nanoparticles include, but are not limited to, diagnostic and/or therapeutic agents (e.g., drugs). Examples of therapeutic agents include, but are not limited to, chemotherapeutic agents, antibiotics, antifungal agents, antiparasitic agents, antiviral agents, and combinations thereof. An affinity ligand may be also be conjugated to the nanoparticle to allow targeted delivery of the nanoparticles. For example, the nanoparticle may be conjugated to a ligand which is capable of binding to a cellular component (e.g., on the cell membrane or in the intracellular compartment) associated with a specific cell type. The targeted molecule can be a tumor marker or a molecule in a signaling pathway. The ligand can have specific binding affinity to certain cell types, such as, for example, tumor cells. In certain examples, the ligand may be used for guiding the nanoparticles to specific areas, such as, for example, liver, spleen, brain or the like. Imaging can be used to determine the location of the nanoparticles in an individual.

For example, drug-linker conjugate, where the linker group can be specifically cleaved by enzyme or acid condition in tumor for drug release, can be covalently attached to the functional ligands on the particles for drug delivery. For example, drug-linker-thiol conjugates can be attached to maleimido-PEG-particles through thiol-maleimido conjugation reaction post the synthesis of maleimido-PEG-particles. Additionally, both drug-linker conjugate and cancer targeting peptides can be attached to the particle surface for drug delivery specifically to tumor.

A ligand may be a biomolecule. Non-limiting examples of biomolecules include biotin, targeting ligands (e.g., targeting peptides such as, for example, cyclic-RGD and derivatives thereof, alpha-MSH and derivatives thereof, targeting antibody fragments, targeting glycans (e.g., suger molecules targeting cell surface receptors), chelator molecules for metal radioisotopes, such as, for example, deferoxamine (DFO), which is an efficient chelators for radio-labeling with, for example, $Zr^{89}$, NODA, DOTA, drug molecules, and the like. A chelator molecule can form a chelating moiety that binds a radio metal to a nanoparticle. Nanoparticles with radio metals may be used to perform PET or radiotherapy. Nanoparticles with a drug molecule/molecules may be used in therapeutic methods.

In an aspect, the present disclosure provides compositions. The compositions comprise a plurality of nanoparticles of the present disclosure. A composition may comprise a mixture of two or more different nanoparticles. In various examples, a composition comprises one or more types (e.g., having different average size and/or one or more different compositional feature).

For example, a composition comprises a plurality of nanoparticles (e.g., silica nanoparticles, aluminosilicate nanoparticles, and combinations thereof). Any of the nanoparticles may be surface functionalized with one or more type of polyethylene glycol groups (e.g., polyethylene glycol groups, functionalized (e.g., functionalized with one or more ligand and/or a reactive group) polyethylene glycol groups, or a combination thereof).

In various examples, a composition comprises a plurality of nanoparticles of the present disclosure. The composition may further comprises an aqueous medium and the nanoparticles are present as a dispersion in the aqueous medium. Non-limiting examples of aqueous media include buffers and the like. For example, the composition can also comprise a buffer suitable for administration to an individual (e.g., a mammal such as, for example, a human). The buffer may include or be a pharmaceutically-acceptable carrier.

A composition may comprise one or more pharmaceutically acceptable carriers or excipients. The carriers or excipient are "acceptable" in the sense of being compatible with the other ingredients of the formulation and not deleterious to the recipient thereof. Examples of pharmaceutically-acceptable carriers or excipients include pharmaceutically-acceptable material, composition or vehicle, such as a liquid or solid filler, diluents, bulking agents, stabilizers, solvent or encapsulating material involved in carrying or transporting the subject chemical from one organ, or portion of the body, to another organ, or portion of the body, or stabilizing the active ingredient. Examples of pharmaceutically acceptable carriers, excipients, and stabilizers can be found in *Remington: The Science and Practice of Pharmacy* (2005) 21st Edition, Philadelphia, PA Lippincott Williams & Wilkins. For example, suitable carriers or excipients which are nontoxic to recipients at the dosages and concentrations employed, can include buffers such as, for example, acetate, Tris, phosphate, citrate, and other organic acids; antioxidants including ascorbic acid and methionine; preservatives such as, for example, octadecyldimethylbenzyl ammonium chloride; hexamethonium chloride; benzalkonium chloride, benzethonium chloride; phenol, butyl or benzyl alcohol; alkyl parabens such as, for example, methyl or propyl paraben; catechol; resorcinol; cyclohexanol; 3-pentanol; and m-cresol; amino acids such as, for example, glycine, glutamine, asparagine, histidine, arginine, or lysine; monosaccharides, disaccharides, and other carbohydrates including glucose, mannose, or dextrins; chelating agents such as, for example, EDTA; tonicifiers such as, for example, trehalose and sodium chloride; sugars such as, for example, sucrose, mannitol, trehalose or sorbitol; surfactant such as, for example, polysorbate; salt-forming counter-ions such as, for example, sodium; and/or non-ionic surfactants such as, for example, Tween or polyethylene glycol (PEG). The pharmaceutical compositions may comprise other therapeutic agents. The present compositions can be provided as single doses or in multiple doses covering the entire or partial treatment regimen. The compositions can be provided in liquid, solid, semi-solid, gel, aerosolized, vaporized, or any other form from which it can be delivered to an individual.

The nanoparticles in a composition can have a variety of sizes. The nanoparticles can have a size (e.g., a longest dimension such as, for example, a diameter) of less than 10 nm. A size may be a hydrodynamic radius/radii and/or diameter/diameters. In various examples, 1 to 9.99 nm, including all 0.01 nm values and ranges therebetween. In various examples, the nanoparticles have a size of 1, 1.5, 2, 2.5, 3, 3.5, 4, 4.5, 5, 5.5, 6, 6.5, 7, 7.5, 8, 8.5, 9, 9.5, or 9.9 nm. In various examples, at least 90%, 95%, 96%, 97%, 98%, 99%, 99.5% 99.9%, or 100% of the nanoparticles have a size of less than 10 nm (e.g., 0.1 to 9.99 nm, including all 0.01 nm values and ranges therebetween). For the exemplary size distributions, the composition may not be subjected to any particle-size discriminating (particle size selection/removal) processes (e.g., filtration, dialysis, chromatography (e.g., GPC), centrifugation, etc.).

The compositions, for example, as synthesized and before any post-synthesis processing/treatment, may have nanoparticles (e.g., less than 10 nm), dust particles/aggregates (>20 nm), and unreacted reagents (<2 nm). For example, the nanoparticles of the present disclosure are the only nanoparticles in the composition.

In various aspects, the present disclosure provides methods of making nanoparticles and/or compositions of the present disclosure. The methods can use sulfur-containing precursors or heavy atom-containing precursors.

The methods as described herein can be linearly scaled up, e.g., from 10 mL reaction to 1000 mL or greater without any substantial change in product quality. This scalability is important for large scale manufacture of the nanoparticles.

The methods are carried out in an aqueous reaction medium (e.g., water). Certain precursors/reactants are added to the various reaction mixtures as solutions in a polar aprotic solvent (e.g., DMSO, DMF, and the like, and combinations thereof). In various examples, the aqueous medium does not contain organic solvents (e.g., alcohols such as $C_1$ to $C_6$ alcohols) other than polar aprotic solvents at 10% or greater, 20% or greater, or 30% or greater. In an example, the aqueous medium does not contain alcohols at 1% or greater, 2% or greater, 3% or greater, 4% or greater, or 5% or greater. In an example, the aqueous medium does not contain any detectible alcohols. For example, the reaction media of any of the steps of any of the methods disclosed herein consists essentially of water and, optionally, a polar aprotic solvent.

At various points in the methods the pH can be adjusted to a desired value or within a desired range. The pH the reaction mixture can be increased by addition of a base. Examples of suitable bases include ammonium hydroxide.

Without intending to be bound by any particular theory it is considered that the pH of the reaction mixture within a selected range may provide nanoparticles having desired structure and/or properties.

In the case of methods for making aluminosilicate nanoparticles, it is desirable that the pH of the reaction mixture (e.g., at the point of precursor addition) be 0.1-2.5. In various examples, the pH of the reaction mixture (e.g., at the point of precursor addition) is 0.1-2.5, including all 0.01 pH values and ranges therebetween. In an example, the pH of the reaction mixture is 0.5-2.5 or 0.5-1.5.

For example, a method of making silica or aluminosilicate nanoparticles, which can be surface functionalized with polyethylene glycol groups (i.e., PEGylated) comprises: a) forming a reaction mixture at room temperature (e.g., 15° C. to 25° C. depending on the location) comprising water, TMOS (a silica-forming precursor) (e.g., at a concentration of 11 mM to 270 mM), optionally, an alumina-forming precursor (e.g., at a concentration of 0.01 mM to 0.1 mM), and, optionally, a sulfur-containing precursor (e.g., at a concentration of 9 mM to 250 mM) or heavy atom-containing precursor (e.g., at a concentration of 1 mM to 300 mM), where, the in case of making aluminosilicate precursors, the pH of the reaction mixture (which can be adjusted using an acid such as, for example, hydrochloric acid) is, for example, 0.1 to 2.5 or in the case of silica precursors is the pH of the reaction mixture (which can be adjusted using a base such as, for example, ammonium hydroxide) is, for example, 6 to 9 (which results in formation of precursor nanoparticles having an average size (e.g., longest dimension) of, for example, 1 nm to 9 nm, including all 0.01 nm values and ranges therebetween); b) optionally, holding the reaction mixture at a time ($t^1$) and temperature ($T^1$) (e.g., (e) 0.5 days to 7 days at room temperature to 95° C. ($T^1$)), whereby nanoparticles having an average size (e.g., longest dimension) of less than 10 nm (e.g., 1 to 9.9 nm, including all 0.01 values and ranges therebetween) are formed; and c) optionally, (PEGylating the nanoparticles by) adding at room temperature to the reaction mixture comprising the nanoparticles b) a PEG-silane conjugate (comprising a PEG moiety covalently bonded to a silane moiety) (e.g., at a concentration of 10 mM to 60 mM) (e.g., PEG-silane conjugate dissolved in a polar aprotic solvent such as, for example, DMSO or DMF) and holding the resulting reaction mixture at a time ($t^2$) and temperature ($T^2$) (e.g., ($t^2$) 0.5 minutes to 24 hours at room temperature ($T^2$)) (whereby at least a portion of the PEG-silane conjugate molecules are adsorbed on at least a portion of the surface of the nanoparticles from b)); d) heating the mixture from c) at a time ($t^3$) and temperature ($T^3$) (e.g., ($t^3$) 1 hour to 24 hours at 40° C. to 100° C. ($T^3$)), whereby the silica nanoparticles or aluminosilicate nanoparticles surface functionalized with polyethylene glycol groups are formed.

The nanoparticles can be subjected to post-synthesis processing steps. For example, after synthesis (e.g., after d) in the example above) the solution is cooled to room temperature and then transferred into a dialysis membrane tube (e.g., a dialysis membrane tube having a Molecular Weight Cut off 10,000, which are commercially available (e.g., from Pierce)). The solution in the dialysis tube is dialyzed in DI-water (volume of water is 200 times more than the reaction volume, e.g. 2000 mL water for a 10 mL reaction) and the water is changed every day for one to six days to remove remaining reagents, e.g. ammonium hydroxide, free silane molecules, and the like. The particles are then filtered through a 200 nm syringe filter (Fisherbrand) to remove aggregates or dust. If desired, additional purification processes, including gel permeation chromatography and high-performance liquid chromatography, can be applied to the nanoparticles to further ensure the high purify of the synthesized particles (e.g., 1% or less unreacted reagents or aggregates). After any purification processes, the purified nanoparticles can be transferred back to deionized water if other solvent is used in the additional processes.

The nanoparticles can be silica (e.g., $SiO_2$) nanoparticles. The reaction mixture used in silica nanoparticle formation may comprise tetramethylorthosilicate (TMOS) as the only silica-forming precursor.

The nanoparticles can be aluminosilicate nanoparticles. The reaction mixture used in aluminosilicate nanoparticle formation may comprise TMOS as the only silica-forming precursor and one or more alumina-forming precursor (e.g., an aluminum alkoxide such as, for example, aluminum-tri-sec-butoxide, or a combination of aluminum alkoxides). In an example, the alumina-forming precursor is present at 0.01-0.4 mmol, including every 0.01 mmol value and range therebetween, and the heavy atom-containing precursor is present at 0.04-0.4 mmol, including all 0.01 mmol values and ranges therebetween.

The reaction mixture may comprise one or more sulfur-containing precursors. In an example, a sulfur-containing precursor comprises a sulfur atom, which is covalently bonded to the precursor) and a silane moiety (e.g., —Si(OR)$_3$, where R is an alkyl group). Non-limiting examples of sulfur-containing precursors include 3-mercaptopropyl trimethoxysilane (MPTMS), 3-mercaptopropyl triethoxysilane (MPTES), and the like.

The reaction mixture may comprise one or more heavy atom-containing precursors. In an example, a heavyatom-containing precursor comprises a heavy atom, which is covalently bonded or non-covalently bound (e.g., chelated) to the precursor) and a silane moiety (e.g., —Si(OR)$_3$, where R is an alkyl group). Non-limiting examples of heavy atom-containing precursors include 3-iodopropyl trimethoxysilane (IPTMS), 3-bromopropyltrimethoxysilane (BrTMS), and the like. In an example, the heavy atom-containing precursor and sulfur containing precursor are present at 0.04 to 0.4 mmol, including all 0.01 mmol values and ranges therebetween. In another example, the heavy atom-containing precursor and sulfur containing precursor are each present at 0.04 to 0.4 mmol, including all 0.01 mmol values and ranges therebetween.

The amounts of precursors in a reaction mixture can vary. Selection of amount of individual precursors required to provide nanoparticles having a desired composition is withing the purview of one having skill in the art.

In the case of aluminosilicate nanoparticle synthesis, the pH of the reaction mixture is adjusted to a desired pH (e.g., a pH of 0.1 to 2.5) prior to addition of the alumina-forming precursor. After aluminosilicate nanoparticle formation, the pH of the solution is adjusted to a pH of 7 to 9 and, optionally, PEG precursor (e.g., PEG precursor having a PEG group/moiety with a molecular weight between 100 and 1,000 g/mol, including all integer values and ranges therebetween, at concentration of 10 mM to 75 mM, including all integer mM values and ranges therebetween) is added to the reaction mixture prior to adjusting the pH of the reaction mixture to a pH of 7 to 9.

The reaction mixture used to form nanoparticles can also comprise one or more dye precursors. In this case, the resulting nanoparticles have one or more dye molecules encapsulated or incorporated therein. For example, a nanoparticle has 1 or 2 dye molecules encapsulated therein. Mixtures of dye precursors can be used.

The dye precursor is a dye conjugated to a silane. In an example, a dye precursor comprises a dye group (e.g., formed from a dye using conjugation methods known in the art) and a silane moiety (e.g., —Si(OR)$_3$, where R is an alkyl group). For example, a dye with activated ester functionality is conjugated to thiol-functionalized silane. In another example, a dye with NHS ester functionality is conjugated to amine-functionalized silane. Examples of suitable silanes and conjugation chemistries are known in the art. The dye may have an emission (e.g., fluorescence) wavelength of 400 nm (blue) to 900 nm (near-infrared). In an example, the dye(s) do not have to be emissive.

After nanoparticle formation, the nanoparticles can by reacted with one or more PEG-silane precursors (e.g., conjugates). In an example, a PEG-silane precursor (e.g., conjugate) comprises a PEG group (e.g., formed from a PEG molecule using conjugation methods known in the art) and a silane moiety (e.g., —Si(OR)$_3$, where R is an alkyl group). Various PEG-silane conjugates can be added together or in various orders. This process is also referred to herein as PEGylation. The conversion percentage of PEG-silane is between 5% and 40% and the polyethylene glycol surface density is 1.3 to 2.1 polyethylene glycol molecules per nm$^2$. The conversion percentage of ligand-functionalized PEG-silane is 40% to 100% and the number of ligand-functionalized PEG-silane precursors reacted with each particle is 3 to 90.

PEGylation can be carried out at a variety of times and temperatures. For example, in the case of silica nanoparticles, PEGylation can be carried out by contacting the nanoparticles at room temperature for 0.5 minutes to 24 hours (e.g., overnight). For example, in the case of aluminosilicate nanoparticles (e.g., aluminosilicate nanoparticles) the temperature is 80° C. and reaction carried out overnight. The pH of the reaction mixture may be adjusted, if desirable, prior to PEGylatation. For example, the pH of the reaction mixture is adjusted to 6-10 prior to PEGylatation.

The chain length of the PEG group/moiety of the PEG-silane (i.e., the molecular weight of the PEG group/moiety) can be tuned from 3 to 24 ethylene glycol monomers (e.g., 3 to 6, 3 to 9, 6 to 9, 8 to 12, or 8 to 24 ethylene glycol monomers). The PEG group/moiety chain length of PEG-silane can be selected to tune the thickness of the PEG layer surrounding the particle and the pharmaceutical kinetics profiles of the PEGylated particles. The PEG group/moiety chain length of ligand-functionalized PEG-silane can be used to tune the accessibility of the ligand groups on the surface of the PEG layer of the particles resulting in varying binding and targeting performance.

A PEG-silane conjugate may comprise a ligand. The ligand is covalently bonded to the PEG moiety of the PEG-silane conjugates (e.g., via reaction with the hydroxy terminus of the PEG-silane conjugates). The ligand can be conjugated to a terminus of the PEG moiety opposite the terminus conjugated to the silane group (e.g., —Si(OR)$_3$, where R is an alkyl group). The PEG-silane conjugate can be formed using a heterobifunctional PEG compound (e.g., maleimido-functionalized heterobifunctional PEGs, NHS ester-functionalized heterobifunctional PEGs, amine-functionalized heterobifunctional PEGs, thiol-functionalized heterobifunctional PEGs, etc.). Examples of suitable ligands include, but are not limited to, peptides (natural or synthetic), ligands comprising a radio label (e.g., $^{124}$I, $^{131}$I, $^{225}$Ac, $^{177}$Lu, and the like), antibodies, ligands comprising a reactive group (e.g., a reactive group that can be conjugated to a molecule such a drug molecule, gefitinib, etc.).

For example, PEG-silane conjugate comprising a ligand is added in addition to PEG-silane (e.g., in d) in the example above). In this case, nanoparticles surface functionalized with polyethylene glycol groups and polyethylene groups comprising a ligand are formed. The conversion percentage of ligand-functionalized or reactive group-functionalized PEG-silane is 40% to 100% and the number of ligand-functionalized PEG-silane precursors reacted with each particle is 3 to 600.

For example, before or after (e.g., 20 seconds to 5 minutes before or after) the PEG-silane conjugate is added (e.g., in d) in the example above) a PEG-silane conjugate comprising a ligand (e.g., at concentration between 0.05 mM and 2.5 mM) is added at room temperature to the reaction mixture comprising the nanoparticles (e.g., from b) in the example above). The resulting reaction mixture is held at a time ($t^4$) and temperature ($T^4$) (e.g., ($t^4$) 0.5 minutes to 24 hours at room temperature ($T^4$)), where at least a portion of the PEG-silane conjugate molecules are adsorbed on at least a portion of the surface of the nanoparticles (e.g., from b) in the example above). Subsequently, the reaction mixture is heated at a time ($t^5$) and temperature ($T^5$) (e.g., ($t^5$) 1 hour to 24 hours at 40° C. to 100° C. ($T^5$)), where nanoparticles surface functionalized with polyethylene glycol groups comprising a ligand are formed. Optionally, subsequently adding at room temperature to the resulting reaction mixture comprising nanoparticles surface functionalized with polyethylene glycol groups comprising a ligand a PEG-silane conjugate (the concentration of PEG-silane no ligand is between 10 mM and 75 mM) (e.g., PEG-silane conjugate dissolved in a polar aprotic solvent such as, for example, DMSO or DMF), holding the resulting reaction mixture at a time ($t^6$) and temperature ($T^6$) (e.g., ($t^6$) 0.5 minutes to 24 hours at room temperature ($T^6$)) (whereby at least a portion of the PEG-silane conjugate molecules are adsorbed on at least a portion of the surface of the nanoparticles surface functionalized with polyethylene glycol groups comprising a ligand), and heating the resulting mixture from at a time ($t^7$) and temperature ($T^7$) (e.g., ($t^7$) 1 hour to 24 hours at 40° C. to 100° C. ($T^7$)), whereby nanoparticles surface functionalized with polyethylene glycol groups and polyethylene glycol groups comprising a ligand are formed.

In another example, at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with polyethylene glycol groups having a reactive group, and, optionally, polyethylene glycol groups. Optionally, polyethylene glycol groups are reacted with a second ligand (which can be the same or different than the ligand of the nanoparticles surface functionalized with polyethylene glycol groups and polyethylene glycol group comprising a ligand) functionalized with a second reactive group (which can be the same or different than the reactive group of the nanoparticles surface functionalized with polyethylene glycol groups and polyethylene glycol group comprising a ligand) thereby forming nanoparticles surface functionalized with polyethylene groups functionalized with a second ligand and, optionally, polyethylene glycol groups.

In another example, at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with polyethylene glycol groups and, optionally having a reactive group, and, optionally, polyethylene glycol groups, are reacted with a second ligand (which can be the same or different than the ligand of the nanoparticles surface functionalized with polyethylene glycol groups and polyethylene glycol group comprising a ligand) functionalized with a second reactive group (which can be the same or different than the reactive group of the nanoparticles surface functionalized with polyethylene glycol groups and polyethylene glycol group comprising a ligand) thereby forming nanoparticles surface functionalized with polyethylene groups functionalized with a second ligand and, optionally, polyethylene glycol groups, where at least a portion of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with polyethylene glycol groups having a reactive group, nanoparticles surface functionalized with polyethylene glycol groups having a reactive group and polyethylene glycol groups comprising a ligand the reactive group are reacted with a second ligand functionalized with a reactive group (which can be the same or different than the ligand of the nanoparticles surface functionalized with polyethylene glycol groups and polyethylene glycol group comprising a ligand) thereby forming nanoparticles surface functionalized with polyethylene glycol groups and polyethylene groups functionalized with a second ligand, nanoparticles surface functionalized with polyethylene glycol groups comprising a ligand.

The nanoparticles with PEG groups functionalized with reactive groups can be further functionalized with one or more ligands. For example, a functionalized ligand can be reacted with a reactive group of a PEG group. Examples of suitable reaction chemistries and conditions for post-nanoparticle synthesis functionalization are known in the art.

Nanoparticles with heavy atom(s) and/or heavy atom ion(s) can be formed in various ways. For example, nanoparticles with heavy atom(s) and/or heavy atom ion(s) are formed during PEGylation (e.g, using PEG precursors with heavy atom(s) and/or heavy atom ion(s) or reaction of one or more PEG groups). After PEGylation, nanoparticles can be reacted to form nanoparticles with one or more heavy atom and/or one or more heavy atom ion disposed on at least a portion of a surface of the nanoparticles. In an example, PEGylated nanoparticles are reacted with a heavy metal ions (e.g., a solution comprising heavy metal ions).

The nanoparticles can have a narrow size distribution. In various examples, the nanoparticle size distribution (before or after PEGylation), not including extraneous materials such as, for example, unreacted reagents, dust particles/aggregates, or the like is +/−5, 10, 15, or 20% of the average particle size (e.g., longest dimension). The particle size can be determined by methods known in the art. For example, the particle size is determined by TEM, GPS, or DLS. DLS contains systematic deviation and, therefore, the DLS size distribution may not correlate with the size distribution determined by TEM and/or GPS.

In the case of methods carried out using sulfur-atom precursors or heavy-atom precursors, without intending to be bound by any particular theory, it is considered that amount of sulfur atoms or heavy atoms in the nanoparticles correlates to the relative molar amounts of the precursors used in the reaction mixture.

In various aspects, the present disclosure provides uses of nanoparticles and/or compositions of the present disclosure. Non-limiting examples of uses of the nanoparticles and/or compositions of the present disclosure include imaging methods and photodynamic therapy (PDT) methods, and the like.

This disclosure provides methods for imaging biological materials, such as, for example, cells, extracellular components, or tissues comprising contacting the biological material with nanoparticles comprising one or more dyes, or compositions comprising the nanoparticles; directing excitation electromagnetic (e/m) radiation, such as light, on to the tissues or cells thereby exciting the dye molecules; detecting e/m radiation emitted by the excited dye molecules; and capturing and processing the detected e/m radiation to provide one or more images of the biological material. One or more steps of the method can be carried out in vitro or in vivo. For example, the cells or tissues can be present in an individual or can be present in culture. Exposure of cells or tissues to e/m radiation can be effected in vitro (e.g., under culture conditions) or can be effected in vivo. For directing e/m radiation at cells, extracellular materials, tissues, organs and the like within an individual or any portion of an individual's body that are not easily accessible, fiber optical instruments can be used. See, e.g, FIG. 1.

Since the fluorescent nanoparticles are brighter than free dye, fluorescent particles can be used, for example, for tissue imaging and tumor (e.g., metastatic tumor) imaging. Additionally or alternatively, radioisotopes can be further attached to the ligand groups (e.g., tyrosine residue, chelator, and the like) of the ligand-functionalized nanoparticles or to the silica matrix of the PEGylated nanoparticles without specific ligand functionalization for photoinduced electron transfer imaging. If the radioisotopes are chosen to be therapeutic, such as, for example, $^{225}$Ac or $^{177}$Lu, this in turn would result in nanoparticles with additional radiotherapeutic properties.

In an example, a method of obtaining an image of a sample comprising a biological material comprises: contacting the sample (e.g., the individual) with a nanoparticle of the present disclosure; irradiating the sample (e.g., individual or a portion thereof); and obtaining a fluorescence image of the sample (e.g., the individual or a portion thereof).

In another example, a method for imaging of a region within an individual comprises (a) administering to the individual nanoparticles or a composition of the present disclosure comprising one or more dye molecules; (b) irradiating the individual or a portion thereof with electromagnetic radiation (e.g., directing electromagnetic radiation, which may be referred to as, excitation light into the individual), thereby exciting at least one of the one or more dye molecules; and obtaining a fluorescent image of the region within the individual (e.g., (c) detecting excited light, the detected light having been emitted by the one or more dye molecules in the individual as a result of excitation by the excitation light; and (d) processing signals corresponding to the detected light to provide one or more images (e.g., a real-time video stream) of the region within the individual).

A fluorescent image can be obtained in various ways. For example, obtaining a fluorescence image comprises: detecting excited electromagnetic radiation, the detected electromagnetic radiation having been emitted by the dye molecules in the individual as a result of excitation by the excitation electromagnetic radiation; and processing signals corresponding to the detected electromagnetic radiation to provide one or more images of the region within the individual.

Imaging methods of the present disclosure can provide sub-diffraction limit resolution. The imaging methods can be referred to as super-resolution (SR) imaging methods. In various examples, an imaging method provides (e.g., exhibits) sub-diffraction limit resolution, where the diffraction limit is $\lambda/2$ and $\lambda$ is the wavelength of the excitation light. In various examples, an imaging method provides (e.g., exhibits) a resolution 10% or less, 20% or less, or 50% or less than the diffraction limit.

A composition of the present disclosure does not require reducing agents as additives to an imaging buffer to provide sub-diffraction limit resolution. Accordingly, in an example, a composition used in an imaging method does not comprise an imaging buffer. Examples of imaging buffers are known in the art. Non-limiting examples of imaging buffers include a mixture of 2-mercaptoethanol and enzymatic oxygen scavenger system (e.g., glucose oxidase/catalase system) in phosphate-buffered saline (PBS). In an example, a composition used in an imaging method of the present disclosure does not comprise 2-mercaptoethanol or the like.

Various imaging methods can be carried out using methods of the present disclosure. Non-limiting examples of imaging methods include ground state depletion (GSD) microscopy, stochastic optical reconstruction microscopy (STORM), direct stochastic optical reconstruction microscopy (dSTORM), stimulated emission and depletion (STED), photoactivated localization microscopy (PALM), and the like.

Nanoparticle(s) or composition(s) of the present disclosure can be used in various PDT methods. In various examples, a photodynamic therapy method (e.g., a method for treating cancer in an individual) comprises: administering to an individual (e.g., an individual with abnormal cells such as, for example, cancer cells) with a nanoparticle of the present disclosure or a composition of the present disclosure; and irradiating the individual (e.g., the abnormal cells of the individual and, optionally, the surrounding tissue) or a portion thereof (e.g., directing electromagnetic radiation into the individual (e.g., the abnormal cells of the individual and, optionally, the surrounding tissue) or a portion thereof) with electromagnetic radiation having a wavelength of 400 to 900 or 400 to 800 nm (e.g., one or more wavelengths that form at least one triplet state nanoparticle—dye of the nanoparticle—that can form a reactive ion species, for example, on energy transfer to an oxygen molecule or other oxygen containing species), wherein the irradiation results in formation of a reactive ion species (e.g., singlet oxygen) that inhibit the growth of and/or kill at least a portion of or all of the abnormal cells.

A PDT method may further comprise visualization of the cancer after administration of the nanoparticle or the composition. In an example, the visualization is carried using fluorescence imaging.

Compositions comprising the present nanoparticles can be administered to an individual by any suitable route—either alone or as in combination with other agents. Administration can be accomplished by any means, such as, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Transdermal delivery can include delivery via the use of dermal patches.

Following administration of a composition comprising the present nanoparticles, the path, location, and clearance of the NPs can be monitored using one or more imaging techniques. Examples of suitable imaging techniques are described herein.

In certain cases, combination therapy (PDT+chemotheapy) may reduce symptoms and prolong the life of patients significantly. This approach can be useful in treating patients with advanced cancers that are not suitable for surgery radiation therapy (e.g., patients with small cell lung cancer, bladder cancer, brain cancer, head and/or neck cancer esophageal cancer that cannot be completely removed by surgery).

In various examples, a method further comprises administering to the patient an additional cancer treatment. In some examples, the additional cancer treatment is selected from the group comprising, surgery, radiotherapy, chemotherapy, toxin therapy, immunotherapy, cryotherapy, gene therapy, and combinations thereof.

In an example, a PDT method further comprises administration of a chemotherapy agent. In various examples, a chemotherapy agent is a drug or drug formulation. Non-limiting examples of drug formulations include polymeric micelle formulations, liposomal formulations, dendrimer formulations, polymer-based nanoparticle formulations, silica-based nanoparticle formulations, nanoscale coordination polymer formulations, nanoscale metal-organic framework formulations, inorganic nanoparticle formulations, and the like.

Various chemotherapy agents (e.g., chemotherapy drugs) can be used. Any FDA approved chemotherapy agent (e.g., chemotherapy drugs) can be used. Combinations of chemotherapy agents can be used.

The administrations and irradiation can be carried out in various ways and in various orders. Typically, administration(s) of the nanoparticle(s) or composition(s) is/are carried out first, and, subsequently, the chemotherapy agent(s) is/are is administered. The irradiation is carried out after administration of the nanoparticle(s) or composition(s) and before administration of the chemotherapy agent(s) or after administration of both the nanoparticle(s) or composition(s) and chemotherapy agent(s). In an example, the administration comprises i) administration of the nanoparticle(s) and/or composition(s), and ii) after completion of the administration of the nanoparticle(s) and/or composition(s) and irradiation of the individual, administration of the chemotherapy agent.

In an example, the chemotherapy agent is administered (e.g., administration initiated) after administration (e.g., first administration) of the nanoparticle(s) or composition(s) or after administration (e.g., first administration) of the nanoparticle(s) or composition(s) and irradiation.

Without intending to be bound by any particular theory, it is considered that the irradiation causes a response (e.g., photodynamic therapy response) in the individual. "Irradiating" and "irradiation" as used herein includes exposing an individual to a selected wavelength or wavelengths of light. It is desirable that the irradiating wavelength is selected to match the wavelength(s) which excite the nanoparticle(s) (e.g., nanoparticle(s) of the composition(s). It is desirable that the radiation wavelength(s) matches the excitation wavelength(s) of the nanoparticle(s) and has low absorption by the non-target tissues of the individual.

Irradiation is further defined herein by its coherence (laser) or non-coherence (non-laser), as well as intensity, duration, and timing with respect to dosing using the nanoparticle(s) or composition(s) of the present disclosure. The intensity or fluence rate must be sufficient for the light to reach the target tissue. The duration or total fluence dose must be sufficient to photoactivate enough of the nanoparticle(s) or composition(s) to act on the target tissue. Timing with respect to dosing of the nanoparticle(s) or composition(s) may be important, because 1) the administered the nanoparticle(s) or composition(s) may require time to home in on target tissue and 2) the blood level of the nanoparticle(s) or composition(s) may decrease with time. The radiation energy is provided by an energy source, such as a laser or cold cathode light source, that is external to the individual, or that is implanted in the individual, or that is introduced into an individual, such as by a catheter, optical fiber or by ingesting the light source in capsule or pill form (e.g., as disclosed in U.S. Pat. No. 6,273,904 (2001), the disclosure of which with regard to radiation energy is incorporated herein by reference).

A method of the present disclosure can be used to treat an individual with (e.g., diagnosed with) cancer. The treatment can have various results. In various examples, a method of the present disclosure results in at least one or more of the following: complete cure of the individual, remission, increased long-term survival of the individual, or reduced tumor volume.

Methods of the present disclosure can be used on various individuals. In various examples, an individual is a human or non-human mammal. Examples of non-human mammals include, but are not limited to, farm animals, such as, for example, cows, hogs, sheep, and the like, as well as pet or sport animals such as horses, dogs, cats, and the like. Additional non-limiting examples of individuals include rabbits, rats, mice, and the like. The nanoparticles or compositions comprising nanoparticles can be administered to individuals for example, in pharmaceutically-acceptable carriers, which facilitate transporting the nanoparticles from one organ or portion of the body to another organ or portion of the body.

A method may also comprise visualization of the abnormal cells (e.g., cancer cells) (e.g., visualization of one or more tumors) after administration of the nanoparticle(s) or composition(s) of the present disclosure. The visualization (e.g., fluorescence imaging) can be used to determine personalized treatment for an individual. For example, visualization is carried using fluorescence imaging (e.g., fluorescence imaging of the present disclosure). A method may further comprise further comprise surgical intervention (e.g., surgical removal of at least a portion of or all of a cancerous tissue from the individual). The surgical removal can be guided by the visualization (e.g., fluorescence imaging).

In imaging methods, it may be desirable to use sulfur-containing nanoparticle(s) or composition(s) comprising sulfur-containing nanoparticle(s) with fluorescent dye(s) or heavy atom-containing nanoparticle(s) or composition(s) comprising heavy atom-containing nanoparticle(s) with fluorescent dye(s). In PDT methods, it is desirable to use nanoparticle(s) or composition(s) with non-fluorescent dye(s) that on irradiation (e.g., excitation) populate triplet states, which in turn will lead to triplet to singlet transitions in oxygen, which then kills cells.

Methods of the present disclosure can be used to treat various cancers (e.g., a tumor or tumors related to a cancer). Non-limiting examples of cancers include lung cancer, colon cancer, melanoma, head and/or neck cancer, esophageal cancer, laryngeal cancer, breast cancer, pancreatic cancer, renal cancer, bladder cancer, ovarian cancer, prostate cancer, testicular cancer, and the like, and combinations thereof.

In an aspect, the present disclosure provides kits. A kit comprises one of more nanoparticle and/or one or more composition of the present disclosure. The composition(s) may be pharmaceutical compositions.

In an example, a kit comprises one or more nanoparticle of the present disclosure and/or one or more composition of the present disclosure, and instructions for use of the nanoparticle(s) and/or composition(s) for treatment of (e.g., administration to) an individual.

In an example, a kit is or comprises a closed or sealed package that contains the nanoparticle(s) and/or composition(s). In certain examples, the package comprises one or more closed or sealed vials, bottles, blister (bubble) packs, or any other suitable packaging for the sale, or distribution, or use of the nanoparticle(s) and/or composition(s). The printed material can include printed information. The printed information can be provided on a label, or on a paper insert, or printed on the packaging material itself. The printed information can include information that identifies the compound in the package, the amounts and types of other active and/or inactive ingredients, and instructions for taking the composition, such as the number of doses to take over a given period of time, and/or information directed to a pharmacist and/or another health care provider, such as a physician, or a patient. The printed material can include an indication that the pharmaceutical composition and/or any other agent provided with it is for treatment of cancer and/or any disorder associated with cancer. In examples, the kit includes a label describing the contents of the container and providing indications and/or instructions regarding use of the contents of the kit to treat any cancer.

The steps of the methods described in the various embodiments and examples disclosed herein are sufficient to carry out the methods of the present disclosure. Thus, in an example, a method consists essentially of a combination of steps of the methods disclosed herein. In another example, a method consists of such steps.

The following Statements provide examples of sulfur- or heavy atom-containing silica or aluminosilica nanoparticles of the present disclosure, methods of making such nanoparticles, and uses thereof.

Statement 1. A silica or aluminosilicate nanoparticle comprising: 0-90 at. % (relative to Si) (e.g., 10-80 and 30-60 at. % (relative to Si)) sulfur atoms covalently bonded to the silica network of the silica nanoparticle or the aluminosilicate network of the aluminosilicate nanoparticle, at least one organic dye (e.g., fluorescent dye, non-fluorescent dye, or fluorescent protein) (e.g., a group derived from an organic dye molecule) (e.g., 1, 2, 3, 4 or 5 dyes) covalently bonded to the silica network of the silica nanoparticle or the aluminosilicate network of the aluminosilicate nanoparticle, and the nanoparticle has a longest dimension of less than 10 nm (e.g., 0.01-9.99 nm, including all 0.01 nm values and ranges therebetween).

Statement 2. A silica or aluminosilicate nanoparticle comprising: 0-20 at. % (relative to Si) heavy atoms (e.g., 1-20 at. % (relative to Si) and 1-10 at. % (relative to Si)), at least one fluorescent dye molecule (e.g., 1, 2, 3, 4, or 5 dye molecules) covalently bonded thereto, and the nanoparticle has a longest dimension of less than 10 nm (e.g., 0.01-9.99 nm, including 0.01 nm values and ranges therebetween).

Statement 3. A silica or aluminosilicate nanoparticle of Statement 2, covalently bonded or non-covalently bound to the silica network of the silica nanoparticle or aluminosilicate network of the aluminosilicate nanoparticle and/or chelated to at least a portion of the surface of the silica nanoparticle or aluminosilicate nanoparticle.

Statement 4. A silica or aluminosilicate nanoparticle of Statement 3, where the heavy atoms are selected from the group consisting of iodine atoms, bromine atoms, or a combination thereof covalently bonded to the silica network of the silica nanoparticle or aluminosilicate network of the aluminosilicate nanoparticle and metal ions (e.g., Au ions, Ag ions, Pb ions, Ti ions, Bi ions, Pt ions, In ions, Sn ions, Sb ions, Pd ions, and the like) non-covalently bound (e.g., chelated) to the silica network of the silica nanoparticle or aluminosilicate network of the aluminosilicate nanoparticle and/or non-covalently bound (e.g., chelated) to at least a portion of the surface of the silica nanoparticle or aluminosilicate nanoparticle, and combinations thereof.

Statement 5. A silica or aluminosilicate nanoparticle of any one of the preceding Statements, where the dye is a fluorescent dye selected from the group consisting of cyanine dyes (e.g., Cy5®, Cy3®, Cy5.5®, Cy7®, and the like), carborhodamine dyes (e.g., ATTO 647N (available from ATTO-TEC and Sigma Aldrich®), BODIPY dyes (e.g. BODIPY 650/665), Xanthene Dyes (e.g. fluorescein (e.g. FITC, Rose bengal), eosins (e.g. Eosin Y), and rhodamines (e.g. TAN/IRA, TMR, TRITC, DyLight 633, Alexa 633, HiLyte 594)), or a group derived therefrom, or a combination thereof and/or a non-fluorescent dye (e.g., methylene blue or group derived therefrom).

Statement 6. A silica or aluminosilicate nanoparticle of any one of the preceding Statements, where at least a portion of the exterior surface (e.g., at least 50% of the exterior surface) is functionalized with polyethylene glycol groups.

Statement 7. A silica or aluminosilicate nanoparticle of any one of the preceding Statements, where at least a portion of the exterior surface (e.g., at least 50% of the exterior surface) is functionalized with a ligand.

Statement 8. A silica or aluminosilicate nanoparticle of Statement 7, where the ligand is a biomolecule is selected from the group consisting of biotin, targeting ligands (e.g., targeting peptides such as, for example, cyclic-RGD and derivatives thereof), alpha-MSH and derivatives thereof, targeting antibody fragments, targeting glycans (e.g., sugar molecules targeting cell surface receptors), chelator molecules for radio metals, such as, for example, deferoxamine (DFO), which is an efficient chelators for radio-labeling with, for example, Zr", NODA, DOTA, and drug molecules.

Statement 9. A composition comprising a plurality of nanoparticles of any one of the preceding Statements.

Statement 10. The composition of Statement 9, where the composition further comprises an aqueous medium and the nanoparticles are present as a dispersion in the aqueous medium.

Statement 11. The composition of Statement 9, where the composition further comprises a pharmaceutically acceptable carrier.

Statement 12. A method of making silica or aluminosilicate nanoparticles comprising one or more sulfur atom or one or more heavy atom comprising: a) forming a reaction mixture at room temperature (e.g., 15° C. to 25° C. depending on the location) comprising water, TMOS (a silica-forming precursor) (e.g., at a concentration of 11 mM to 270 mM), optionally, an alumina-forming precursor (e.g., at a concentration of 0.01 mM to 0.1 mM), and, a sulfur-containing precursor (e.g., at a concentration of 9 mM to 250 mM) or a heavy atom-containing precursor (e.g., at a concentration of 1 mM to 300 mM), where, the in case of making aluminosilicate precursors, the pH of the reaction mixture (which can be adjusted using an acid such as, for example, hydrochloric acid) is 0.1 to 2.5 or in the case of silica precursors is the pH of the reaction mixture (which can be adjusted using a base such as, for example, ammonium hydroxide) is 6 to 9 (which results in formation of precursor nanoparticles having an average size (e.g., longest dimension) of, for example, 1 nm to 9 nm, including all 0.01 nm values and ranges therebetween); b) optionally, holding the reaction mixture at a time ($t^1$) and temperature ($T^1$) (e.g., ($t^1$) 0.5 days to 7 days at room temperature to 95° C. ($T^1$)), whereby nanoparticles having an average size (e.g., longest dimension) of less than 10 nm (e.g., 1 to 9.9 nm, including all 0.01 nm values and ranges therebetween) are formed; c) optionally, (PEGylating the nanoparticles by) adding at room temperature to the reaction mixture comprising the nanoparticles b) a PEG-silane conjugate (comprising a PEG moiety covalently bonded to a silane moiety) (e.g., at a concentration of 10 mM to 60 mM) (e.g., PEG-silane conjugate dissolved in a polar aprotic solvent such as, for example, DMSO or DMF) and holding the resulting reaction mixture at a time ($t^2$) and temperature ($T^2$) (e.g., ($t^2$) 0.5 minutes to 24 hours at room temperature ($T^2$)) (whereby at least a portion of the PEG-silane conjugate molecules are adsorbed on at least a portion of the surface of the nanoparticles from b)); and d) heating the mixture from c) at a time ($t^3$) and temperature ($T^3$) (e.g., ($t^3$) 1 hour to 24 hours at 40° C. to 100° C. ($T^3$)), whereby the silica nanoparticles or aluninosilicate nanoparticles surface functionalized with polyethylene glycol groups are formed.

Statement 13. The method of Statement 12, where the reaction mixture further comprises an aluminasilicate-forming precursor and the pH of the reaction mixture is adjusted to a pH of 1 to 2 prior to addition of the alumina-forming precursor, the pH of the solution is adjusted to a pH of 7 to 9 and, optionally, PEG with molecular weight between 0.1 k and 1 k and concentration between 10 mM and 75 mM is added to the reaction mixture right before adjusting a pH of 7 to 9, and the nanoparticle is an aluminosilicate nanoparticle.

Statement 14. The method of any one of Statements 12 or 13, where in the reaction mixture further comprises a dye precursor and the nanoparticles surface functionalized with PEG groups have one or more dye molecules covalently encapsulated therein.

Statement 15. The method of any one of Statements 12-14, where at least a portion of or all of the PEG-silane conjugate comprises a ligand.

Statement 16. The method of Statement 15, where PEG-silane conjugate comprising a ligand is added in addition to PEG-silane in d), whereby nanoparticles surface functionalized with PEG groups and polyethylene groups comprising a ligand are formed.

Statement 17. The method of any one of Statements 12-16, where before or after the PEG-silane conjugate is added in d) a PEG-silane conjugate comprising a ligand is added at room temperature to the reaction mixture comprising the nanoparticles from b), holding the resulting reaction mixture at a time ($t^4$) and temperature ($T^4$), subsequently heating the resulting reaction mixture at a time ($t^5$) and temperature ($T^5$), whereby nanoparticles surface functionalized with PEG groups comprising a ligand are formed, optionally, subsequently adding at room temperature to the resulting reaction mixture comprising nanoparticles surface functionalized with PEG groups comprising a ligand a PEG-silane conjugate, holding the resulting reaction mixture at a time ($t^6$) and temperature ($T^6$) whereby at least a portion of the PEG-silane conjugate molecules are adsorbed on at least a portion of the surface of the nanoparticles surface functionalized with PEG groups comprising a ligand a PEG-silane conjugate, and heating the resulting mixture from at a time ($t^7$) and temperature ($T^7$) whereby nanoparticles surface functionalized with PEG groups and PEG groups comprising a ligand are formed.

Statement 18. The method of any one of Statements 12-17, where at least a portion of or all of the PEG-silane conjugate has a reactive group on a terminus of the PEG moiety opposite the terminus conjugated to the silane moiety of the PEG-silane conjugate and after formation of the nanoparticles surface functionalized with PEG groups having a reactive group, and, optionally, PEG groups, are reacted with a second ligand functionalized with a second reactive group thereby forming nanoparticles surface functionalized with polyethylene groups functionalized with a second ligand and, optionally, PEG groups.

Statement 19. The method of any one of Statements 12-17, where at least a portion of or all of the PEG-silane has a reactive group on a terminus of the PEG moiety opposite the terminus conjugated to the silane moiety of the PEG-silane conjugate and after formation of the nanoparticles surface functionalized with PEG groups and, optionally having a reactive group, and, optionally, PEG groups, are reacted with a second ligand functionalized with a second reactive group thereby forming nanoparticles surface functionalized with polyethylene groups functionalized with a second ligand and, optionally, PEG groups, Statement 20. The method of any one of Statements 12-17, where at least a portion of the PEG-silane has a reactive group on a terminus of the PEG moiety opposite the terminus conjugated to the silane moiety of the PEG-silane conjugate and after formation of the nanoparticles surface functionalized with PEG groups having a reactive group, nanoparticles surface functionalized with PEG groups having a reactive group and PEG groups comprising a ligand are reacted with a second ligand functionalized with a reactive group thereby forming nanoparticles surface functionalized with PEG groups and polyethylene groups functionalized with a second ligand or nanoparticles surface functionalized with PEG groups comprising a ligand.

Statement 21. A method of obtaining an image of a sample or a portion thereof (e.g., of an individual or a portion thereof) comprising: contacting the sample (e.g., the individual) with a nanoparticle of any one of Statements 1-8 or a composition of any one of Statements 9-11; irradiating the sample or a portion thereof (e.g., individual or a portion thereof), thereby exciting at least one of the dye molecules of the nanoparticle or composition; obtaining a fluorescence image of the sample or portion thereof (e.g., the individual or a portion thereof, such as, for example, a region within the individual).

Statement 22. The method of Statement 21, where the obtaining a fluorescence image comprises: detecting excited electromagnetic radiation, the detected electromagnetic radiation having been emitted by the dye molecules in the individual as a result of excitation by the excitation electromagnetic radiation; and processing signals corresponding to the detected electromagnetic radiation to provide one or more images of the sample or portion thereof or the individual or a portion thereof.

Statement 23. The method of any one of Statements 21 or 22, where at least a portion of the fluorescence image exhibits sub-diffraction limit resolution.

Statement 24. The method of any one of Statements 21-23, where the method is ground state depletion (GSD) microscopy, stochastic optical reconstruction microscopy (STORM), direct stochastic optical reconstruction microscopy (dSTORM), stimulated emission and depletion (STED), or photoactivated localization microscopy (PALM).

Statement 25. The method of any one of Statements 21-24, where the contacting is administering the nanoparticle or the composition to an individual.

Statement 26. The method of Statement 25, where the electromagnetic radiation is directed into the individual.

Statement 27. The method of any one of Statements 25 or 26, where the region is within the individual.

Statement 28. The method of any one of Statements 21-27, where at least a portion of the image exhibits sub-diffraction limit resolution.

Statement 29. A photodynamic therapy method (e.g., a method for treating cancer in an individual) comprising: administering to an individual (e.g., an individual with abnormal cells) with a nanoparticle of any one of Statements 1-8 or a composition of any one of Statements 9-11; irradiating the individual (e.g., the abnormal cells of the individual and, optionally, the surrounding tissue) or a portion thereof (e.g., directing electromagnetic radiation into the individual (e.g., the abnormal cells of the individual and, optionally, the surrounding tissue) or a portion thereof) with electromagnetic radiation having a wavelength of 400-900 nm (e.g., one or more wavelengths that form at least one triplet state nanoparticle—dye of the nanoparticle—that can form a reactive ion species, for example, on energy transfer to an oxygen molecule), where the irradiation results in formation of a reactive ion species (e.g., singlet oxygen) that inhibit the growth of and/or kill the abnormal (e.g., cancer) cells.

Statement 30. The method of Statement 29, where the method further comprises visualization of the cancer after administration of the nanoparticle or the composition.

Statement 31. The method of Statement 30, where the visualization is carried out using fluorescence imaging.

Statement 32. The method of any one of Statements 29-31, where the method further comprises administration of a chemotherapy agent.

Statement 33. The method of any one of Statements 29-32, where the method further comprises surgical removal of at least a portion of a cancerous tissue from the individual.

Statement 34. A kit comprising one or more nanoparticle of nanoparticle of any one of Statements 1-8 and/or one or more composition of any one of Statements 9-11, and instructions for use of the nanoparticle(s) and/or composition(s) for treatment of an individual.

The following example is presented to illustrate the present disclosure. It is not intended to limiting in any matter.

EXAMPLE

This example provides a description of nanoparticles of the present disclosure, and making and characterization of the nanoparticles.

Ultrasmall Silica Nanoparticles for Super-Resolution Optical Microscopy and Photodynamic Therapy. Super-resolution fluorescence microscopy has revolutionized optical imaging in the life sciences. Resolution rests on the ability of fluorescent markers to enter transient dark states. For organic fluorophores this often requires imaging buffers interfering with biological function. In this example, the concept of particle molecular photo-engineering was used to tailor the precise chemical environment around covalently bonded dyes inside ultrasmall fluorescent silica nanoparticles. We engineered bright photoswitchable nanoprobes embedding cyanine dyes, functionalizing the silica network with mercaptopropyl groups, and demonstrating stochastic optical reconstruction microscopy without the use of toxic β-mercaptoethanol. We employed iodopropyl groups for quantum mechanical spin-orbit coupling to control triplet state populations of encapsulated carborhodamine dye ATTO647N and methylene blue derivate MB2, important for ground state depletion microscopy and photodynamic therapy, respectively. It is expected that this concept will be applicable to other dyes, chemistries, and nanoprobes, and the resulting ultraefficient optical labels to facilitate minimally invasive super-resolution life cell imaging and therapeutic effects.

In this example, a general strategy for tailoring the photo-properties of ultrasmall (<10 nm) silica NPs and aluminosilicate NPs, approaching near FP sizes. This is achieved through particle molecular photo-engineering (PMPE), co-localizing and covalently enclosing sulfur atoms and iodine atoms and organic fluorophores within a sub-10 nm and polyethylene glycol (PEG) surface functionalized and stabilized NPs, with particular emphasis on enabling stochastic SR microscopy (FIGS. 1b and 1c). This approach combines the benefits of silica, i.e. size-independent bright dye emissive properties, biocompatibility, optical transparency, and multifunctionality, while avoiding disadvantages of imaging cocktails, i.e. interference with biological function and unpleasant odor of mercapto compounds.

Figure 2:
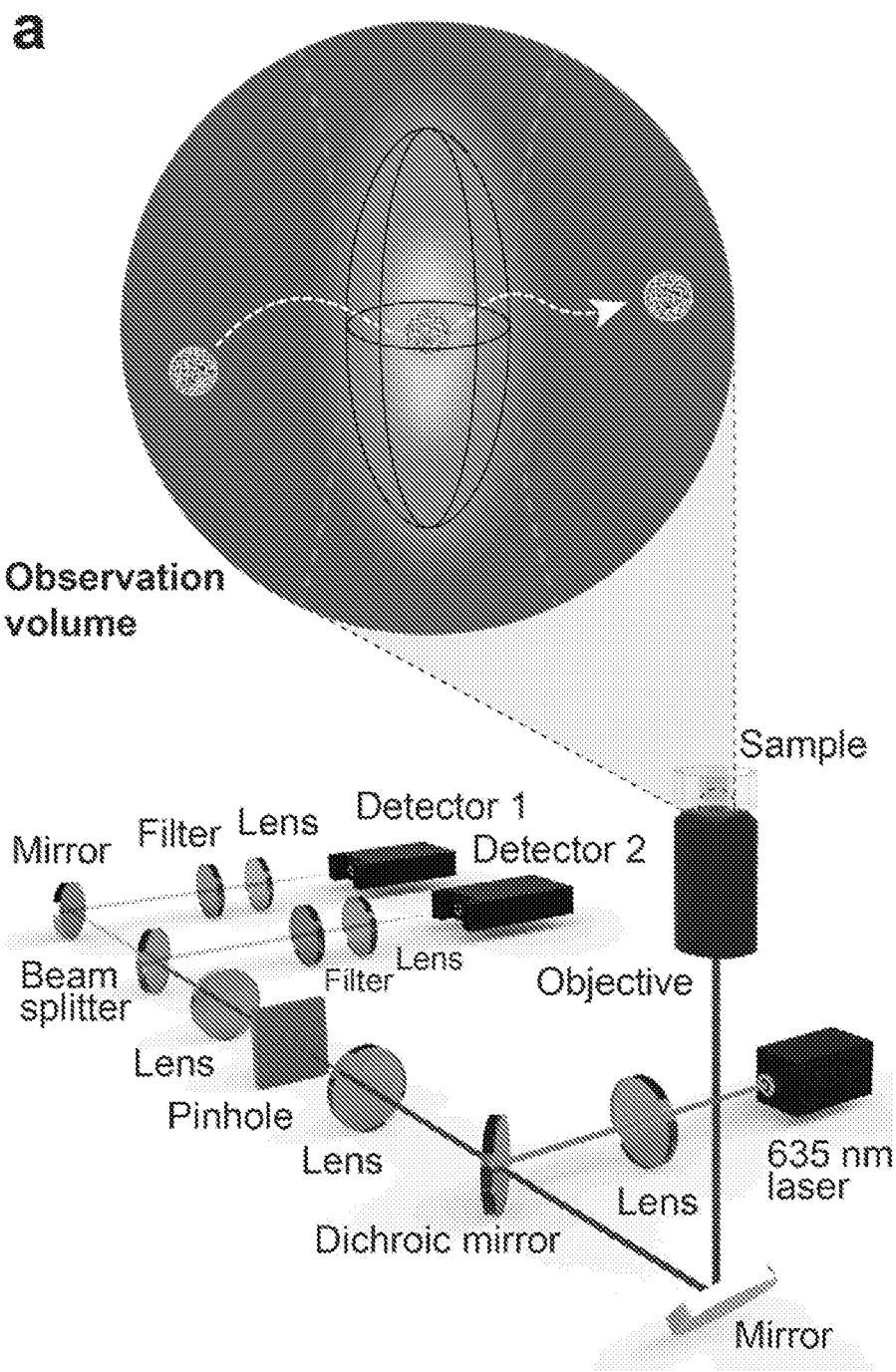
FIG. 2 shows materials characterization. (a) Fluorescence correlation spectroscopy (FCS) setup. A laser is focused into an aqueous solution above an objective, forming an observation volume. The fluorescence signal from particles diffusing trough the observation volume is split detected by two avalanche photo diode (APD) detectors to suppress afterpulsing effects. (b) Normalized FCS autocorrelation curves of free Cy5 dye and various 25 min srC' dots with increasing thiol content (0%, 30%, 60%, and 80%). Corresponding fits used a correlation function with translational diffusion, cis-trans isomerization, and rotational diffusion components. (c) Corresponding intensity-matched absorption (left axis) and emission spectra (right axis) from 645 nm excitation. (d) Solid-state 29Si CP/MAS NMR spectra of srC' dots (0%, 30%, and 60%) showing T- and Q-group assignments with structural illustrations. (e) Solid-state 27Al MAS NMR spectra of srC' dots (0%, 30%, and 60%) with assignments to four- and six-fold coordinated aluminum. f, Solid-state 13C CP/MAS NMR spectra of srC' dots (0%, 30%, and 60%) with peak assignments to carbons from PEG-silane, mercaptopropyl, and disulfide groups. The peak of 5" carbon at 22 ppm is only partially visible as a high-field shoulder of the 3 carbon peak.
Figure 2:
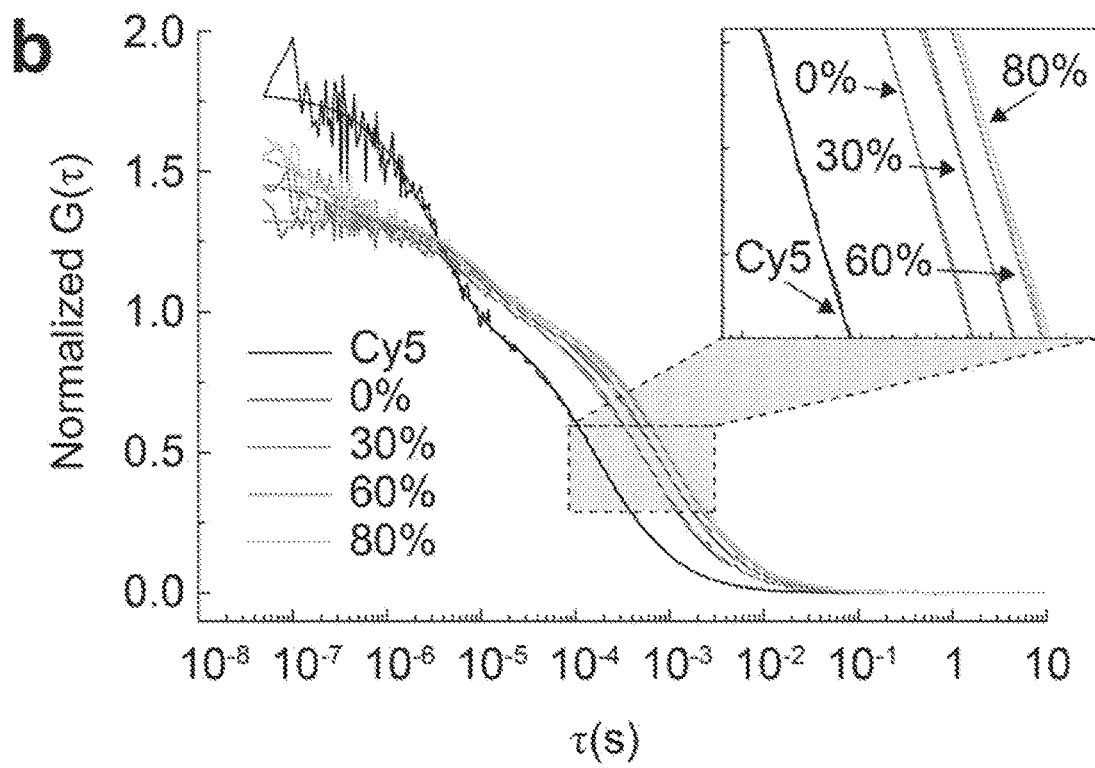
Figure 2:
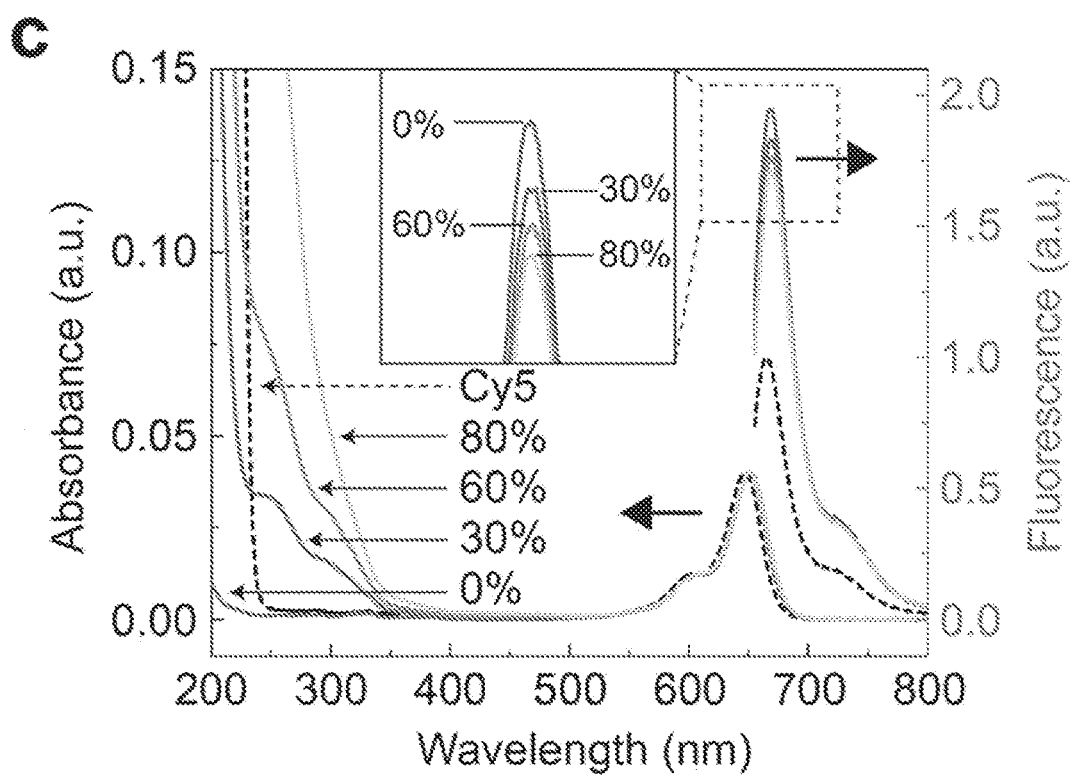
Figure 2:
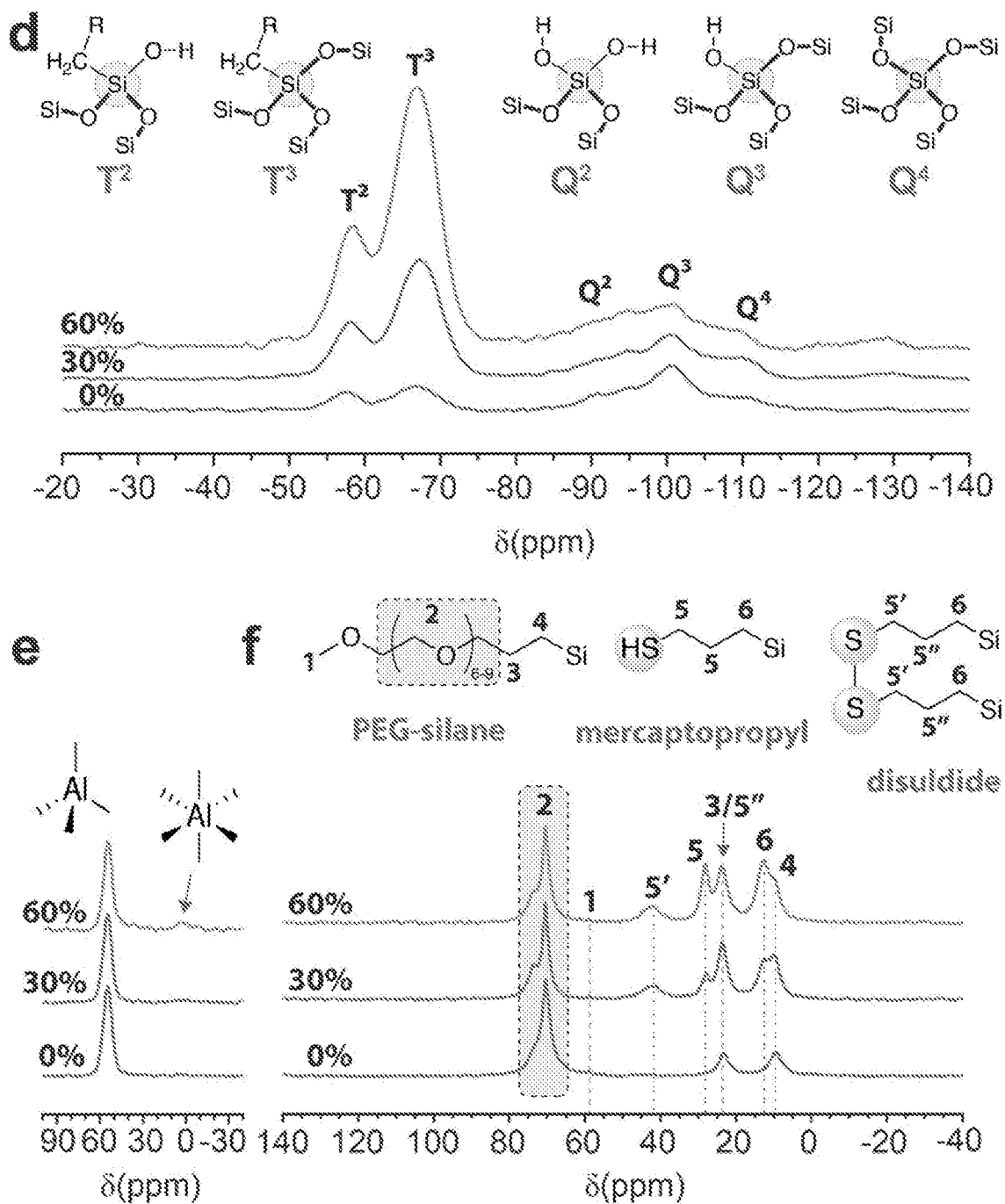

To vary the chemical composition of photoswitchable sub-10 nm SNPs, we utilized a growth quenching mechanism in aqueous solution. Four different super-resolution Cornell prime dots (srC' dots) were synthesized with varying relative precursor molar ratios of (3-mercaptopropyl) trimethoxysilane (MPTMS) and tetramethylorthosilicate (TMOS): 3:7 (30% srC' dots), 6:4 (60% srC' dots) and 8:2 (80% srC' dots), as well as a negative control particle with no MPTMS (0% srC' dots). Particles were characterized by fluorescence correlation spectroscopy (FCS), and particle concentration and hydrodynamic diameter, $d_{sample}$, determined from fits using a model accounting for translational diffusion, photoinduced cis-trans isomerization, and rotational diffusion (equations 1 and 2). FIG. 2b shows FCS results with fits measured by the setup shown in FIG. 2a for free Cy5 dye and srC' dots derived from different MPTMS to TMOS ratios providing the following diameters: $d_{Cy5}$=1.3 nm, $d_{0\%srC'dots}$=4.1 nm, $d_{30\%srC'dots}$=5.8 nm, $d_{60\%srC'dots}$=7.2 nm, $d_{80\%srC'dots}$=7.7 nm. By comparing the concentration of particles as measured by FCS with the fluorophore concentration as measured by absorption spectroscopy, we determined the number of dyes per particle, n (equation 3), as: $n_{Cy5}$=1.0, $n_{0\%srC'dots}$=1.2, $n_{30\%srC'dots}$=1.1, $n_{60\%srC'dots}$=1.1, $n_{80\%srC'dots}$=1.2.

Figure 7:
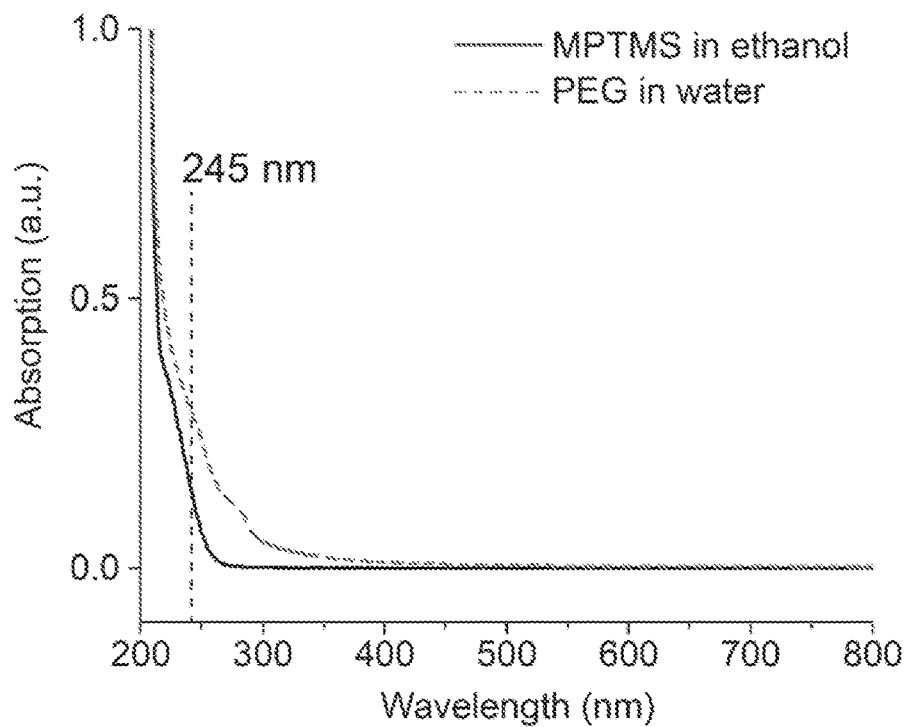
FIG. 7 shows UV-vis spectra of the precursor (3-mercaptopropyl) trimethoxysilane (MPTMS) in ethanol and polyethylene glycol (PEG) in water.
Figure 8:
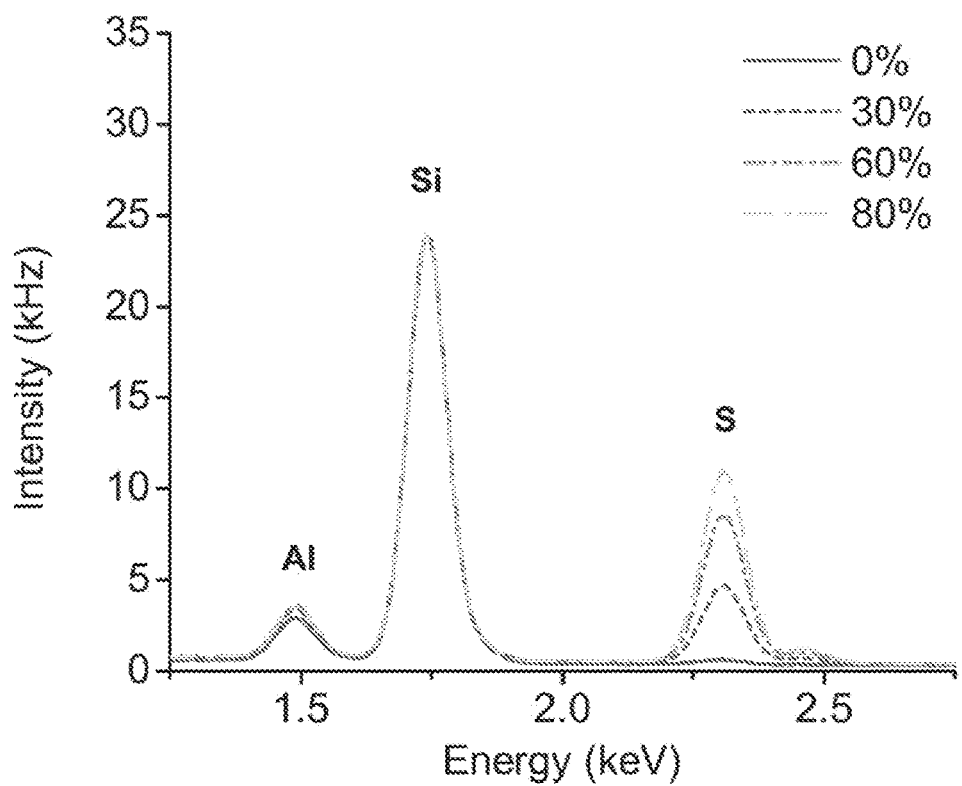
FIG. 8 shows EDS spectra of srC' dots. EDS spectra of the 0%, 30%, 60%, and 80% srC' dots with peak assignments for aluminum (Al), silicon (Si), and sulfur (S).

FIG. 2c shows intensity-matched UV-vis spectra and fluorescence emission spectra of srC' dots as compared to free Cy5 dye, in deionized water at pH 7. In contrast to free dye and 0% srC' dots, all other srC' dots exhibit an additional absorption peak emerging around 245 nm and a shoulder around 300 nm. While the peak at 245 nm is likely a combination of the absorption of mercaptopropyl groups and PEG (FIG. 7), the shoulder around 310 nm suggests a Cy5-thiol adduct. This adduct has been described in detail, and is a result of thiol binding to the polymethine bridge of Cy5. All particles showed a minor bathochromic shift of Cy5 absorption and emission peaks, and a per dye fluorescence quantum enhancement expected from encapsulation into a rigid host silica matrix, leading to an increase in radiative rate, kr, a decrease in non-radiative rate, knr, or both. The largest per dye quantum enhancement of 1.9 is observed for the control particle (0% srC' dots), and decreased slightly to 1.7 with increasing MPTMS/TMOS molar ratio (FIG. 2c). This is consistent with an expected reduction in aluminosilicate network density with increasing MPTMS precursor amount, which due to the silicon-carbon bond, upon condensation can only form three bridging oxygens (T groups) to neighboring silicon as compared to four (Q groups) in case of TMOS (FIG. 2d).

To investigate the detailed local aluminosilicate network structure, we performed $^{29}$Si, $^{27}$Al, and $^{13}$C solid state NMR (ssNMR) experiments on three particles: A 0% srC' dot control and two (30% and 60%) srC' dot samples. $^{29}$Si ssNMR results (FIG. 2d) were consistent with increasing incorporation of MPTMS lowering the silica network density (increasing T versus Q group signals), corroborated by energy-dispersive X-ray spectroscopy (EDS, Figure S2). $^{27}$Al ssNMR spectra (FIG. 2e) primarily exhibited four-fold (tetrahedrally) coordinated aluminum most likely replacing silicon in the silica network. Finally, solid-state CP/MAS $^{13}$C NMR measurements (FIG. 2f) confirmed successful PEGylation of the srC' dots and revealed that the majority of sulfur-containing groups are mercaptopropyl groups, but also suggested oxidative formation of disulfide bonds during synthesis.

Figure 3:
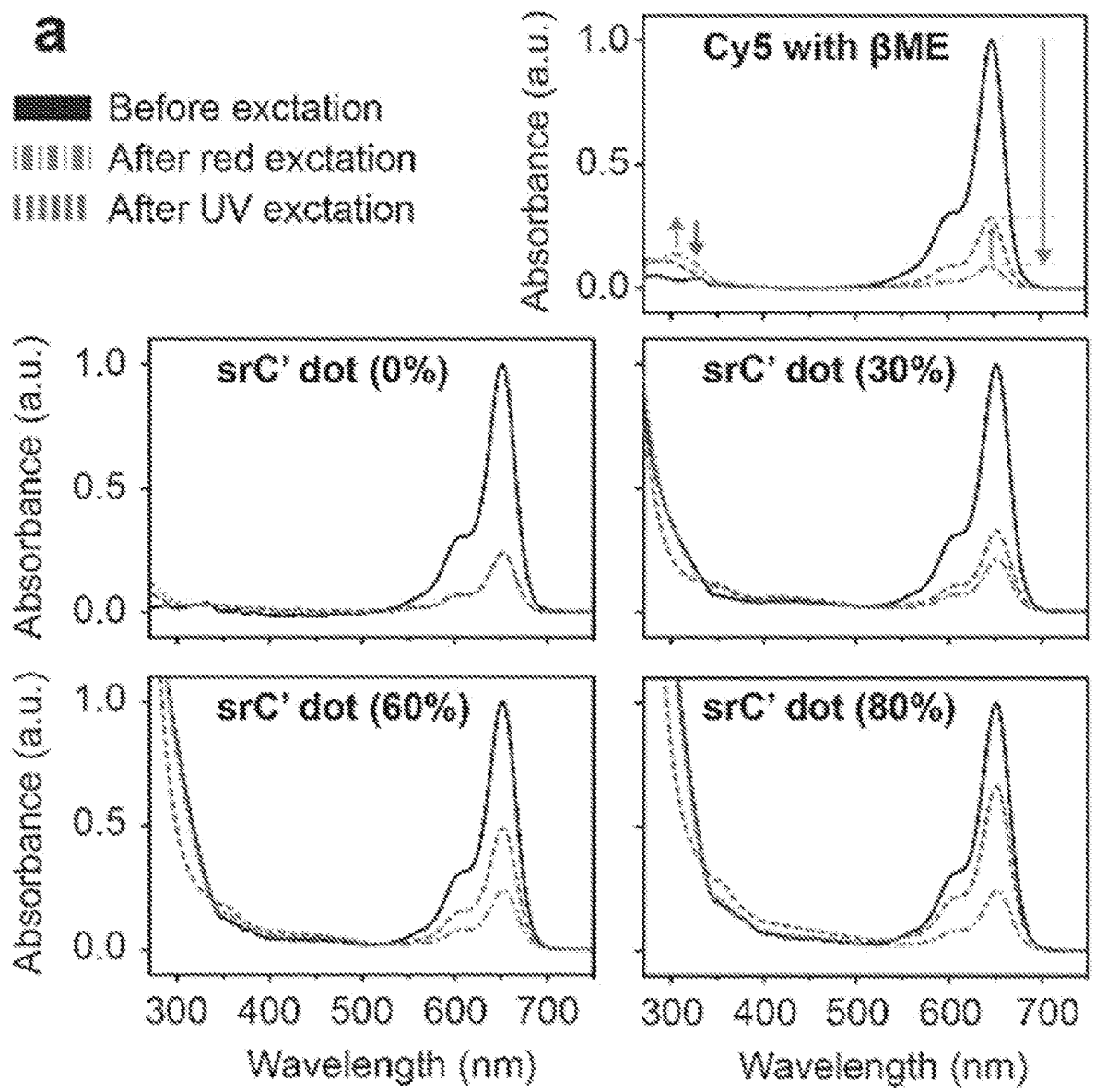
FIG. 3 shows photo-physical behavior of srC' dots. (a) Photoswitching absorption spectra, before excitation, after 30 min red light, and 5 min UV light exposure, of Cy5 in DI water in the presence of (WE and different srC' dots (0%, 30%, 60%, and 80%) in the absence of (ME. (b to e) Single molecule and single particle fluorescence traces recorded for different imaging buffer conditions with insets highlighting short time behavior. Lines refer to three different fluorophores or particles. (f to i) Photon histograms of different dyes and particles for different imaging buffer conditions (as indicated).
Figure 3:
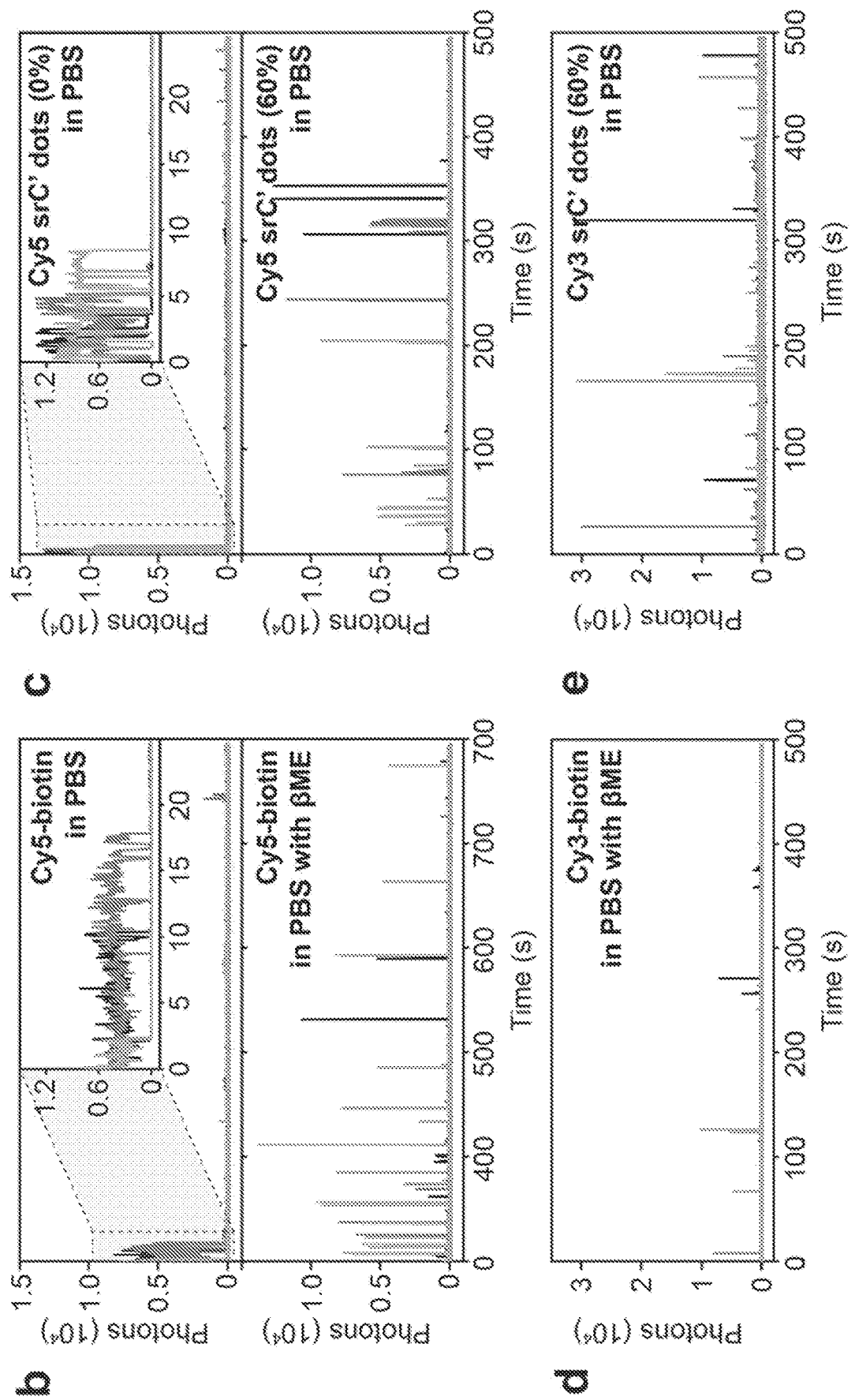
Figure 3:
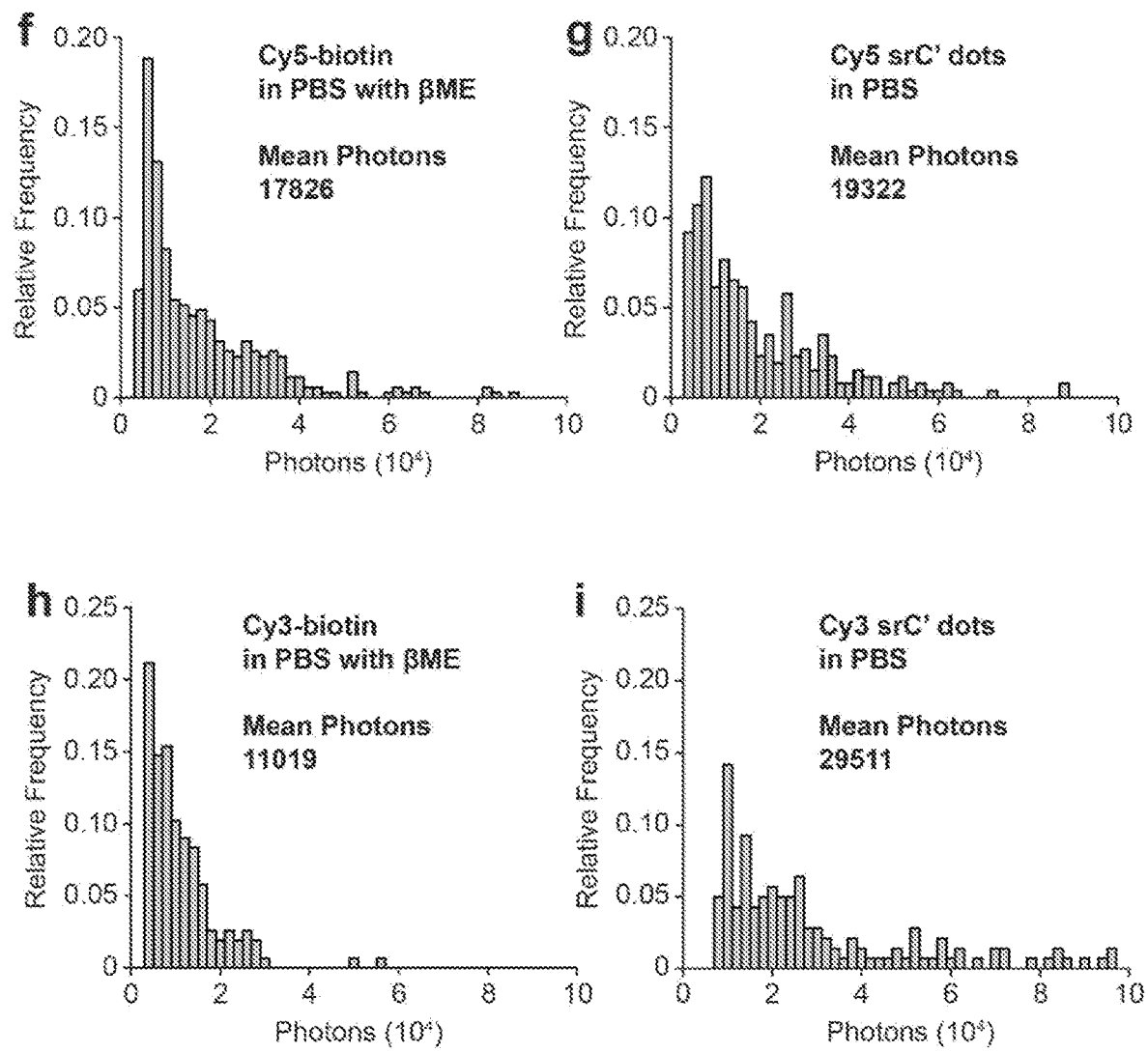

We investigated size tunability of same composition (60%) srC' dots by quenching particle growth via PEG-silane addition at different reaction times (Figure S3) enabling particle hydrodynamic diameters below 7 nm critical e.g. for renal clearance in earlier translation of Cornell dots into human clinical trials. We compared ensemble photoswitching behavior of srC' dots to free Cy5 dye. The Cy5-thiol adduct dissociates upon UV light irradiation (FIG. 1b), leading to reduction of the 310 nm band and recovery of the Cy5 absorption band. FIG. 3a shows the results for free Cy5 dye in the presence of 140 mM of β-mercaptoethanol (βME), a key ingredient of SR imaging cocktails, as well as for 0%, 30%, 60%, and 80% srC' dots without βME. Upon illumination at 633 nm of free Cy5 dye with βME, substantial decrease of the main 647 nm absorption peak is observed and a shoulder at 310 nm emerges, while under exposure to 300 nm light the 647 nm peak partially recovers, all in agreement with previous observations. Using our 0% control particle, under the same conditions but without βME, the 647 nm peak also substantially decreases, but no significant peak at 310 nm is detected. The main 647 nm peak cannot be recovered, but instead further decreases slightly under 300 nm light indicating photo-bleaching. The thiol containing srC' dots without βME also show the decrease of the 647 nm peak and unchanged shoulder at ~310 nm. However, under 300 nm UV exposure the shoulder absorption decreases and the main peak at 647 nm partially recovers, similar to the Cy5 solution with βME. The extend of recovery increases with increasing thiol content surpassing that of free dye, suggesting that the mercapto-enriched silica matrix can give rise to Cy5-thiol adducts either during the synthesis or upon 633 nm illumination or both.

Figure 10:
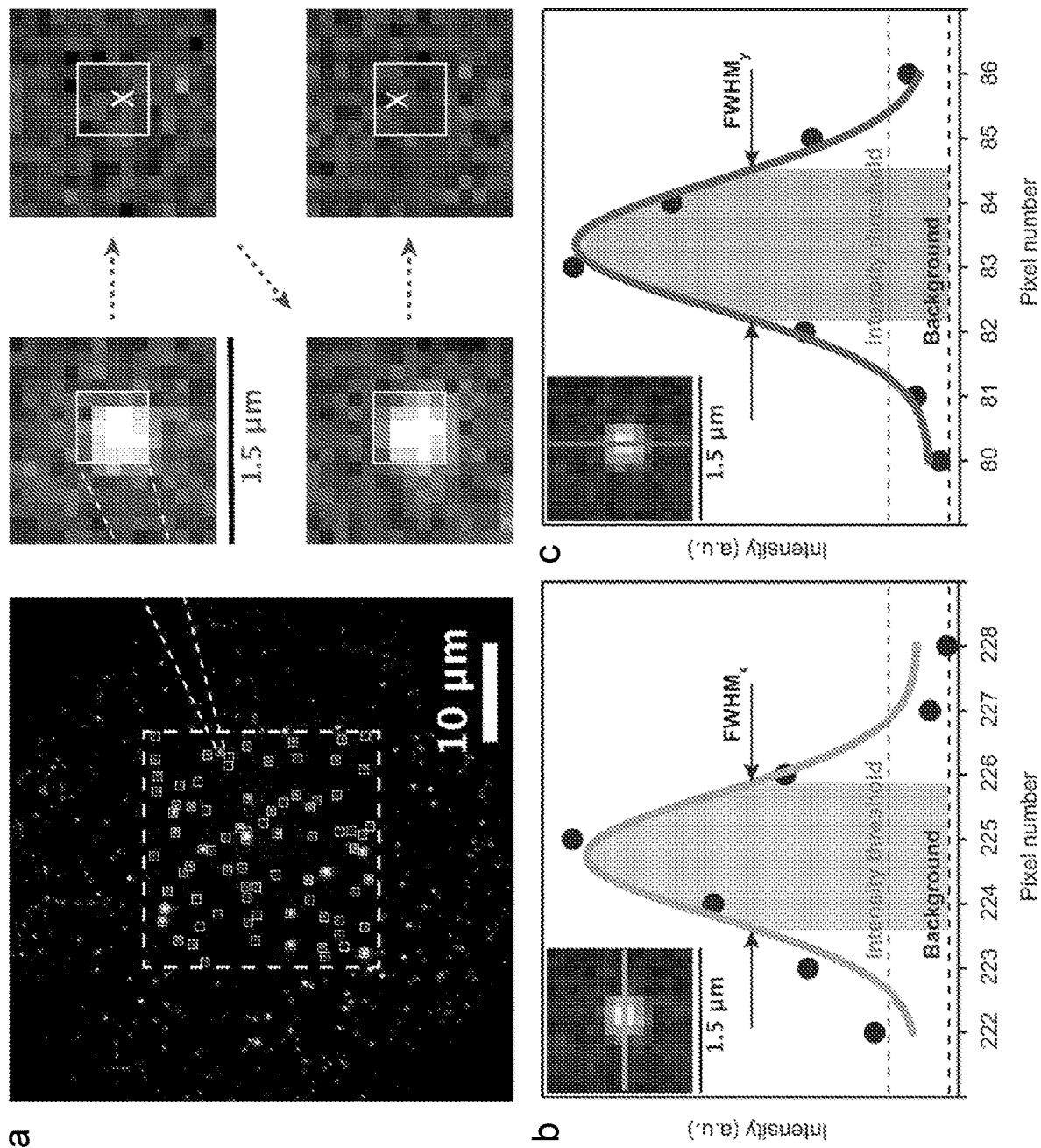
FIG. 10 shows STORM photon statistical analysis illustration. (a) Maximum intensity projection of image stack of a 512×512 pixels TIRF microscope movie. To guarantee even illumination, the image stack was cropped to 256×256 pixels (dotted line) and was then processed using the photon statistics algorithm described in this section. Boxes indicate the 5×5 pixel regions centered on the locations (X) derived from the MLE calculation. The dashed arrows between the enlarged sample region indicate the frame progression of the same region throughout the image stack. (b and c) Gaussian fitted x and y pixel intensity values of the sample region. The indicated intensity threshold was only used to determine if the region qualifies as a localization based on the criteria described above. Once the positions are determined, the x and y regions were fit to a Gaussian and integrated between the full-width half-maximum (FWHM) values of the pixel intensity values and above the background. The final integrated values are then converted to photons as described above. (d) A representative photon time trace derived from the collective integrated values of one localization through all frames of the image stack. (e) An example photon histogram of one sample derived from the integrated photon number that is above the photon intensity threshold (switching event).
Figure 10:
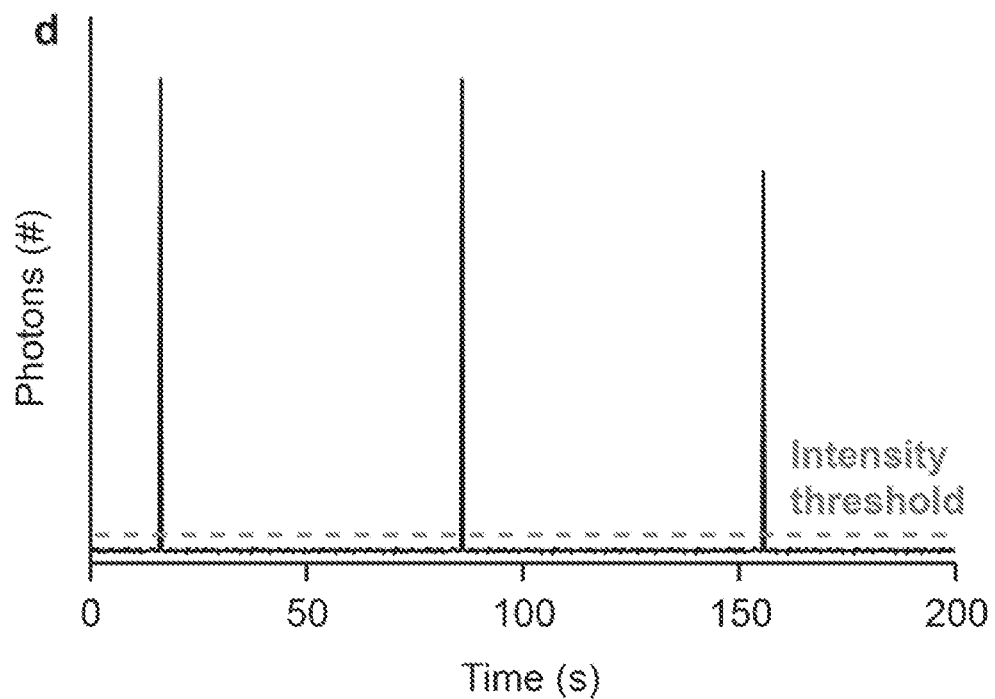
Figure 10:
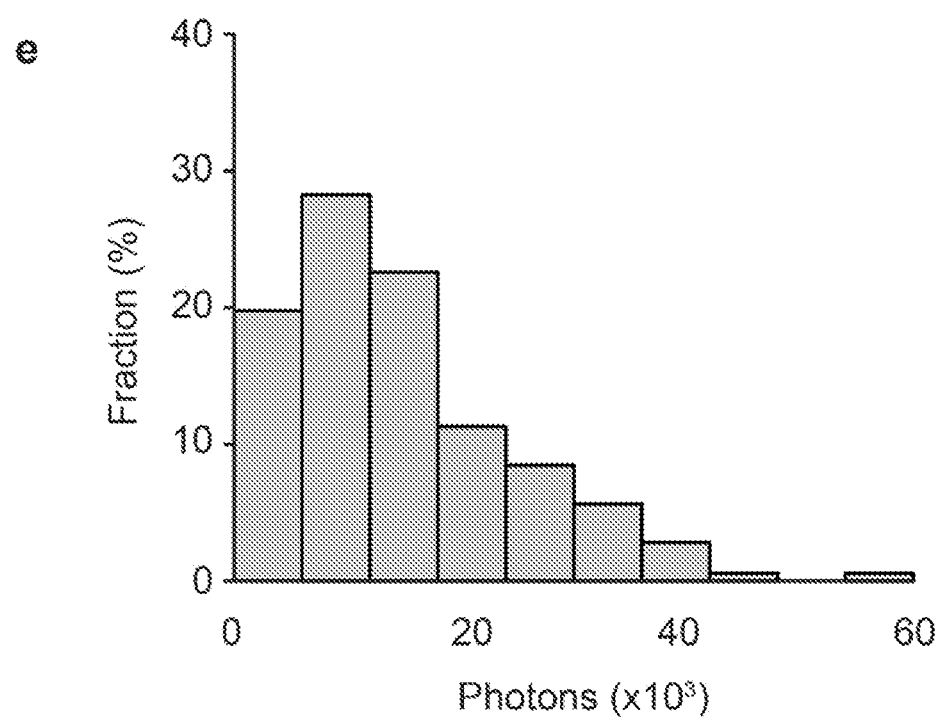
Figure 11:
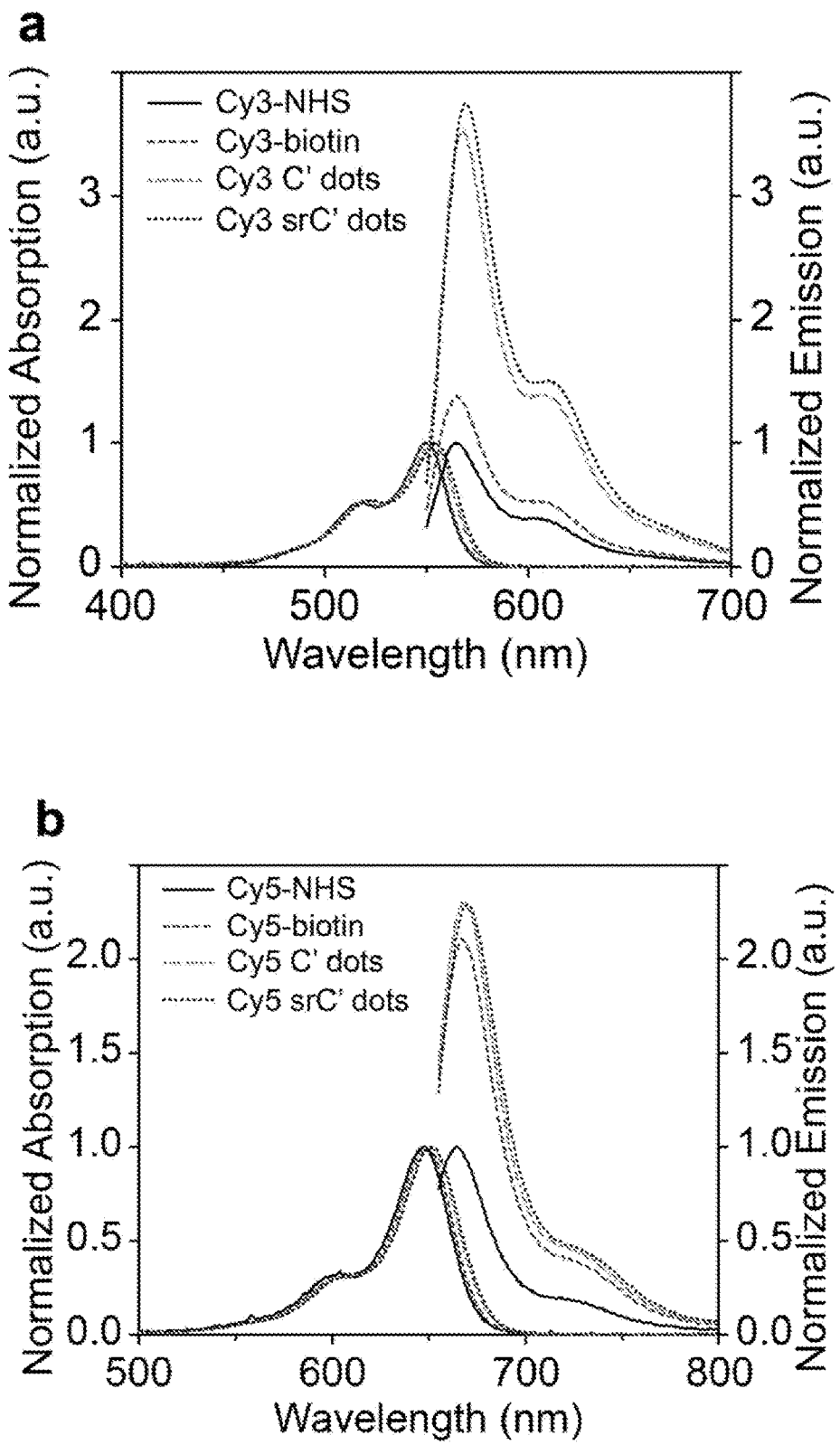
FIG. 11 shows comparison of different dyes and srC' dots. Normalized steady-state absorption and emission spectra and normalized FCS autocorrelation curves for, (a and d) Cy3, Cy3-biotin, Cy3-C' dots, and Cy3-srC' dots, (b and e) Cy5, Cy5-biotin, Cy5-C' dots, and Cy5-srC' dots, and c & f, DY782, and DY782-srC' dots. All samples were excited 10 nm below the absorption maximum. Chemical structures of, (g) Cy3-biotin, h, Cy5-biotin, and, (i) DY782-NHS. While in the case of Cy3 there is a significant quantum enhancement from Cy3-biotin to encapsulated Cy3 (factor of 2.7), the enhancement from Cy5-biotin to encapsulated Cy5 is small (factor of 1.1). Other cyanine dyes, e.g. Dy782, show very strong quantum enhancements upon encapsulation of free dye (factor of 9.3), making them possible candidates for NIR/IR super-resolution dyes when encapsulated in srC' dots.
Figure 11:
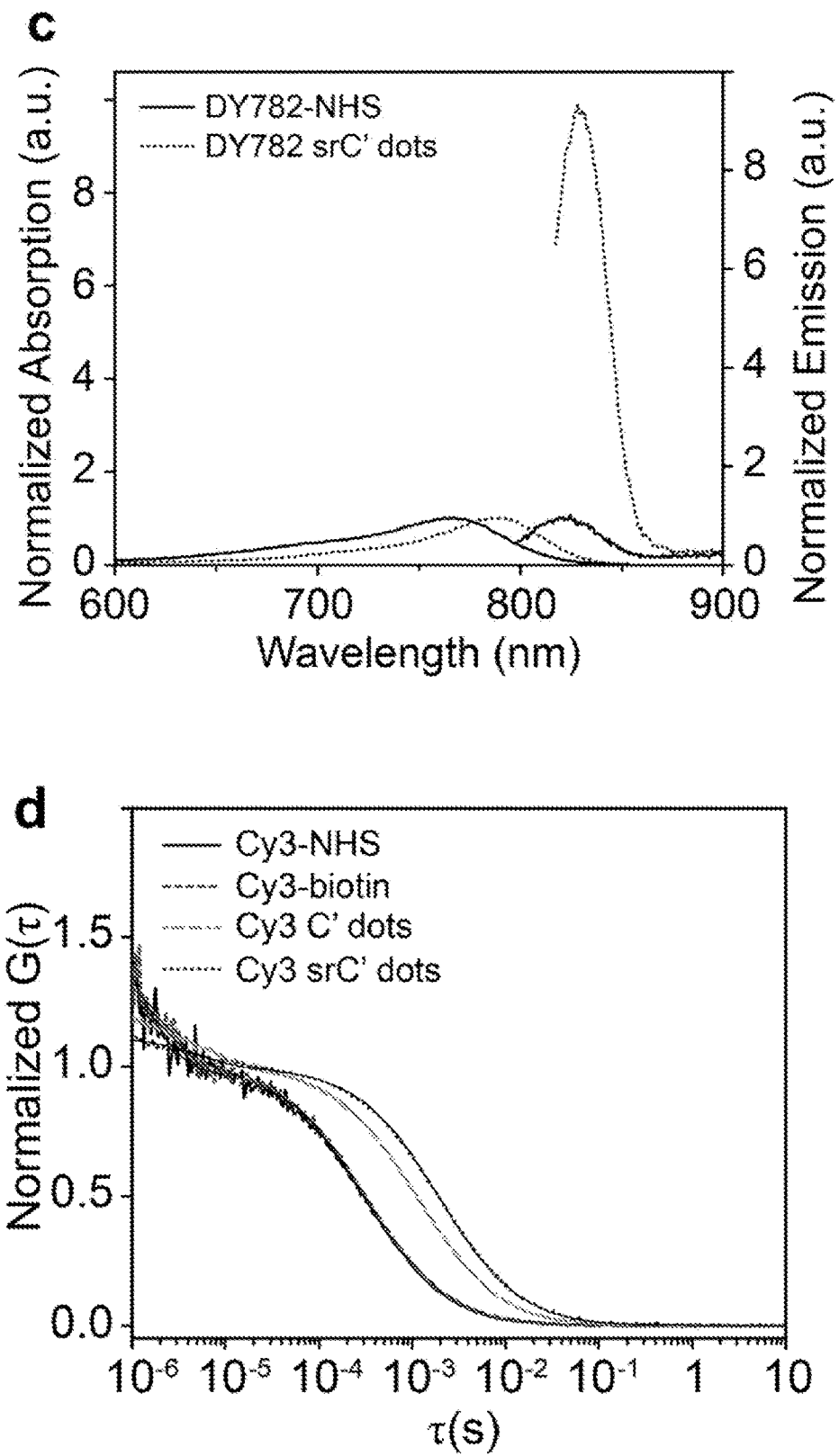
Figure 11:
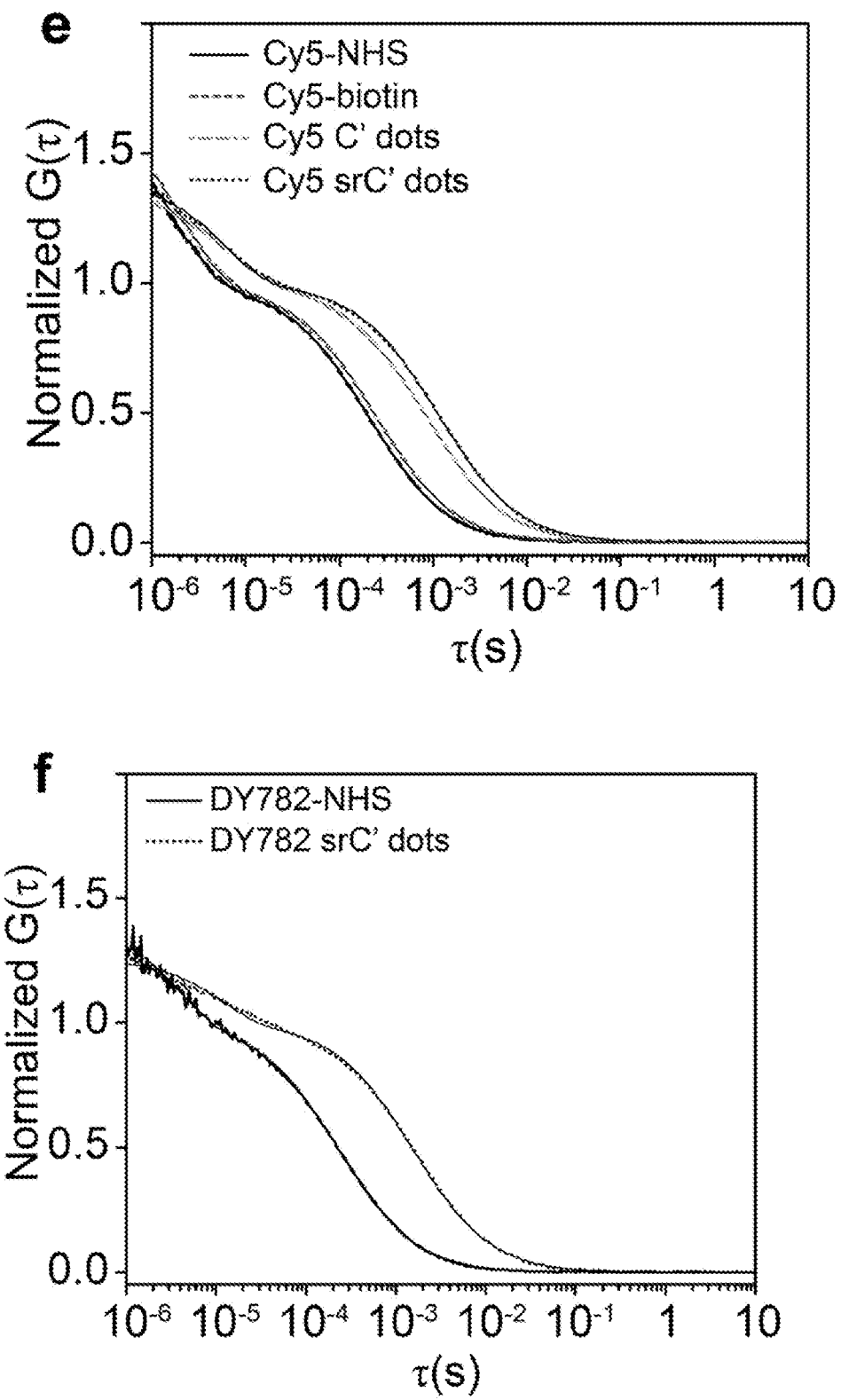
Figure 11:
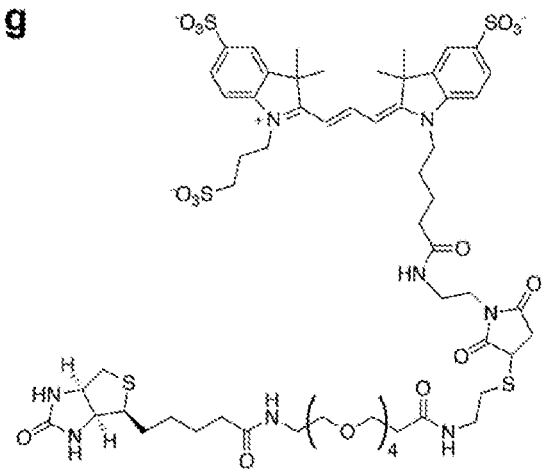
Figure 11:
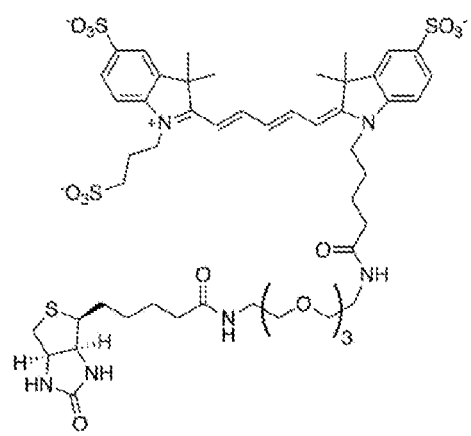
Figure 11:
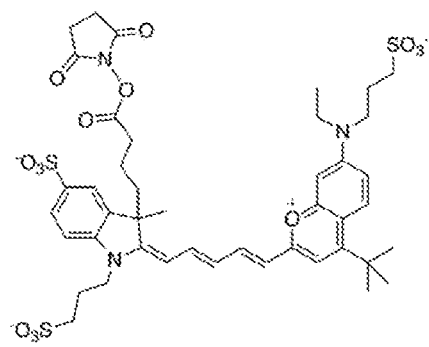

We imaged Cy5-biotin as well as biotinylated 0% and 60% srC' dots (FIG. 1a and FIG. 11h) immobilized on streptavidin-coated glass surfaces with total internal reflection fluorescence microscopy (TIRFM). While Cy5-biotin was studied with and without βME, srC' dots were only studied in the absence of βME. FIGS. 3b and 3c show three representative fluorescence time traces for each sample in PBS buffer (FIG. 10). While Cy5-biotin and the control particle bleach in a matter of seconds, Cy5-biotin and 60% srC' dots in the presence and absence of βME, respectively, show fluorescence blinking behavior over the entire data acquisition time. This suggests that the local thiol group concentration within these srC' dots enables encapsulated Cy5 to enter long-lived dark states. Similar results were obtained by replacing Cy5 with Cy3 (FIG. 3d, 3e, and FIG. 11g). Unlike in the case of Cy5, however, the blinking intensity of 60% Cy3 srC' dots is substantially enhanced over Cy3-biotin dye. The different emissive behavior is further reflected in corresponding photon histograms (FIG. 3f to i). While Cy5 srC' dots show a factor of about 1.1 more photons per switching event than Cy5-biotin, this factor increases to 2.7 for Cy3. These factors are consistent with quantum enhancements as estimated by steady-state emission spectra of absorption matched samples of Cy3- and Cy5-biotin as compared to respective srC' dots (FIG. 11 and Table 1). Since for specific dyes these enhancements via silica encapsulation can easily reach an order of magnitude (see results for DY782 dye in FIG. 11c and Table 1), results suggest a path to ultrabright SR imaging probes.

Another important parameter to evaluate fluorescent probes for STORM is the on-off duty cycle. It should be low to minimize the probability that another probe fluoresces within the diffraction limited area to optimize image resolution according to the Nyquist criterion. Analysis yielded an average of 0.0003 for both Cy5-biotin and Cy5 60% srC' dots, and 0.0003 for Cy3-biotin and 0.0007 for Cy3 60% srC' dots. Results put 60% srC' dots well into the range of useful super-resolution fluorescent probes.

Figure 4:
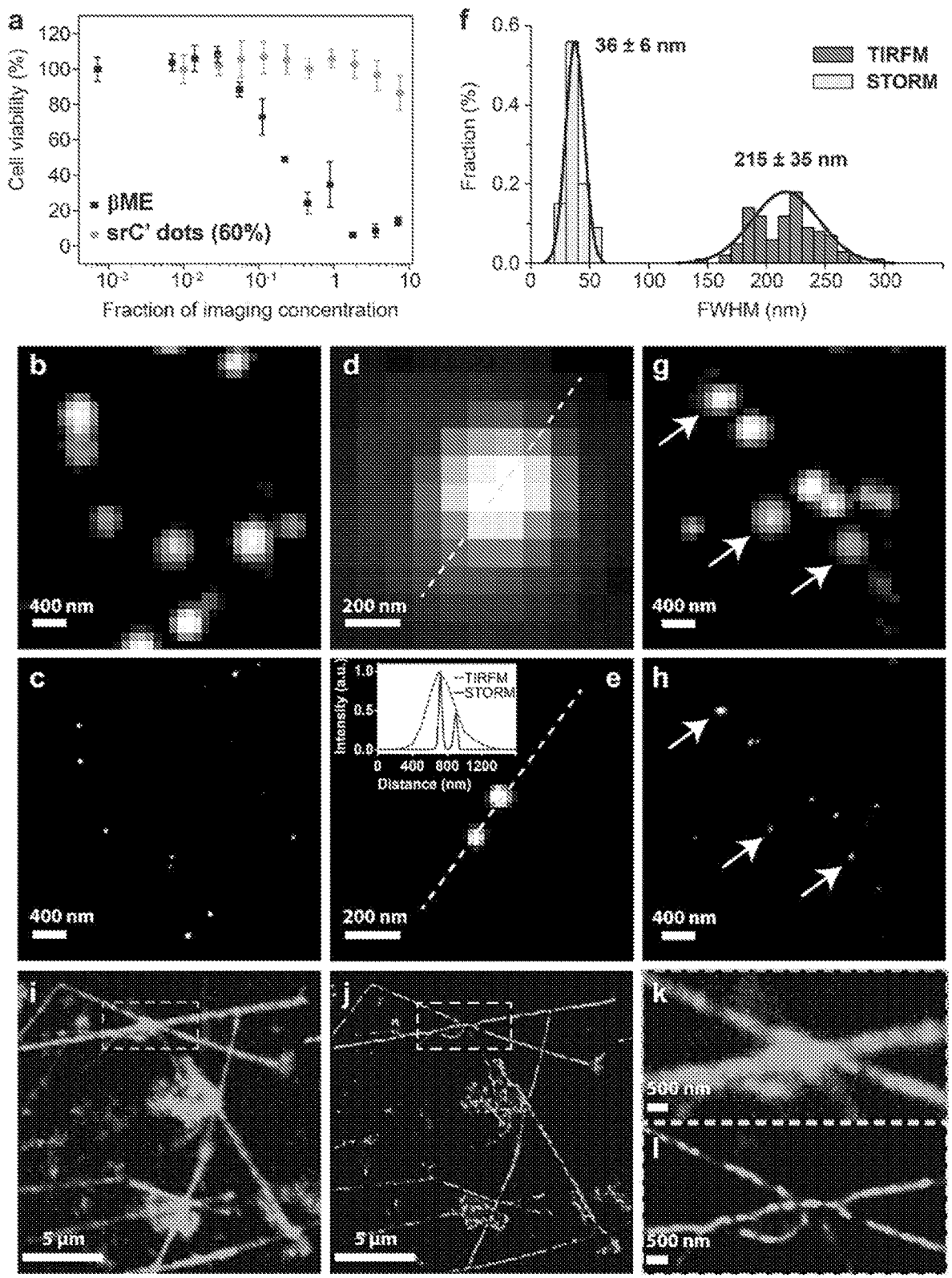
FIG. 4 shows cell viability and STORM microscopy. (a) Cell viability tests with BxPC3 cell line in complete media under the influence of (ME or Cy5 srC' dots (60%) at different concentrations, normalized to typical values used in STORM microscopy for comparative purposes as detailed in the text. (b and d) Total internal reflection fluorescence microscopy (TIRFM) images of Cy5 srC' dots (60%) in PBS in the absence of (ME. (c and e) Corresponding reconstructed super-resolution images. For dotted lines in d and e line intensity profiles are plotted in the inset of e revealing resolution enhancement for the reconstructed STORM image over the diffraction limited TIRFM image. (f) FWHM image analysis of TIRFM images and reconstructed super-resolution images from STORM. (g) TIRFM images of Cy5 srC' dots and Cy3 srC' dots in PBS in the absence of βME, and (h) corresponding reconstructed super-resolution image (Cy5 srC' dots are identified by white arrows). (i) TIRFM image and (j) SR image of Cy3 srC' dot labeled microtubules. Overlapping features in the TIRFM image (k) highlight improved resolution in the SR image (l).

To illustrate the biological benefits of srC' dots, we compared the effects of 25 min derived Cy5 based 60% srC' dots and βME when applied to BxPC3 pancreatic cancer cells in complete media. FIG. 4a shows %-cell viability for BxPC3 cells following 6 days of treatment with 60% srC' dots versus only a 16-hour treatment with βME. For direct comparison, the compound concentrations on the X-axis were scaled as 'fraction of imaging concentration.' This is the concentration of either compound divided by typically reported imaging concentrations, i.e. 1 μM for the high end of dye labeling, or 140 mM for the preparation of a typical STORM imaging cocktail using βME. At only 10% (i.e. 14 mM) of the typical imaging concentration for βME, substantial cell death is observed after only 16 hours, while a nearly ten-fold increase (i.e. 7.5 μM) beyond the typical concentration of srC' dots was well tolerated, with only minimal effects on cell viability even after a 6-day treatment.

We analyzed image stacks of Cy5 60% srC' dots in SR microscopy with open source ImageJ plugin ThunderSTORM. FIG. 4b shows an excerpt from a diffraction-limited TIRFM image with multiple localized srC' dots. Although most particles seem spaced out far enough to be resolved, comparison with the corresponding SR result (FIG. 4c) reveals particles only clearly separated in the latter. FIG. 4d displays a total internal reflection fluorescence microscopy (TIRFM) image that appears to show just one single particle. Applying the STORM reconstruction overcomes the diffraction limit, however, and exposes two separate particles (FIG. 4e). The inset of FIG. 4e shows the corresponding cross-sectional line profiles of the diffraction limited TIRFM image and reconstructed STORM image revealing a center-to-center particle distance of 175 nm. Corresponding analysis (FIG. 4f) of localized particles for their full width half maximum (FWHM), shows a decrease from 215±35 nm to 36±6 nm. To demonstrate dual color STORM, we sequentially imaged glass slides functionalized with Cy5 and Cy3 srC' dots (FIGS. 4g and 4h). FIGS. 4i and 4j shows a TIRFM image of Cy3 srC' dots labeled microtubules and the respective SR image, highlighting the increased resolution in particular for overlapping features (FIGS. 4k and 4l).

Figure 5:
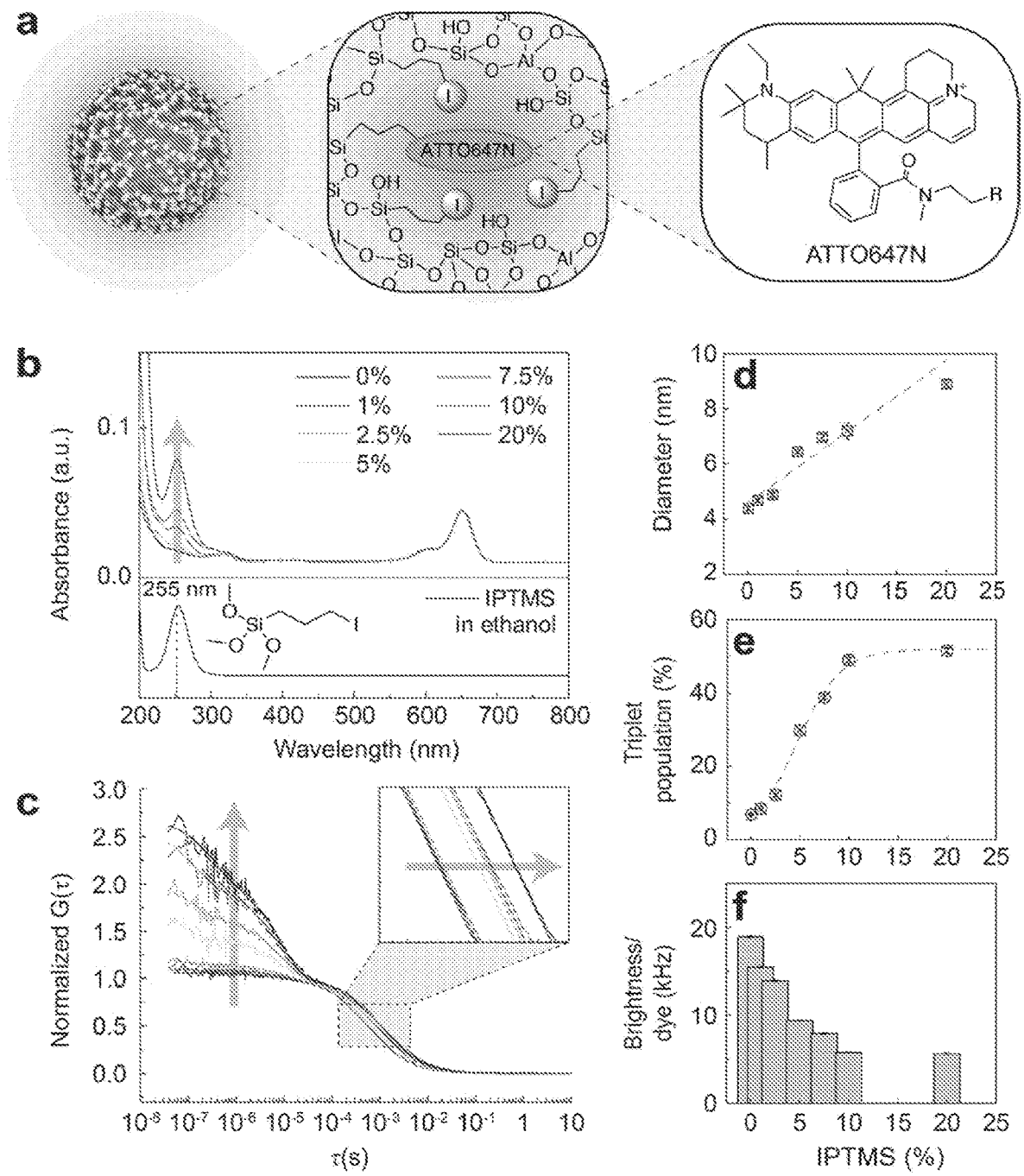
FIG. 5 shows particle molecular triplet state photo-engineering. (a) ATTO647N particle rendering with local molecular structure model and chemical structure of encapsulated ATTO647N. R represents a functional group attached by a carbon atom. (b) Comparison of absorption spectra of ATTO647N iC' dots in water (top), synthesized from different relative molar amounts of 3-iodopropyl trimethoxysilane (IPTMS) precursor (0%, 1%, 2.5%, 5%, 7.5%, 10%, and 20%), and of IPTMS in ethanol (bottom). The band in the particle spectra at about 255 nm increases with increasing IPTMS amount (grey arrow). The inset shows the chemical structures of IPTMS. (c) Normalized afterpulse corrected FCS autocorrelation curves of ATTO647N iC' dots. The triplet population and particle size increase with increasing IPTMS amount (grey arrows). Fits used a correlation function with translational diffusion, singlet-triplet transition, and rotational diffusion components. Inset shows enlarged correlation curves with fits. (d) Diameter from FCS fits plotted against ITPMS precursor amount. (e) Triplet population plotted against IPTMS precursor amount. Dotted lines in (d) and (e) serve as visual guides. (f) FCS derived brightness per dye plotted against IPTMS precursor amount.

We applied the PMPE concept to the formation of other transient dark states. Control over the triplet state population could be useful for optical shelving of organic dyes for application in GSD microscopy. In analogy to STORM, additives that enhance the photoinduced triplet state formation are added to 'imaging cocktails,' but may not be conducive to sensitive live cell imaging. We utilized the external heavy atom effect of iodine to finely tune the triplet state population of carbo-rhodamine dye ATTO647N (FIG. 5a). Intersystem crossing (ISC) is a spin forbidden transition, but is enhanced by quantum mechanical spin-orbit coupling. The intramolecular or external presence of heavy atoms leads to increased ISC rates, kisc, for a fluorophore. The efficiency of spin-orbit coupling scales with Z, where Z denotes the atomic number of the heavy atom. Eliminating effects of detector afterpulsing, singlet-to-triplet transitions can be studied by FCS, where increased triplet populations are manifested by increases in amplitudes of fast processes at lag times between 100 ns and 10 μs.

Figures 12, 13:
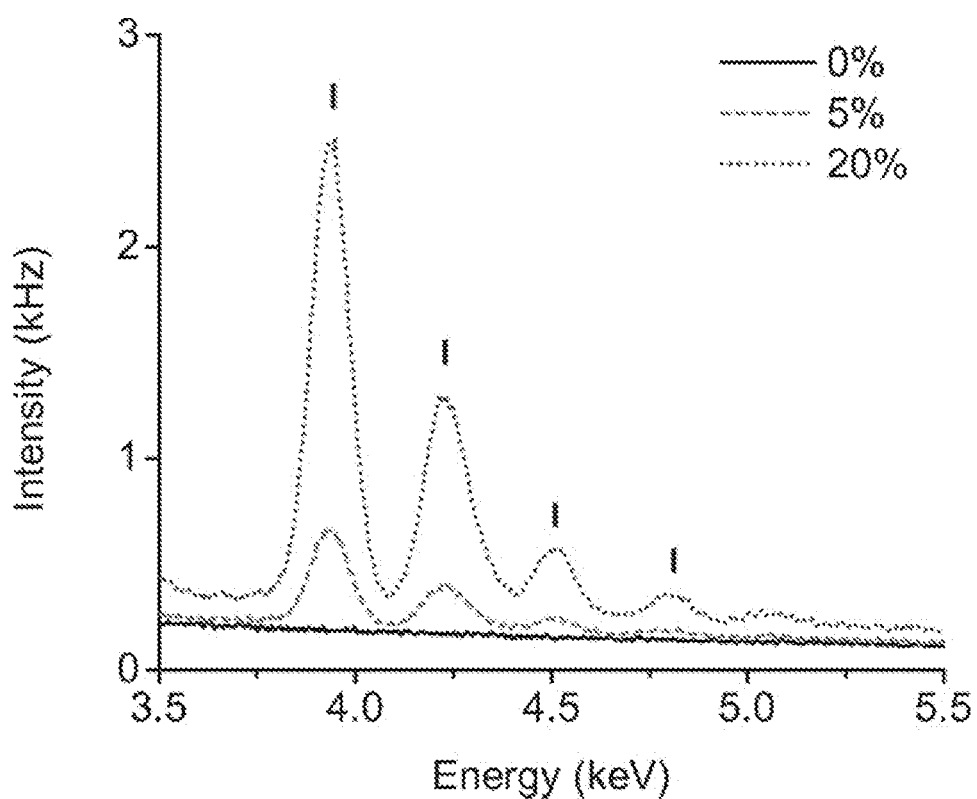
FIG. 12 shows a table describing quantum enhancement as compared to free dye of absorption matched samples, QE, hydrodynamic diameter, d, and number of dyes per particle, n.
FIG. 13 shows EDS spectra of iC' dots. EDS spectra of the 0%, 5% and 20% iC' dots and peak assignments for iodine (I). The characteristic L-edge line series of iodine is only observed for the latter two dots with peaks at 3.9 keV, 4.2 keV, 4.5 keV, and 4.7 keV.

We synthesized a series of SNPs referred to as iC' dots containing ATTO647N dye from increasing molar ratios of the iodine containing silica precursor (3-iodopropyl)trimethoxysilane (IPTMS) relative to TMOS: 1% iC' dots, 2.5% iC' dots, 5% iC' dots, 7.5% iC' dots, 10% iC' dots, and 20% iC' dots, as well as a control particle with no IPTMS, 0% iC' dots (FIGS. 5a and b, bottom inset). Particles were prepared and purified using protocols similar to the thiol containing dots, essentially replacing MPTMS with IPTMS. FIG. 5b shows the ATTO647N intensity-matched UV-vis spectra of this particle series in deionized water. Spectra exhibited the 647 nm absorption of ATTO647N, as well as a prominent 255 nm UV absorption band which increased with increasing IPTMS precursor amount. An absorption spectrum of pure IPTMS recorded in 100% anhydrous ethanol to avoid precursor condensation matched this UV-band well. Iodine was independently evidenced by EDS measurements on 0, 5, and 20% iC' dots (FIG. 13). Particle hydrodynamic diameters determined by FCS (FIG. 5*c*) using a fit correlation function accounting for translational diffusion, singlet-triplet transitions, and rotational diffusion, were: $d_{0\%iC'dots}$=4.4 nm, $d_{1\%iC'dots}$=4.7 nm, $d_{2.5\%iC'dots}$=4.9 nm, $d_{5\%iC'dots}$=6.5 nm, $d_{7.5\%iC'dots}$=7.0 nm, $d_{10\%iC'dots}$=7.2 nm, and $d_{20\%iC'dots}$=8.9 nm. Particle size increased roughly linearly with increasing IPTMS molar amount (FIG. 5*d*). The number of dyes per particle, n, stayed close to n=1 over the entire series: $n_{0\%iC'dots}$=1.0, $n_{1\%iC'dots}$=1.3, $n_{2.5\%iC'dots}$=1.3, $n_{5\%iC'dot}$=1.3, $n_{7.5\%iC'dots}$=1.2, $n_{10\%iC'dots}$=1.0, and $n_{20\%iC'dots}$=1.0.

Figure 14:
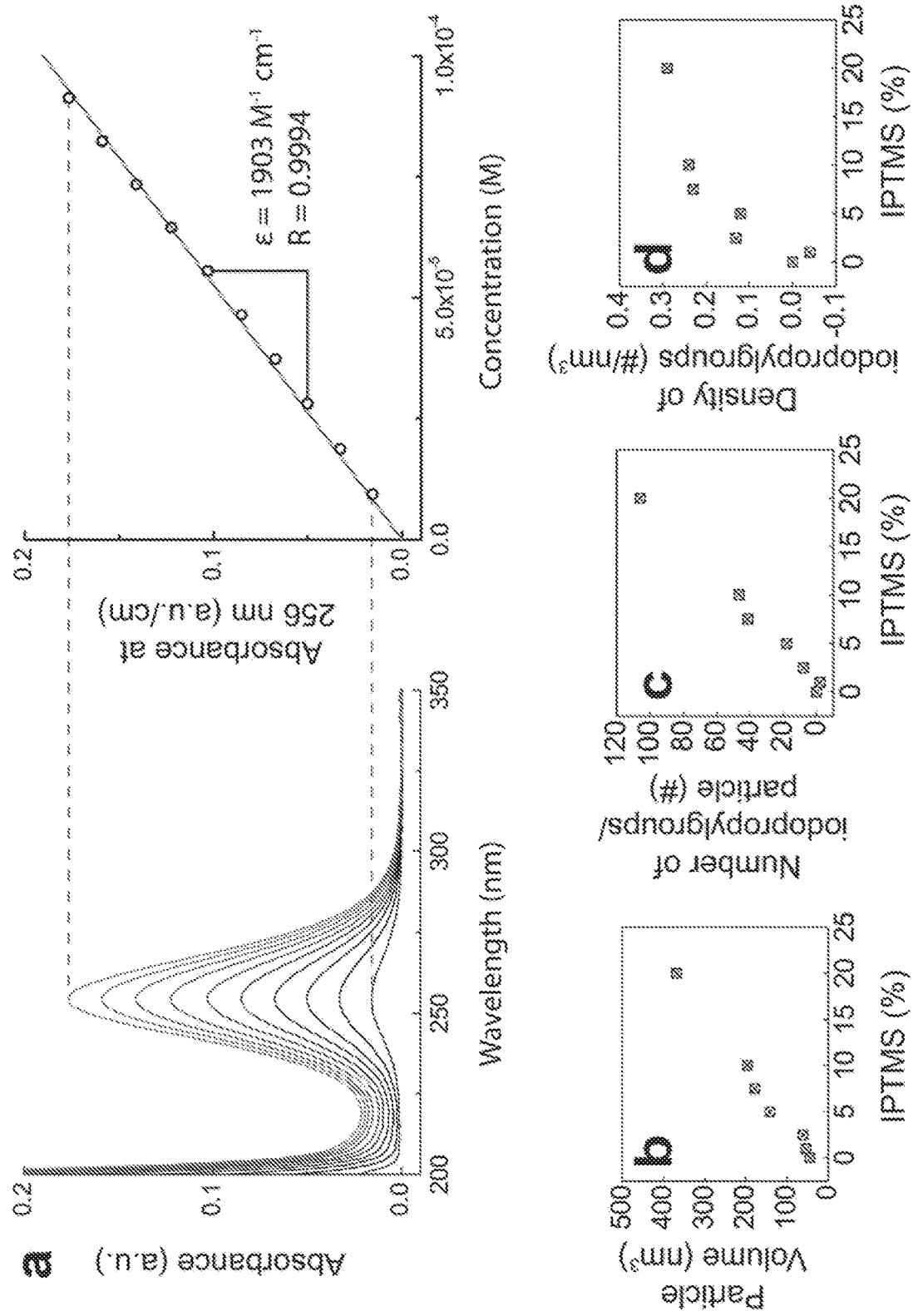
FIG. 14 shows characterization of iodopropyl groups in iC' dots. (a) Determination of molar extinction coefficient of IPTMS in ethanol. Absorption spectra at different IPTMS concentrations (left), and plot of corresponding peak maxima at 256 nm against IPTMS concentration (right). (b) Particle volume as calculated from particle diameter. (c) Number of iodopropyl groups as determined from a combination of FCS and absorption measurements. (d) Estimated iodopropyl group density as obtained from data in (b) and (c).

FCS results in FIG. 5*c* reveal a substantial increase in amplitude for singlet-triplet transitions with increasing IPTMS precursor amounts, making iC' dots attractive candidates for GSD microscopy. In FIG. 5*e*, the %-triplet population for the different ATTO647N iC' dots, normalized for the number of dyes per particle, first strongly increases between 0% and 10% IPTMS precursor and then saturates slightly above 50%, amounting to an increase of about 610%. The triplet population follows the iodopropyl-group density in a particle, as derived from absorption and FCS measurements (FIG. 14). As expected, the fluorescence quantum efficiency per dye as revealed by FCS determined particle brightness (photon counts per particle by the APDs) simultaneously decreases to about a fourth of its initial value (FIG. 5*f*).

Figure 6:
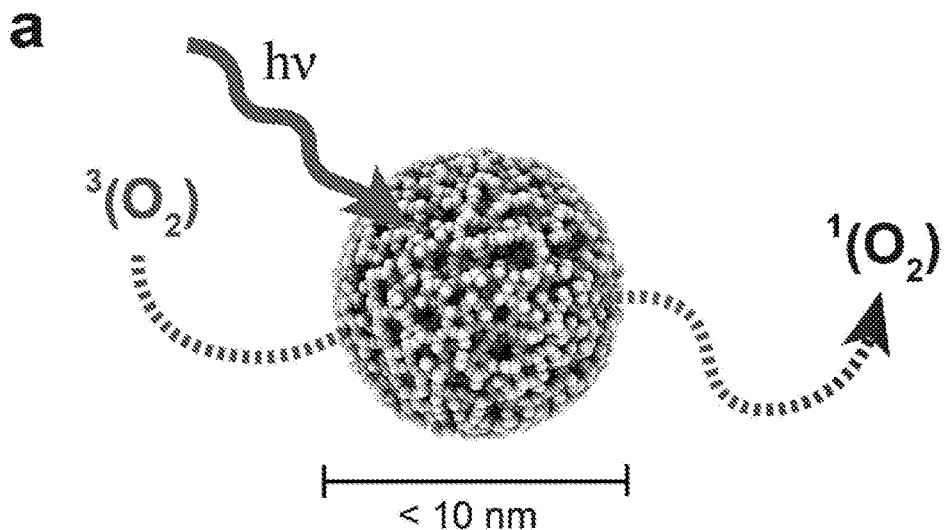
FIG. 6 shows singlet oxygen quantum yield determination. (a) Particle rendering with schematic of triplet oxygen, $^3(O_2)$, diffusing through the microporous silica network and being transformed into singlet oxygen, $^1(O_2)$, by encapsulated dyes under red light illumination. (b) Simplified Jablonski diagram illustrating the creation of singlet oxygen. $^1$(PS) denotes the singlet ground state, while $^1$(PS)* and $^3$(PS)* denote electronically excited singlet and triplet states of a dye photosensitizer (PS), respectively. $^3(O_2)$ and $^1(O_2)$ denote triplet ground state and excited singlet state of molecularly dissolved oxygen, respectively. (c) Singlet oxygen sensor 1,3-diphenylisobenzofuran (DPBF) and its reaction to 1,2-dibenzoyl-benzene in the presence of $^1(O_2)$. (d) Absorption spectra of a solution of ATTO647N encapsulating 7.5% iC'dots and DPBF, irradiated at 635 nm (ATTO647N absorption band) for 0 s to 600 s (black arrow). Singlet-oxygen generation for, (e) ATTO647N dye (dashed line) as compared to ATTO647N encapsulating 0%, 2.5%, 5%, 7.5% and 10% iC'dots (solid lines), and (f) methylene blue dye (dashed line) as compared to MB2 encapsulating 0%, 7.5% and 15% iC'dots (solid lines). The inset of (f) shows the chemical structure of encapsulated methylene blue derivate MB2. R represents a functional group attached by a carbon atom.
Figure 6:
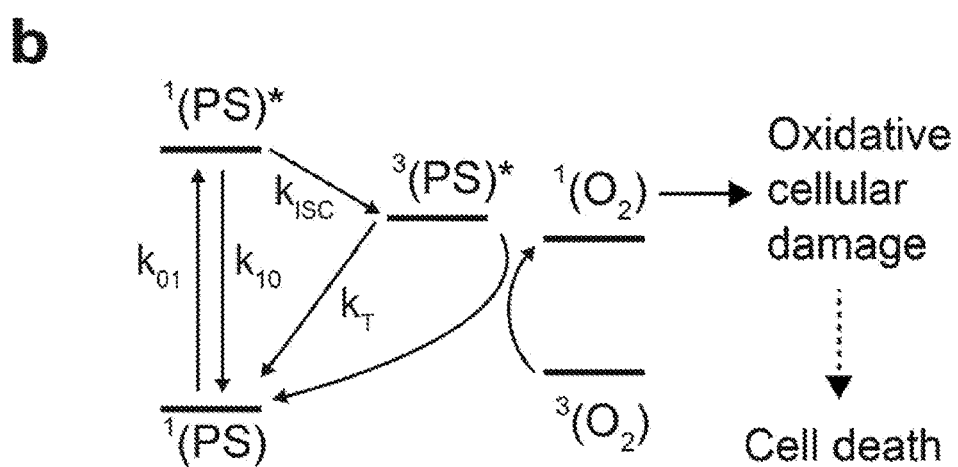
Figure 6:
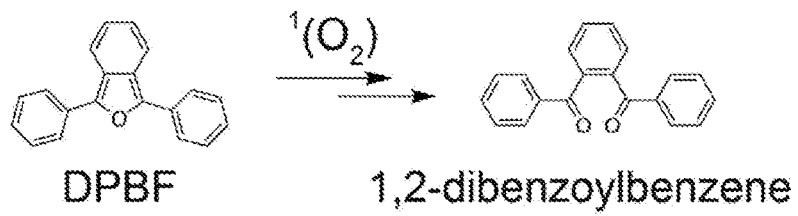
Figure 6:
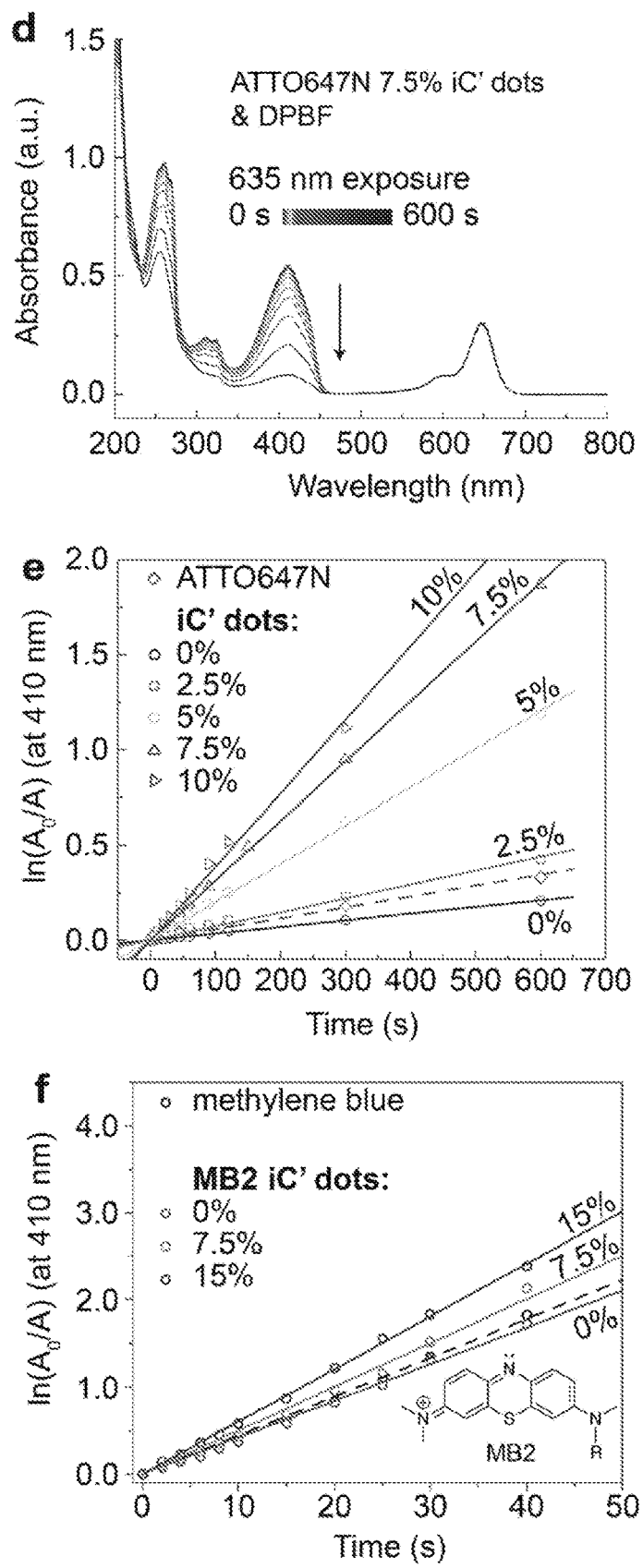

An increase in triplet state dye population is often associated with an increase in singlet oxygen ($^1O_2$) quantum yield, $\Phi_\Delta$. $^1O_2$ is produced by energy transfer between the triplet state dye and dissolved triplet oxygen $^3O_2$ (FIG. 6*b*). By introducing a photosensitizer (PS) dye, ultrasmall SNPs transition from passive (diagnostic) to active (therapeutic) probes, e.g. for photodynamic therapy (PDT). In iC' dot based PDT, a targeted probe with high $\Phi_\Delta$ would specifically bind to biological sites of interest, would be excited with light to produce $^1O_2$, which in turn would induce cell death via necrosis and/or apoptosis (FIGS. 6*a* and 6*b*). While heavy atoms can enhance $\Phi_\Delta$ of PSs in NPs, the enhancement of $\Phi_\Delta$ by heavy atoms in sub-10 nm SNPs, a critical size range for renal clearance, to the best of our knowledge has not been reported.

Figure 15:
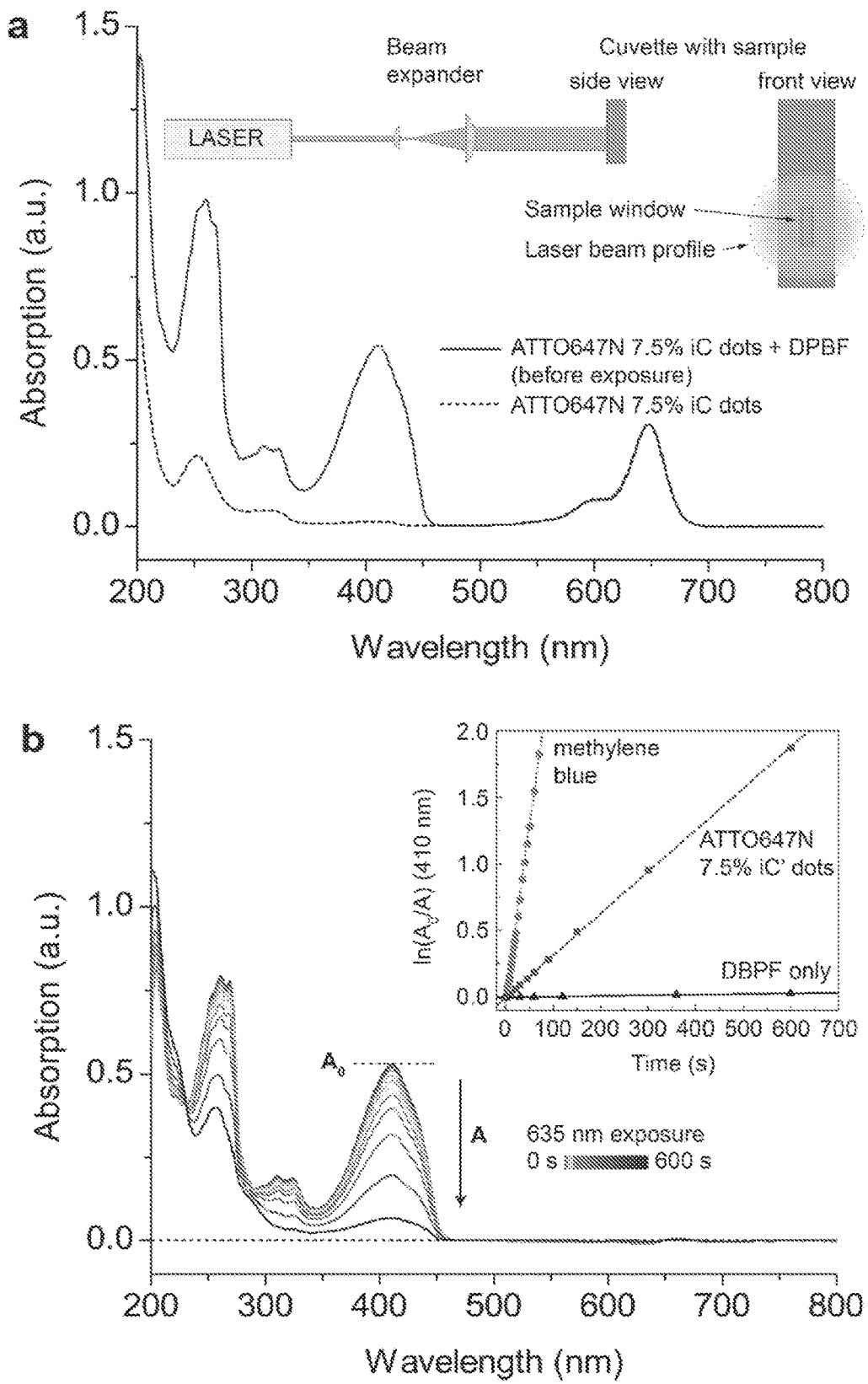
FIG. 15 shows determination of singlet oxygen quantum yields, $\Phi_\Delta$. (a) Absorption spectra of ATTO647N 7.5% iC' dots with and without DPBF in ethanol. The particle-only spectrum is used as a baseline and subtracted from the DPBF containing spectrum leading to the spectrum in (b). The inset in a shows the optical setup for the exposure of a sample in a microcuvette to a 635 nm solid state laser beam (3 mW/cm2). A beam expander is used to evenly illuminate the sample window. (b) Baseline-corrected absorption spectra of DPBF at different exposure times. The inset in (b) shows the natural logarithm of the relative DPBF absorption at 410 nm at different exposure times plotted against exposure time, and respective linear fits for the standard methylene blue (MB), the ATTO647N 7.5% iC' dots, and a negative control of DPBF only.
Figure 16:
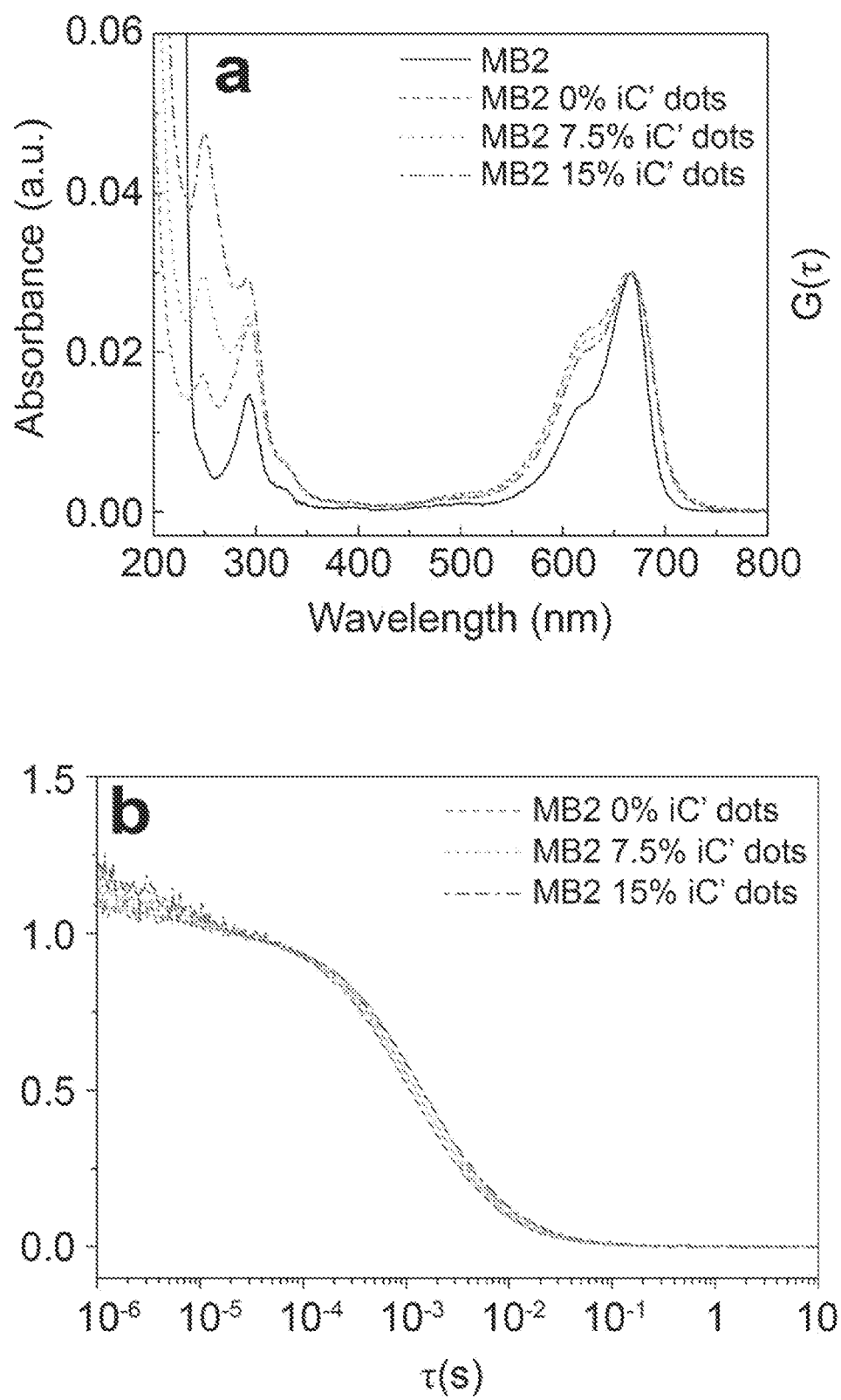
FIG. 16 shows characterization of iC' dots encapsulating MB2. (a) Absorption spectra of MB2, and MB2 encapsulating 0%, 7.5%, and 15% iC' dots. (b) FCS curves of TMR surface functionalized MB2 0%, 7.5%, and 15% iC' dots for particle size determination.
Figure 17:
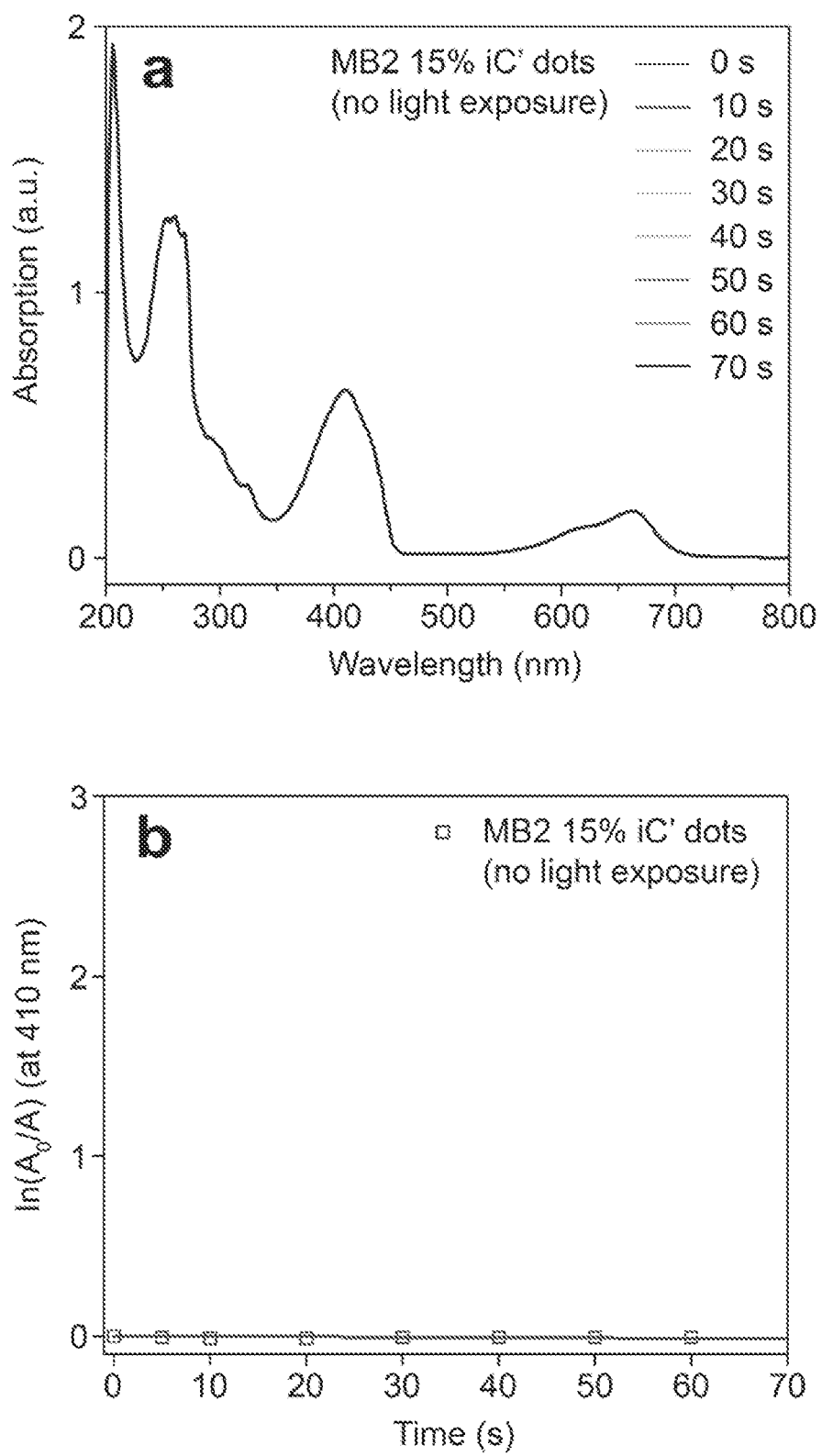
FIG. 17 shows dark toxicity measurement. (a) Absorption spectra of MB2 15% iC' dots containing DPBF at different times after DPBF addition. (b) Natural logarithm of the relative DPBF absorption at 410 nm at different times after DPBF addition.

We measured $\Phi_\Delta$ for the iC' dot series encapsulating ATTO647N by using the singlet oxygen sensor 1,3-diphenylisobenzofuran (DPBF), which forms 1,2-dibenzoyl-benzene with $^1O_2$ (FIG. 6*c*) as indicated by a reduction of an absorption band at 410 nm (FIGS. 6*d* and 15). Values of $\Phi_\Delta$ for ATTO647N dye and ATTO647N based iC' dots relative to the standard methylene blue were: 0.012 (ATTO647N), and 0.007, 0.015, 0.042, 0.065, and 0.080 for 0, 2.5, 5, 7.5, and 10% iC' dots, respectively (FIG. 6*e*) (FIG. 16 for an example calculation). When ATTO647N is embedded in a silica particle, $\Phi_\Delta$ is reduced from 0.012 to 0.007, likely due to steric shielding from dissolved oxygen by the silica network. When IPTMS is introduced, however, spin-orbit coupling compensates for steric hindrance and $\Phi_\Delta$ steadily increases by over an order of magnitude to 0.080. While a large relative effect, for PDT applications values of $\Phi_\Delta$>0.5 are desired. PMPE can be applied to other PDT relevant dyes to create such high $\Phi_\Delta$ probes. We synthesized 0, 7.5, and 15% iC' dots replacing ATTO647N with methylene blue derivate MB2 (FIG. 6*f* inset and FIG. 16). Observed $\Phi_\Delta$ values followed the same trend as ATTO647N based iC' dots and were: 0.520 (MB), and 0.492, 0.586, and 0.705 for 0, 7.5, and 15% iC' dots of 4.8, 5.4, and 6.2 nm size, respectively (FIG. 6*f*), while showing no signs of dark toxicity ($^1O_2$ generation in the absence of light irradiation, FIG. 17). Achieving $\Phi_\Delta$ values>0.7 places MB2 iC' dots in the range of top-performing PSs, while simultaneously enabling further surface functionalization with, e.g. targeting moieties and radiolabels providing multifunctional nanoprobes.

Methods—Synthesis of fluorescent srC' dots. For a 10 mL reaction of srC' dots, 145.4 μL (2 mg/1 mL in DMSO) of Cy5-NHS and 0.86 μL APTES (molar ratio 1:10) were combined in inert atmosphere in the dark to form Cy5-silane. The mixture was allowed to react for 12 hours. In a 25 mL round bottom flask, 400 μL hydrochloric acid (5 M) were added to 9.4 mL DI water and stirred at 600 rpm for 1 minute. This brought the pH to ~1.5. Under vigorous stirring, 51 μL MPTMS and 27.2 μL TMOS (molar ratio 6:4 or 60% MPTMS) were added into the acidic solution, immediately followed by all prepared Cy5-silane dye solution and 20 μL ASB. ASB was used in small molar amounts, but was necessary in the particle formation process by contributing to charge stabilization of particles in acidic solution. The relative precursor molar ratios of MPTMS to TMOS could be varied from 0% MPTMS to 80% MPTMS providing stable particles. Particles synthesized from 0%, 30%, 60%, and 80% MPTMS are denoted as 0%, 30%, 60%, and 80% srC' dots, respectively. The respective precursor mixture was allowed to react for 25 min, before the particle growth was quenched by rapidly adding 150 μL PEG-silane (~0.5 kg/mol). 5 minutes after PEG-silane addition the pH was adjusted by rapidly adding 100 μL of a 14% aqueous solution of ammonia. This brought the pH to about ~8. The particles were stirred for another 12 hours, before the stirring was stopped, and the samples heated to 80° C. over night. Finally, samples were transferred into a dialysis membrane (Pierce, molecular weight cutoff, MWCO=10,000) and placed in 2,000 mL of DI water to wash away any unreacted reagents and neutralize the particle dispersions. Water was changed twice at 6 and 12 hour time points. The particles were then filtered through a 0.22 μm syringe filter (Fisherbrand) to remove any large aggregates or dust that may have accumulated in the solution. All final solutions appeared faint blue and clear.

Biotinylated srC' dots were synthesized by following the same protocol but adding biotin-PEG-silane to the particle dispersion immediately prior to the PEG-silane addition. Biotin-PEG-silane precursor was prepared by reacting MPTMS with biotin-PEG-mal in a molar ratio of 1.1:1. For a 10 mL batch, 0.5 μL of MPTMS were combined with 45 μL of biotin-PEG-mal (50 mg/mL in DMSO) for 12 hours under an inert nitrogen atmosphere.

Synthesis of iC' dots. The synthesis pathway of iC' dots closely followed that of srC' dots. In short, for a 10 mL reaction 154.7 μL (2 mg/1 mL in DMSO) of ATTO647N-NHS were combined with 0.86 μL APTES (molar ratio 1:10) in an inert atmosphere in the dark to form ATTO647N-silane. The mixture was allowed to react for 12 hours. In a 25 mL round bottom flask, 1.0 mL hydrochloric acid (5 M) were added to 9.0 mL DI water and stirred at 600 rpm for 1 minute. Under vigorous stirring 0.9 μL IPTMS and 67.3 μL TMOS (molar ratio 1:99 or 1% IPTMS) were added into the acidic solution, and immediately followed by all conjugated ATTO647N-silane dye solution and 20 μL ASB. The relative precursor molar ratios of IPTMS to TMOS could be varied from 0% to 20% IPTMS while still providing stable particles. Particles synthesized with 0%, 1%, 2.5%, 5%, 7.5%, 10%, and 20% IPTMS are denoted as 0%, 1%, 2.5%, 5%, 7.5%, 10%, and 20% iC' dots. The respective precursor mixture was allowed to react for 15 min, before the particle growth was quenched by rapidly adding 150 μL PEG-silane (~0.5 kg/mol). 5 minutes after PEG-silane addition the pH was adjusted by rapidly adding 100 μL of a 14% aqueous solution of ammonia. The particles were stirred for another 12 hours, before the stirring was stopped, and the samples heated to 80° C. over night. MB2 0, 7.5, and 15% iC' dots were synthesized according to the protocol above, replacing ATTO647N-NHS with MB2-NHS. Due to the non-emissive nature of MB2, MB2 iC' dots were surface functionalized with TMR dye according to a previously reported protocol. This enabled FCS measurements for the determination of hydrodynamic radii. Since it could not be guaranteed that all particles were functionalized with TMR, the number of MB2 molecules per particle were not determined. The cleaning of iC' dots was analogous to srC' Cots.

Synthesis of fluorescent C' dots. C' dots were synthesized according to previously described methods. The dye concentrations for Cy3 and Cy5 were kept the same as for srC' dots. All dyes had maleimide functional groups, instead of NHS functional groups. The conjugation ratio of dye to MPTMS was 1:25. The cleaning of C' dots was analogous to iC' dots and srC' dots.

Particle filtration. To increase SNP purity, we performed gel permeation chromatography (GPC) using a BioLogic LP system alongside a 275 nm UV detector with cross-linked copolymer of allyl dextran and N,N'-methylene bisacrylamide (Sephacryl S-300 HR) from GE Healthcare. Particle solutions were up-concentrated by centrifuge spin-filters (GE Healthcare Vivaspin with MWCO 30K), sent through the column with a 0.9 wt % NaCl solution, and collected by a BioFrac fraction collector. The corresponding GPC fractions were transferred back into DI water by washing the particles at least 5 times in a spin-filter. The cleaning steps via dialysis and GPC are of crucial importance to remove unreacted MPTMS, whose thiol groups could alter the photophysical properties in post synthesis particle characterization. Purified samples were subjected to storage in DI water in the dark at 4° C. for further characterization.

$^{29}$Si, $^{27}$Al and $^{13}$C solid-state NMR characterization. Solid-State NMR (ssNMR) samples were synthesized according to the protocol described above. For one ssNMR sample five 10 mL batches per particle type were synthesized and combined into one sample. Samples were freeze-dried and then kept in a vacuum oven for three days at 30° C.

$^{29}$Si and $^{13}$C solid state NMR (ssNMR) experiments were conducted on a Bruker Avance DSX NMR spectrometer with a 9.4 T magnet (400.24 MHz proton Larmor frequency, 100.64 MHz $^{13}$C Larmor frequency, 79.52 MHz $^{29}$Si Larmor frequency) using probe heads for rotors of 7 mm ($^{29}$Si NMR) and 4 mm diameters ($^{13}$C NMR). The $^{27}$Al NMR experiments were performed on a Bruker Avance NMR spectrometer with a 16.45 T magnet (182.47 MHz $^{27}$Al Larmor frequency) using a probe head for rotors of 2.5 mm diameter.

$^{29}$Si cross-polarization/magic angle spinning (CP/MAS) NMR experiments were conducted in rotors of 7 mm diameter spinning at 5.0 kHz. The CP parameters were optimized with 4,4-dimethyl-4-silapentane-1-sulfonic acid (DSS), which also served as secondary chemical shift standard at 1.50 ppm. The $^{29}$Si CP/MAS NMR spectra were acquired with a 5 second repetition time, 5 ms CP contact time, acquiring 1200 scans (0% srC' dots), 800 scans (30% srC' dots), and 1440 scans (60% srC' dots).

$^{27}$Al spectra were acquired by single pulse excitation. The $^{27}$Al NMR chemical shift scale was referenced externally against potassium alum at −0.033 ppm as a secondary reference. The 90 degree pulse time was also determined on this sample. The final 1-d MAS spectra were acquired with a nominally 10 degree pulse (on a nearly cubic sample) at 95 kHz rf field strength at 25.00 kHz sample spinning with 100 ms repetition times accumulating 7200 scans. The $^{27}$Al background of probe and rotor were characterized by acquiring the spectrum of an empty rotor under identical conditions. The signal of the empty rotor was subtracted from the sample spectra.

For $^{13}$C CP/MAS NMR experiments samples were spun at 7.0 kHz at the magic angle. The experimental parameters for the $^{13}$C CP/MAS experiments with TPPM proton decoupling were optimized on glycine, whose carbonyl resonance also served as external, secondary chemical shift standard at 176.06 ppm. For the final $^{13}$C CP/MAS NMR spectrum 1600 scans (0% srC' dots and 30% srC' dots) and 2400 scans (60% srC' dots) were accumulated using 200 μs CP contact times and 3.0 s repetition times due to the probe duty cycle.

Fluorescence correlation spectroscopy (FCS). FCS experiments were performed on a home-built instrument based on a confocal microscope setup. A 635 nm solid state diode laser was used as excitation source (excitation intensity 5 kW/cm$^2$). The fluorescence signal was split into two paths by a 50/50 beam splitter (Chroma) and spectrally filtered from scattered light by two 650 nm long pass filters (Chroma). Photons were collected by two different avalanche photodiode detectors (SPCM 14, Perkin-Elmer) to eliminate effects of afterpulsing and dead-time, as well as uncorrelated noise in the correlation curves. The photocurrents from the two detectors were digitally cross-correlated with a correlator card (Correlator.com). Before each set of measurements, the observation volume was calibrated with Alexa Fluor 647 as a standard dye. For TMR-functionalized particles a 543 nm HeNe laser was employed and TMR was used as standard dye.

Data were collected in sets of three consisting of five 30 s runs each. Correlation curves were fit to a correlation function, G(τ), accounting for translational and rotational diffusion, as well as for fast photophysical processes (photoinduced cis-trans isomerization or singlet-triplet transitions), as shown in equation (1):

$$G(\tau) = 1 + \frac{1}{N} \cdot \left(1 + \frac{\tau}{\tau_D}\right)^{-1} \cdot \left(1 + \frac{\tau}{\kappa^2 \tau_D}\right)^{-1/2} \cdot \qquad (1)$$

$$\frac{1}{1-T} \cdot (1 - T + T \cdot e^{-\tau/\tau_T}) \cdot (1 + a_R e^{-\tau/\tau_R})$$

Here, N is the mean number of particles within the detection volume, and x is the structure factor calculated from a known diffusion coefficient and given by $\eta = \omega_z/\omega_{xy}$, where $\omega_{xy}$ and $\omega_z$ are the radial and axial radii, respectively, of the observation volume. $\tau_D$ is the characteristic diffusion time of a particle through the observation volume. $\tau_D$ is defined as $\tau_D = \omega_{xy}/4D$, where D is the respective particle diffusion coefficient. T is the time- and space-averaged fraction of fluorophores in the cis photoisimer form or triplet state (triplet state population), respectively, and $\tau_T$ is the characteristic relaxation time that is related to either the photoisomerization process or singlet-triplet state transitions. $\tau_R$ is the typical particle rotation time and $\alpha_R$ the pre-exponential amplitude of rotational relaxation. The Stokes-Einstein relation was applied to determine particle diameters, equation (2):

$$d = 2\frac{k_B T}{6\pi\eta D} \quad (2)$$

The average number of dyes per particle, n, was calculated according to equation (3):

$$n = \frac{C_{dye}}{C_{particle}} \quad (3)$$

Here $C_{dye}$ is the measured dye concentration derived from the dye extinction coefficient using the relative absorbance, and $C_{particle}$ is the particle concentration determined by FCS.

The triplet state population, T, as obtained from FCS measurements for different ATTO647N iC' dots was fitted (see FIG. 5e) using the logistic function of equation (4):

$$T(x) = \frac{T_{max}}{1 + e^{-m(x-x_0)}} \quad (4)$$

Where $T_{max}$ is the maximum value of T(x), x is the percentage amount of IPTMS used in the synthesis, $x_0$ is the IPTMS amount at $T_{max}/2$, and m is the steepness of the curve.

Cell toxicity studies. BxPC3 pancreatic cancer cells were maintained in RPMI 1640 supplemented with 10% FBS at 37° C. with 5% $CO_2$. To measure effects of C' dots or βME on cells, cells at ~70% confluence were washed with PBS, exposed to trypsin, resuspended, and dispensed into 96-well tissue culture plates (20,000 cells per well). Cells were allowed to settle overnight, forming a monolayer ~70-80% confluent. The medium was removed from each well, and replaced with medium supplemented with varying amounts of either 60% srC' dots or βME, or with DMSO (carrier agent) alone as a control, as well as 1× Pen-Strep antibiotic. Cells were then incubated for 6 days (srC' dots) or 16 hours ((ME). Following incubation, medium was removed, cells washed with fresh medium and then incubated for one hour with fresh medium and Presto Blue per the manufacturer's recommendations. The absorbance of the Presto Blue was determined at 570 nm (background 600 nm) using a Tecan Safire microplate reader. Absorption was compared to that of a blank (medium plus Presto Blue in unused wells) to determine % viability of remaining cells, with the DMSO control lane defined as 100% viability, and the empty wells defined as 0% viability. All experiments were performed in triplicate.

Ensemble photoswitching experiments. Photoswitching behavior was studied in nitrogen bubbled deionized water at pH 7.4, using a 100 μL quartz cuvette (Starna) covered with parafilm for the duration of the experiment. All samples were exposed to a defocused 100 mW/$cm^2$ 633 nm laser for 60 min and subsequently illuminated with a 300 nm UV LED source of 10 mW/$cm^2$ for 5 min. For every exposure, it was guaranteed that the entire sample window was evenly illuminated. The absorption was measured before and after red light, and after UV light exposure.

Total internal reflection fluorescence microscopy (TIRFM) measurements. Single particle and single molecule measurements were performed using an inverted Zeiss Elyra microscope operated in TIRF geometry. Samples were placed on an oil-immersion 1.46 NA 100× objective and simultaneously excited by a 640 nm laser (13 mW) and a 405 nm laser (98 μW). Fluorescence signal was spectrally filtered using a 640 nm band pass filter and recorded with an Andor iXon EMCCD camera. For each sample, multiple movies with a series of 10,000 frames and a resolution of 50 ms/frame were acquired. To avoid focal drift, the 'definite focus' focal-drift compensation was activated during image acquisition. For dual color images, particles we first imaged with 640 nm laser line to avoid excitation of Cy3 and Cy5. After collection, band pass filters were changed and immediately imaged with the 561 nm laser line (54 mW) and the same 405 nm laser.

Glass bottom dishes (MatTek P35G-0.170-14-C) were coated with streptavidin using a protocol that was previously established. Immediately before the measurement, biotinylated srC' dots, Cy3-biotin, or Cy5-biotin were immobilized on the streptavidin-coated glass bottom dishes by incubation of nanomolar stock concentrations of sample for several minutes before washing away excess dye or particles with PBS. Cy3-biotin was synthesized by first combining biotin-PEG-NHS with cysteamine for 24 hours in the glovebox, followed by the addition of Cy3-maleimide and reaction for another 24 hours (molar ratios 4:2:1). All imaging experiments were performed on sparsely labeled surfaces in 1 mL PBS at pH 7.4 containing an enzymatic oxygen-scavenging system of 50 μL glucose oxidase (10 mg/mL in PBS), 20 μL catalase (2 mg/mL in PBS), and 5% (w/v) glucose. For experiments in the presence of βME, 100 μL (ME was added to 10 mL PBS of 5% (w/v) glucose and the pH adjusted to pH 7.4. The enzymatic oxygen-scavenging system was freshly prepared before each measurement by adding respective amounts of glucose oxidase and catalase to the imaging buffer prior to each measurement.

Particle photon statistical analysis. Photo-switching behavior of hundreds of different nanoparticles were studied using a custom built Matlab script (FIG. 10). Fluorescence signal locations were identified by taking a maximum intensity projection of the stack and then placing a 7×7 pixel region around it. Fluorescence time traces for every molecule/particle were extracted by integrating a 7×7 pixel region located around the maximum fluorescence intensity signal in the 7×7 pixel region for each frame of the movie and subsequently converting intensity counts to photons based on the electron multiplication gain settings used during fluorescence signal acquisition. Switching events were identified in time traces as signals greater than five times the standard deviation of the background fluctuations. The number of photons per switching event were determined by integrating the switching event above the threshold and then subtracting the calculated average background of the movie. Optical probe on-off duty cycles were calculated by taking the total on-time within a 100 second window, and then averaging over all nanoparticles not yet photobleached. Only switching events with on-times less than one second (20 frames) were considered for analysis.

Particle image reconstruction. Reconstructed super-resolution STORM images where generated using ImageJ plugin ThunderSTORM. Approximate locations of the particles were identified as the maximum peak in a region above an intensity threshold five times the standard deviation of the background. Each localization per frame was fit using maximum likelihood fitting with a two-dimensional Gaussian point spread function (PSF). The final drift-corrected reconstructed image was 1280×1280 pixels with 20 nm per pixel and viewed using normalized Gaussian rendering. For dual color images, both channels were reconstructed independently into two different .tiff files then combined to form the dual colored image.

Total internal reflection fluorescence microscopy (TIRFM) of microtubules. Microtubule images were taken on a home built IX81 Olympus inverted microscope set up. A 561 nm laser (Opto Engine LLC) operated at 50 mW output was coupled into a fiber optic connected to a collimating adapter on the microscope. Fluorescence was collected on an Andor Zyla 5.5 sCMOS camera operating micromanager.

Energy-dispersive X-ray spectroscopy. For sample preparation particle dispersions were up-concentrated using centrifuge spin-filters (GE Healthcare Vivaspin with MWCO 30K) and then drop-casted onto silicon wafers. Samples were kept in a vacuum oven for 7 days at 30° C. The final dry particle layers were about 500 µm thick. Energy-dispersive X-ray spectroscopy (EDS) measurements were carried out on a TESCAN MIRA3 LM field-emission scanning electron microscope with a Quantax System attached, equipped with a Bruker XFlash6160 silicon drift detector. Data were collected at 10 kV. Spectra were normalized for the Si peak and relative peak heights were used to estimate the relative atomic ratios present in the particles.

Determination of singlet oxygen quantum yields, $\Phi_A$. Measurements were carried out in ethanol with DPBF as a singlet oxygen detector molecule. The DPBF band at 410 nm and $\lambda_{max}$ of each dye were absorption matched across a particle series. For measurements of effective $\Phi_A$ samples were concentration matched. The spectra were exposed and measured in a 100 µL quartz cuvette (Starna). Samples were evenly exposed to a 635 nm solid-state laser at 3 mW/cm$^2$ and 1 cm spot size. Measurements were started immediately after DPBF addition. The decrease of the 410 nm DPBF band was measured at various exposure times and corrected against a baseline. $\Phi_A$ for each sample was calculated by comparing to MB ($\Phi_A$=0.520 in ethanol) as a standard (see example calculations).

Materials. Aluminum-tri-sec-butoxide (ASB), (3-aminopropyl)triethoxysilane (APTES), ammonium hydroxide (28 wt % in $H_2O$), ammonia solution (2.0 M in ethanol), dimethyl sulfoxide (DMSO), 1,3-diphenylisobenzofuran (DPBF), (3-iodopropyl)trimethoxysilane (IPTMS), (3-mercaptopropyl) trimethoxysilane (MPTMS), 2-propanol (anhydrous 99.5%), tetramethyl orthosilicate (TMOS), isopropanol, methylene blue (MB), β-mercaptoethanol (βME), glucose, guanosine 5'-triphosphate sodium salt hydrate, Paclitaxel, and glucose oxidase were purchased from Sigma Aldrich. Catalase was purchased from Roche Applied Science. Methoxy-terminated poly(ethylene glycol) (PEG-silane, molar mass of ~0.5 kg/mol) and N-(2-aminoethyl)-3-aminopropyl triethoxysilane were purchased from Gelest Inc. 4% formaldehyde methanol free was purchased from Invitrogen and 50% glutaraldehyde in PBS was purchased from Electron Microscopy Sciences. Heterobifunctional PEGs with biotin and maleimide groups (biotin-PEG-mal, molar mass of ~922 g/mol) and biotin and NHS ester groups (biotin-PEG-NHS, molar mass of ~589 g/mol) were purchased from Quanta BioDesign. Cy3-NHS, Cy3-maleimide, Cy5-NHS, and Cy5-maleimide florescent dyes were purchased from GE Healthcare. ATTO647N-NHS, and ATTO647N-maleimide, and MB2-NHS, dyes were purchased from ATTO-Tec. DY-782-NHS dye was purchased from Dyomics. Cy5-biotin and Cy3-maleimide (for synthesis of Cy3-biotin) dyes were purchased from Click Chemistry Tools. Ethanol (absolute anhydrous 99.5%) was purchased from Pharmco-Aaper. N-γ-maleimidobutyryloxysuccinimide ester (GMBS) and streptavidin were purchased from Life Technologies. RPMI-1640, fetal bovine serum (FBS), phosphate buffered saline (PBS), 50× penecillin/streptomycin (pen/strep), and presto blue were purchased from Invitrogen. BxPC3 cells were obtained from ATCC. 97% pure porcine brain tubulin protein, PEM general tubulin buffer, and 60% tubulin glycerol buffer were purchased from Cytoskeleton Inc. Methanol was obtained from Macron Chemicals and acetic acid from EMD Millipore Corp. All chemicals were used as received. Deionized (DI) water (18.2 MΩ·cm) was generated using a Millipore Milli-Q system.

Detailed compositional analysis of srC' dots via solid-state NMR spectroscopy and energy-dispersive X-ray spectroscopy (EDS). We performed $^{29}$Si, $^{27}$Al, and $^{13}$C solid state NMR (ssNMR) experiments on three particles: A 0% srC' dot negative control, and two (30% and 60%) srC' dot samples. FIG. 2d in the main text shows the corresponding $^{29}$Si ssNMR spectra. Each spectrum exhibits well separated chemical shifts for T- and Q-groups, respectively. The peaks located around −58 ppm and −67 ppm correspond to T$^2$ (R—Si(OSi)$_2$(OH)) and T$^3$ (R—Si(OSi)$_3$) groups, while peaks located around −95 ppm, −100 ppm, and −110 ppm reflect Q$^2$ (Si(OSi)$_2$(OH)$_2$), Q$^3$ (Si(OSi)$_3$(OH)), and Q$^4$ (Si (OSi)$_4$) groups, respectively (see corresponding local Si structure in insets of FIG. 2d). Probably some amount of silica substitution by aluminum, for example of the Q$^3$ groups (Si(OSi)$_2$(OAl)(OH)), leads to the broadening of the Q species especially between −90 and −100 ppm. In case of 0% srC' dots, Q-group peaks dominate the spectrum expected from lower molar amounts of PEG-silane as compared to TMOS, and consistent with earlier studies on such sub-10 nm aluminosilicate particles. Since the presence of T-groups can only be explained by the presence of PEG-silane bound to the silica particle surface, and surface to volume ratio decreases with increasing particle size moving from 0%, to 30%, and to 60% srC' dots (i.e. 4.1 nm, 5.8 nm, and 7.2 nm, respectively), the increase in T-group peak intensity relative to that of Q-group peaks, and concomitant decrease in silica network density, can only be due to incorporation of increasing amounts of MPTMS into the silica matrix. Furthermore, since the local surface PEG-silane chemistry itself is not expected to change substantially as a function of particle size, the increasing T$^3$ to T$^2$ ratio moving from 0% to 60% srC' dots is also indicative of increasing amounts of thiol-silane (MPTMS) incorporated into the aluminosilicate network. Increased presence of sulfur in the particle network was independently corroborated using energy-dispersive X-ray spectroscopy (EDS). Figure S2 shows EDS spectra for 0%, 30%, 60%, and 80% srC' dots. For comparison, the spectra were normalized to the silicon peak intensity at 1.75 keV, exhibiting a clear increase of the relative sulfur peak intensity at 2.31 keV. The intensity ratios between the three peaks for 30%, 60%, and 80% srC' dots were 1.0:1.8:2.3, close to the sulfur ratios expected from molar MPTMS precursor amounts, 1.0:2.0:2.7, used in the three syntheses.

The $^{27}$Al NMR spectra of 0%, 30%, and 60% srC' dots (FIG. 2e) displayed a narrow peak at approximately 54 ppm, consistent with four-fold (tetrahedrally) coordinated aluminum most likely replacing silicon in the silica network, as also indicated in the Q-species signals in the $^{29}$Si NMR spectra. In addition, the 60% srC' dot spectrum exhibited a minor component around 5 ppm of six-fold (octahedrally) coordinated aluminum likely due to a small amount of out-of-network aluminum. A reduction of Al content was noticeable with increasing MPTMS amount as compared to the control particle: 100%±5% (0% srC' dots), 80%±5% (30% srC' dots), and 69%±5% (60% srC' dots). This is not unexpected, as the sterically demanding 3-mercaptopropyl ligand, with increasing amounts of MPTMS, may make it more difficult to coordinate aluminum into four-fold coordinated sites with silicon.

We performed solid-state CP/MAS $^{13}$C NMR measurements on these hybrid SNPs to characterize the local structure of the organic moieties (FIG. 2f). For the 0% srC' dots peaks appeared at 10 ppm, 23 ppm, and 70 ppm, assigned to carbons of the PEG-silane on the particle surface (see inset in FIG. 2f), and consistent with previously reported observations for PEGylated mesopourous SNPs. The same peaks were visible in both mercaptopropyl containing samples, indicating successful PEGylation of the srC' dots. srC' dots showed additional three peaks at around 13 ppm, 28 ppm, and 42 ppm, not seen for 0% srC' dots. The relative intensities of these three peaks increased with increasing MPTMS in the particle synthesis. These peaks correspond to carbons in mercaptopropyl and dipropyl disulfide groups in the particles (FIG. 2f inset). The broad peak appearing at around 42 ppm is characteristic for the oxidative formation of disulfide bonds during the synthesis. The peak at 13 ppm is due to the $CH_2$ group in mercaptopropyl and dipropyl disulfide groups directly bound to the silicon atom. The majority of sulfur-containing moieties are mercaptopropyl groups, suggested by the dominant peak at 28 ppm, originating from $\alpha$ and $\beta$ carbon atoms of these groups.

Figure 9:
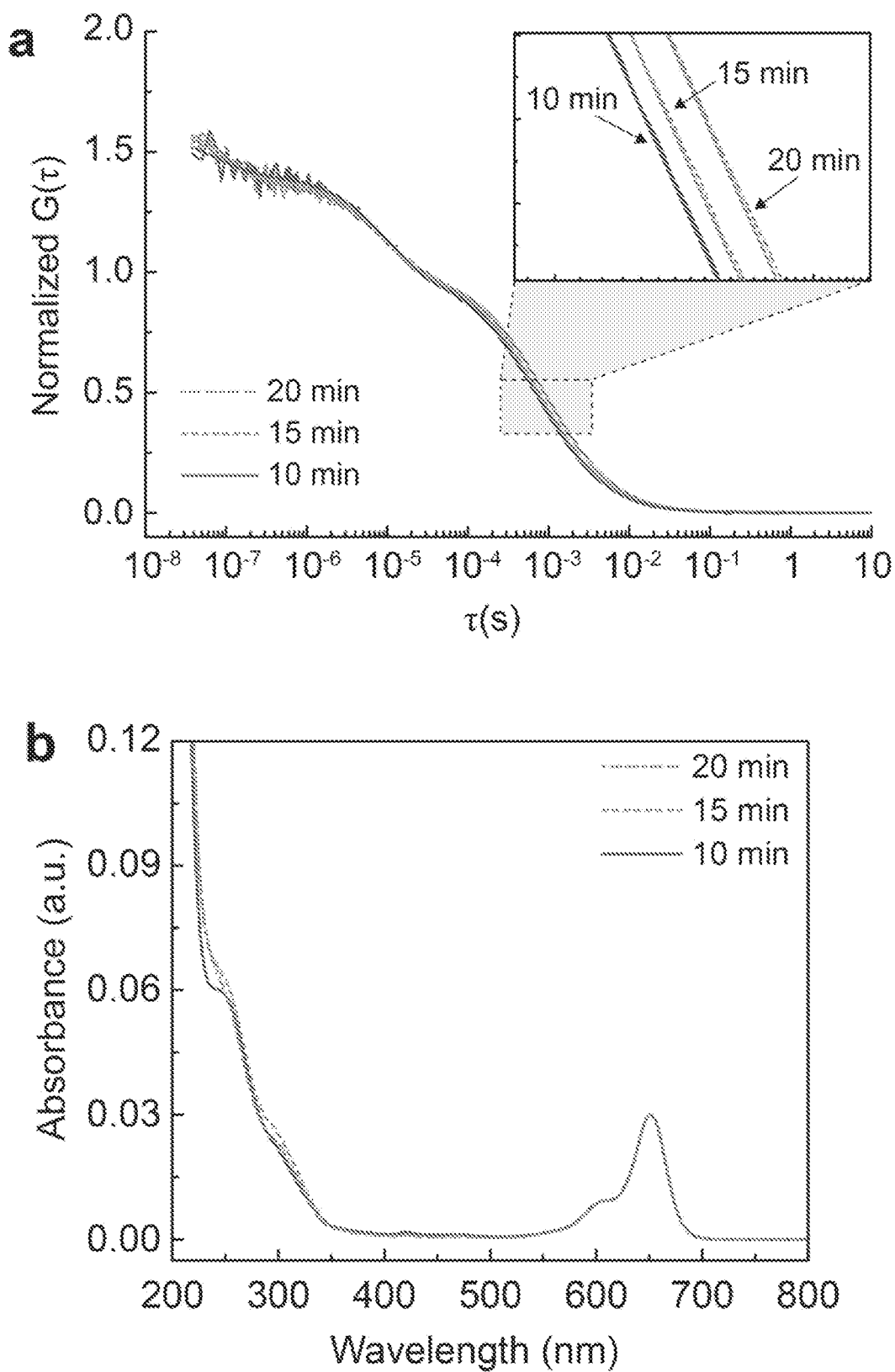
FIG. 9 shows particle size tuning. (a) Normalized FCS autocorrelation curves of srC' dots synthesized at constant MPTMS to TMOS precursor ratio (60%) with particle growth quenched at 10 min, 15 min, and 20 min. Corresponding fits used a correlation function with translational diffusion, cis-trans isomerization, and rotational diffusion components. Shifts to larger lag times for the translational diffusion relaxation indicates larger particles for longer reaction times. Hydrodynamic diameters are d10 min=5.2 nm, d15 min=5.7 nm, and d20 min=6.7 nm, respectively, staying well below the cut off for renal clearance around 8 nm. (b) Corresponding srC' dot absorption spectra normalized to Cy5 absorption. Variations in absorption spectra of these srC' dots were minimal and the characteristic shoulder at 310 nm was maintained.

STORM photon statistical analysis. To analyze the photon statistical behavior of the nanoparticles, we used a custom designed Matlab protocol based on the STORM methodology described by previously described. Since the microscopy was performed on immobilized particles on a substrate, typical drift correction could not be performed. The following protocol was used assuming the microscope had little to no bilateral stage drift and is illustrated in FIG. 9:

1) A maximum intensity projection of the acquired microscopy tiff movie was performed to locate the initial x and y pixel coordinates of the localizations. Any area above the threshold ten times the standard deviation of the background fluctuations was considered a localization. In these areas, we used a maximum-likelihood estimation (MLE) to find the center of the localization since MLE provides the highest precision estimation of position versus other methods.
2) A 7×7 pixel region was then formed around the center of the positions found in the previous step. Since there was no formal drift correction, it was assumed that if the stage had slightly drifted the particle maximum intensity peak would most likely still be within this 7×7 pixel region.
3) Again, using MLE, the maximum of the region was found in the frame. Within this region, the pixel intensity fluctuations were fit to a 2-dimensional 3-parameter Gaussian function defined as:

$$I(x, y) = A + I_1 e^{\left[-\left(\frac{x-x_1}{a_1}\right)^2 - \left(\frac{y-y_1}{b_1}\right)^2\right]} + I_2 e^{\left[-\left(\frac{x-x_2}{a_2}\right)^2 - \left(\frac{y-y_2}{b_2}\right)^2\right]} + I_3 e^{\left[-\left(\frac{x-x_3}{a_3}\right)^2 - \left(\frac{y-y_3}{b_3}\right)^2\right]}$$

A is the background level of the event, $I_{1-3}$ is the amplitude of the peak, $a_{1-3}$ and $b_{1-3}$ define the width of the Gaussian distribution along the x and y directions, respectively, and $x_{1-3}$ and $y_{1-3}$ are the center coordinates found by MLE. The Gaussian was fit to a 7×7 pixel region to provide more data points thus improving the quality of the fit to the region.

4) To obtain the final intensity values for each localization, the above equation was integrated to determine the localization intensity:

$$I_{int}(x,y) = \int_{y-\delta}^{y+\delta} \int_{x-\delta}^{x+\delta} I(x,y) dx dy$$

where $\delta$ is the obtained final half-width of a switching event. The final integrated values were then converted to photoelectrons, yielding the photons detected, using the camera's calibrated curve for the electron multiplication gain settings used during image acquisition.

Photons for each switching event were calculated by integrating between the beginning and the end of each switching event. The integrated values were stored to be plotted as a histogram for probe comparison. Duty cycles were calculated according to the following equation:

$$\text{Duty cycle} = \left(\frac{\sum \tau_{on,i}}{100s}\right)$$

A one hundred second sliding window was used to analyze the dye and the particles to compare their blinking statistics. Large duty cycles are obtained by a high frequency of blinks inside of the one hundred second window.

Microtubule Fixation. Microtubule polymerization, fixation, and labeling were adapted from previously disclosed methods. 0.2 mg tubulin was suspended to 5 mg/mL in a chilled solution of PEM, 10% glycerol, and 1 mM GTP. Tubulin was polymerized into microtubules by incubating the suspension at 37° C. in a water bath for 20 min. Paclitaxel was added to a concentration of 1 mM to stabilize microtubules followed by incubation at 37° C. for 5 min in water bath. Well plates were wetted by 15 min incubation at 25° C. with 141:16 (v/v) methanol:0.5 N HCl. Silanization was accomplished by incubation at 37° C. in a water bath for 15 min using 94% methanol, 5% acetic acid, and 1% N-(2-aminoethyl)-3-aminopropyl triethoxysilane followed by three PBS washes. 0.05 mg microtubule solution was fixed to wells by 10 min incubation at 37° C. with 2% paraformaldehyde and 0.5% glutaraldehyde in PBS followed by three PBS washes. Post-fixation labelling was accomplished by overnight incubation at 25° C. with 60 μL Cy3-srC'dot-PEG-NHS. Cy3-srC'dot-PEG-NHS particles were formed by post-PEGylation surface modification of 300 μL of 27.8 μM Cy3-srC'dot-PEG particles with 45 μL of 20 mg/mL Mal-PEG$_6$-NHS. The maleimide of the Mal-PEG6-NHS clicks to surface mercapto groups on the PEG functionalized particle surface. Wells were washed three times with PBS and replaced with imaging buffer.

TABLE 1

Quantum enhancement as compared to free dye of absorption matched samples, QE, hydrodynamic diameter, d, and number of dyes per particle, n.

| Sample | QE [%] | d [nm] | n [#] |
|---|---|---|---|
| Cy3-NHS | 1.0 | 1.41 | 1.0 |
| Cy3-biotin | 1.4 | 1.46 | 1.0 |
| Cy3 C' dots | 3.5 | 5.13 | 1.5 |
| Cy3 srC' dots | 3.7 | 7.60 | 1.1 |
| Cy5-NHS | 1.0 | 1.29 | 1.1 |
| Cy5-biotin | 2.1 | 1.56 | 1.0 |
| Cy5 C' dots | 2.3 | 5.36 | 1.6 |
| Cy5 srC' dots | 2.3 | 7.43 | 1.1 |
| DY782-NHS | 1.0 | 1.57 | 1.0 |
| DY782 srC' dots | 9.3 | 10.60 | 1.1 |

Example calculation to determine singlet oxygen quantum yield, $\Phi_\Delta$. $\Phi_\Delta$(sample) is determined relative to a standard with known $\Phi_\Delta$(standard) using equation (5):

$$\Phi_\Delta(\text{sample}) = \Phi_\Delta(\text{standard}) \frac{m(\text{sample})}{m(\text{standard})} \quad (5)$$

Here, we used methylene blue (MB) as a standard with known $\Phi_\Delta$(MB)=0.520. With the slopes, m, from the linear fits through the values of the 410 nm DPBF absorption band at different exposure times, $\Phi_\Delta$(sample) can be calculated. With the values from FIG. 15b inset m(ATTO647N 7.5% iC' dots)=0.00314 s$^{-1}$ and m(MB)=0.02506 s$^{-1}$, $\Phi^\Delta$ (ATT0647N 7.5% iC' dots)=0.520(0.02506 s$^{-1}$/0.00314 s$^{-1}$)=0.065.

Although the present disclosure has been described with respect to one or more particular embodiments and/or examples, it will be understood that other embodiments and/or examples of the present disclosure may be made without departing from the scope of the present disclosure.

The invention claimed is:

1. A nanoparticle comprising silica or aluminosilicate; and
5-90 at. % (relative to Si) sulfur atoms covalently bonded to a silica or aluminosilicate network of the nanoparticle; or
1-20 at. % (relative to Si) heavy atoms covalently bonded or non-covalently bonded to a silica or aluminosilicate network of the nanoparticle and/or non-covalently bonded to at least a portion of a surface of the nanoparticle, wherein the heavy atoms are selected from the group consisting of iodine atoms, bromine atoms, and a combination thereof, and the heavy atoms are covalently bonded to the silica or aluminosilicate network of the nanoparticle; or
wherein the heavy atoms are metal ions non-covalently bonded to the silica or aluminosilicate network and/or non-covalently bonded to at least a portion of the surface of the nanoparticle, and the metal ions are selected from the group consisting of gold (Au) ions, silver (Ag) ions, lead (Pb) ions, titanium (Ti) ions, bismuth (Bi) ions, platinum (Pt) ions, indium (In) ions, tin (Sn) ions, antimony (Sb) ions, palladium (Pd) ions, and combinations thereof; and
at least one organic dye molecule, wherein the at least one organic dye molecule is covalently bonded to the silica and/or aluminosilicate network, and at least one polyethylene glycol (PEG) group or moiety covalently bonded to the silica or aluminosilicate network, and wherein the nanoparticle has a longest dimension of 4-9.99 nm.

2. The nanoparticle of claim 1, wherein the organic dye is a fluorescent dye.

3. The nanoparticle of claim 1, wherein the organic dye is selected from the group consisting of cyanine dyes, carborhodamine dyes, boron-dipyrromethene (BODIPY) dyes, xanthene dyes, eosins, rhodamines, methylene blue, and derivatives thereof.

4. The nanoparticle of claim 1, wherein at least a portion of the surface of the nanoparticle is functionalized with polyethylene glycol.

5. The nanoparticle of claim 1, wherein at least a portion of the surface of the nanoparticle is functionalized with one or more ligands or reactive groups.

6. The nanoparticle of claim 5, wherein the ligand is selected from the group consisting of biotin, targeting ligands, antibody fragments, glycans, chelator molecules, and drug molecules.

7. A composition comprising a plurality of nanoparticles of claim 1.

8. The composition of claim 7, wherein the composition further comprises an aqueous medium and the nanoparticles are present as a dispersion in the aqueous medium.

9. The composition of claim 7, wherein the composition further comprises a pharmaceutically acceptable carrier.

10. A photodynamic therapy method comprising:
administering to an individual with an abnormal cell a nanoparticle of claim 1; and
irradiating the individual or a portion thereof with excitation light, wherein the irradiation results in formation of a reactive ion species.

11. A nanoparticle comprising silica or aluminosilicate; and
1-20 at. % (relative to Si) heavy atoms covalently bonded or non-covalently bonded to a silica or aluminosilicate network of the nanoparticle and/or non-covalently bonded to at least a portion of a surface of the nanoparticle, wherein the heavy atoms are selected from the group consisting of iodine atoms, bromine atoms, metal ions, and a combination thereof, and the metal ions are selected from the group consisting of gold (Au) ions, silver (Ag) ions, lead (Pb) ions, titanium (Ti) ions, bismuth (Bi) ions, platinum (Pt) ions, indium (In) ions, tin (Sn) ions, antimony (Sb) ions, palladium (Pd) ions, and combinations thereof; and
at least one organic dye molecule, wherein the at least one organic dye molecule is covalently bonded to the silica and/or aluminosilicate network, and at least one polyethylene glycol (PEG) group or moiety covalently bonded to the silica or aluminosilicate network, and wherein the nanoparticle has a longest dimension of 4-9.99 nm.

12. A method of making a nanoparticle of claim 11, comprising:
a) forming a reaction mixture at room temperature comprising: water, tetramethyl orthosilicate (TMOS), an organic dye precursor, a heavy atom-containing precursor, and optionally an alumina-forming precursor; and
b) holding the reaction mixture at a time (t$^1$) and temperature (T$^1$), whereby the nanoparticle is formed.

13. The method of claim 12, further comprising the steps of:
c) adding at room temperature to the reaction mixture from b) a PEG-silane conjugate and holding the resulting reaction mixture at a time (t$^2$) and temperature (T$^2$); and
d) heating the mixture from c) thereby forming therein.

14. The method of claim 13, wherein at least a portion of the PEG-silane conjugate comprises a ligand or a reactive group.

15. The method of claim 14, wherein the PEG-silane conjugate comprising a ligand or a reactive group is added in addition to the PEG-silane conjugate in c), whereby a silica nanoparticle or an aluminosilicate nanoparticle surface functionalized with PEG groups and PEG groups comprising a ligand or a reactive group are formed.

16. The method of claim 13, wherein before or after the PEG-silane conjugate is added in c) a PEG-silane conjugate comprising a ligand or a reactive group is added at room temperature to the reaction mixture comprising the nanoparticle from b), holding the resulting reaction mixture at a time ($t^4$) and temperature ($T^4$), and subsequently heating the resulting reaction whereby a nanoparticle surface functionalized with PEG groups comprising a ligand or a reactive group is formed, optionally, subsequently adding at room temperature to the resulting reaction mixture a PEG-silane conjugate, and holding the resulting reaction mixture at a time ($t^6$) and temperature ($T^6$), and optionally heating the resulting mixture, whereby nanoparticles surface functionalized with PEG groups and PEG groups comprising a ligand or a reactive group are formed.

17. The method of claim 15, wherein the nanoparticle is surface functionalized with PEG groups comprising a reactive group, and, the method further comprises reacting the reactive group with a ligand functionalized with a second reactive group, thereby forming a nanoparticle surface functionalized with a ligand.

18. A method of obtaining an image of a sample or a portion thereof, or an image of an individual or a portion thereof, comprising:

contacting the sample or the individual with a nanoparticle of claim 11;

irradiating the sample or a portion thereof, or the individual or a portion thereof, with excitation light, thereby exciting the at least one organic dye molecule; and obtaining a fluorescence image of the sample or portion thereof, or the individual or a portion thereof.

19. A photodynamic therapy method comprising:

administering to an individual with an abnormal cell a nanoparticle of claim 11; and irradiating the individual or a portion thereof with excitation light, wherein the irradiation results in formation of a reactive ion species.

20. A method of making a nanoparticle of claim 1, comprising:

a) forming a reaction mixture at room temperature comprising: water, tetramethyl orthosilicate (TMOS), an organic dye precursor, a sulfur atom-containing precursor or a heavy atom-containing precursor, and optionally an alumina-forming precursor; and b) holding the reaction mixture at a time (t1) and temperature (T1), whereby the nanoparticle is formed.

21. The method of claim 20, further comprising the steps of:

c) adding at room temperature to the reaction mixture from b) a PEG-silane conjugate and holding the resulting reaction mixture at a time (t2) and temperature (T2); and d) heating the mixture from c) thereby forming therein.

22. The method of claim 21, wherein at least a portion of the PEG-silane conjugate comprises a ligand or a reactive group.

23. The method of claim 22, wherein the PEG-silane conjugate comprising a ligand or a reactive group is added in addition to the PEG-silane conjugate in c), whereby a silica nanoparticle or an aluminosilicate nanoparticle surface functionalized with PEG groups and PEG groups comprising a ligand or a reactive group are formed.

24. The method of claim 21, wherein before or after the PEG-silane conjugate is added in c) a PEG-silane conjugate comprising a ligand or a reactive group is added at room temperature to the reaction mixture comprising the nanoparticle from b ), holding the resulting reaction mixture at a time (t4) and temperature (T4), and subsequently heating the resulting reaction whereby a nanoparticle surface functionalized with PEG groups comprising a ligand or a reactive group is formed, optionally, subsequently adding at room temperature to the resulting reaction mixture a PEG-silane conjugate, and holding the resulting reaction mixture at a time (t6) and temperature (T6), and optionally heating the resulting mixture, whereby nanoparticles surface functionalized with PEG groups and PEG groups comprising a ligand or a reactive group are formed.

25. The method of claim 24, wherein the nanoparticle is surface functionalized with PEG groups comprising a reactive group, and, the method further comprises reacting the reactive group with a ligand functionalized with a second reactive group, thereby forming a nanoparticle surface functionalized with a ligand.

26. A method of obtaining an image of a sample or a portion thereof, or an image of an individual or a portion thereof, comprising:

contacting the sample or the individual with a nanoparticle of claim 1;

irradiating the sample or a portion thereof, or the individual or a portion thereof, with excitation light, thereby exciting the at least one organic dye molecule; and obtaining a fluorescence image of the sample or portion thereof, or the individual or a portion thereof.

* * * * *